US010821160B2

(12) United States Patent
Lavie et al.

(10) Patent No.: US 10,821,160 B2
(45) Date of Patent: Nov. 3, 2020

(54) L-ASPARAGINASE VARIANTS AND FUSION PROTEINS WITH REDUCED L-GLUTAMINASE ACTIVITY AND ENHANCED STABILITY

(71) Applicant: THE BOARD OF TRUSTEES OF THE UNIVERSITY OF ILLINOIS, Urbana, IL (US)

(72) Inventors: Arnon Lavie, Chicago, IL (US); Hien-Anh Nguyen, Chicago, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 54 days.

(21) Appl. No.: 16/080,435

(22) PCT Filed: Mar. 1, 2017

(86) PCT No.: PCT/US2017/020090
§ 371 (c)(1),
(2) Date: Aug. 28, 2018

(87) PCT Pub. No.: WO2017/151707
PCT Pub. Date: Sep. 8, 2017

(65) Prior Publication Data
US 2019/0070274 A1 Mar. 7, 2019

Related U.S. Application Data

(60) Provisional application No. 62/301,806, filed on Mar. 1, 2016, provisional application No. 62/347,376, filed on Jun. 8, 2016, provisional application No. 62/446,026, filed on Jan. 13, 2017.

(51) Int. Cl.
| | |
|---|---|
| *C12N 9/82* | (2006.01) |
| *C12N 15/00* | (2006.01) |
| *A61K 38/50* | (2006.01) |
| *C07K 14/52* | (2006.01) |
| *A61K 47/66* | (2017.01) |
| *A61K 47/68* | (2017.01) |
| *A61K 47/65* | (2017.01) |
| *A61P 35/00* | (2006.01) |
| *C12N 15/52* | (2006.01) |
| *C12R 1/18* | (2006.01) |
| *A61K 38/00* | (2006.01) |

(52) U.S. Cl.
CPC ............ *A61K 38/50* (2013.01); *A61K 47/65* (2017.08); *A61K 47/67* (2017.08); *A61K 47/6815* (2017.08); *A61P 35/00* (2018.01); *C07K 14/52* (2013.01); *C12N 9/82* (2013.01); *C12N 15/52* (2013.01); *C12R 1/18* (2013.01); *C12Y 305/01001* (2013.01); *A61K 38/00* (2013.01); *C07K 2319/35* (2013.01); *C07K 2319/74* (2013.01); *Y02A 50/473* (2018.01)

(58) Field of Classification Search
CPC .... C12N 9/82; C12N 15/00; C12Y 305/01001
See application file for complete search history.

(56) References Cited

U.S. PATENT DOCUMENTS

| | | | |
|---|---|---|---|
| 2009/0131317 A1 | 5/2009 | Angell et al. | 514/1.1 |
| 2010/0143324 A1 | 6/2010 | Mononen et al. | 424/94.6 |
| 2012/0009123 A1 | 1/2012 | Trieu | 424/1.69 |
| 2012/0100121 A1 | 4/2012 | Abribat | 424/94.3 |
| 2013/0330316 A1 | 12/2013 | Kundu et al. | 424/94.6 |
| 2015/0337027 A1 | 11/2015 | Hill et al. | 424/134.1 |
| 2016/0213759 A1 | 7/2016 | Rempe et al. | |

FOREIGN PATENT DOCUMENTS

| | | |
|---|---|---|
| CN | 104371993 | 2/2015 |
| WO | WO 2011/003633 | 1/2011 |
| WO | WO 2012/170640 | 12/2012 |
| WO | WO 2015/038639 | 3/2015 |

OTHER PUBLICATIONS

Kouno et al. 2013; Targeted delivery of tumor necrosis factor-related apoptosis-inducing ligand to ketatinocytes with pemphigus monoclonal antibody. J. Invest. Dermatol. 133(9): 2212-2220.*
Meier et al. 2004; Foldon, the natural trimerizaion domain of T4 fibritin dissociates into a monomeric A-state from containing a stable Beta-hairpin: atomic details of timer dissociation and local beta-hairpin stability from residual dipolar couplings. J. Mol. Biol. 344: 1051-1069.*
Kotzia et al. 2007; L-Asparaginase from Erwinia chrysanthemi 3937: Cloning, expression and characterization. J. Biotechnol. 127: 657-669.*
Pourhossein et al. 2014; Cloning, expression, purification and characterization of Erwinia carotovora L-asparaginase in *Escherichia coli*. Advanced Biomedical Research. 3:82, pp. 1-6.*
Aghaiypour et al. "Structural Basis for the Activity and Substrate Specificity of Erwinia chrysanthemi L-Asparaginase" Biochemistry 2001 40:5655-5664.
Karpel-Massler et al."Metabolic Reprogramming of Glioblastoma Cells by L-Asparaginase Sensitizes for Apoptosis in vitro and in vivo" Oncotarget 2016 7:33512-33528.
Kotzia, G.A. and Labrou, N.E. "Engineering Thermal Stability of L-Asparaginase by in vitro Directed Evolution" FEBS Journal 2009 276:1750-1761.
Nguyen et al "Design and Characterization of Erwinia Chrysanthemi L-Asparaginase Variants with Diminished L-Glutaminase Activity" Journal of Biochemistry 2016 291: 17664-17676.
Nguyen et al. "Structural Insight into Substrate Selectivity of Erwinia chrysanthemi L-asparaginase" Biochemistry 2016 55:1246-1253.

(Continued)

*Primary Examiner* — Karen Cochrane Carlson
(74) *Attorney, Agent, or Firm* — Licata & Tyrrell P.C.

(57) ABSTRACT

Variant *Erwinia chrysanthemi* L-asparaginases with reduced L-glutaminase activity and enhanced in vivo circulation are described as are fusion proteins containing an L-asparaginase and three tandem soluble domains of TRAIL for use in the treatment of cancers such as acute lymphoblastic leukemia and acute myeloid leukemia.

69 Claims, 5 Drawing Sheets

Specification includes a Sequence Listing.

(56) References Cited

OTHER PUBLICATIONS

Offman et al. "Rational Engineering of L-Asparaginase Reveals Importance of Dual Activity for Cancer Cell Toxicity" Blood 2011 117:1614-1621.
Parmentier et al. "Glutaminase Activity Determines Cytotoxicity of L-Asparaginases on Most Leukemia Cell Lines" Leuk. Res. 2015 39:757-762.
International Search Report and Written Opinion in PCT/US2017/020090 dated Jul. 12, 2017.
International Preliminary Report on Patentability in PCT/US2017/020090 dated Sep. 4, 2018.

* cited by examiner

*SITE 1 - A31

*SITE 2 - E63

*SITE 3 - P123

*SITE 4 - S254

FIG. 3

L-ASPARAGINASE VARIANTS AND FUSION PROTEINS WITH REDUCED L-GLUTAMINASE ACTIVITY AND ENHANCED STABILITY

This application is a U.S. National Stage Application of PCT/US2017/020090 filed Mar. 1, 2017 and claims the benefit of priority of U.S. Provisional Application Nos. 62/301,806, filed Mar. 1, 2016; 62/347,376, filed Jun. 8, 2016; and 62/446,026, filed Jan. 13, 2017, the contents of which are incorporated herein by reference in their entireties.

INTRODUCTION

This invention was made with government support under Grant Number RO1 EB013685 awarded by the National Institutes of Health and Grant Number I01BX001919 awarded by the Veteran's Administration. The government has certain rights in the invention.

BACKGROUND

Certain cancers, such as acute lymphoblastic leukemia (ALL), are dependent upon scavenging Asn from blood, a factor most commonly attributed to the lack/low expression of asparagine synthetase in such cancers. Accordingly, L-asparaginases have been identified as critical components in the treatment of these cancers. L-asparaginases are enzymes that have dual activities. The predominant one, the L-asparaginase activity, hydrolyzes the amino acid L-asparagine (Asn) into L-aspartic acid (Asp) and ammonia. The secondary activity is an L-glutaminase activity, which hydrolyze L-glutamine (Gln) to L-glutamic acid (Glu) and ammonia. For FDA-approved enzymes, e.g., ELSPAR® (enzyme obtained from *Escherichia coli*) and ERWINAZE® (enzyme obtained from *Erwinia chrysanthemi*), the L-glutaminase activity ranges from 2 to 10% of the primary L-asparaginase activity. Whereas the importance of the L-asparaginase activity of these drugs is accepted, there are conflicting reports as to the importance of L-glutaminase activity in killing leukemic cells. Moreover, the L-glutaminase activity has been associated with much of the clinical toxicity of L-asparaginases. In fact, toxic side effects of L-asparaginase treatment severely limit the use of this anti-cancer drug.

Given the therapeutic advantage of using L-asparaginases in treatment of ALL, more effective variants of these enzymes are sought. Toward this end, the crystal structure of *Erwinia chrysanthemi* L-asparaginase in complex with Asp or Glu has been solved. This analysis indicates that the position of most active site residues (Glu63, Thr95, Asp96, and Lys168) is insensitive to the nature of the ligand (Asp versus Glu). In contrast, the conformation of Thr15 is sensitive to the type of ligand (Nguyen, et al. (2016) *Biochemistry* 55(8):1246-53). In earlier work, two active-site residues, Glu63 and Ser254, of *Erwinia chrysanthemi* (ErA) have been postulated to correlate with glutaminase activity, wherein their substitution by Gln and Asn, respectively, was suggested to lead to minimal L-glutaminase activity (Aghaiypour, et al. (2001) *Biochemistry* 40(19): 5655-5664).

Mutational analysis indicates that replacement of Asp133 with Valine or Leucine confers thermostability to the ErA L-asparaginase (Kotzia & Labrou (2009) *FEBS J.* 276(6): 1750-61). Mutation of Asn133 and Val143 of *Bacillus subtilis* L-asparaginase has also been shown to increase L-asparaginase activity (CN 104371993). Further, an asparagine endopeptidase-resistant mutant of *Escherichia coli* L-asparaginase (Asn24Ala), when combined with an interface mutation (Tyr250Leu), provides an enzyme with minimal L-glutaminase activity, reduced cytotoxicity, and an overall $IC_{50}$ of 243% compared with wild-type enzyme (Offman, et al. (2011) *Blood* 117:1614-21). Moreover, Parmentier, et al. ((2015) *Leuk. Res.* 39(7):757-62) describe a *Helicobacter pylori* L-asparaginase double mutant (Met121Cys/Thr169Met) with wild-type L-asparaginase activity and diminished L-glutaminase activity, which exhibited reduced activity against human leukemia cell lines. In addition, WO 2015/038639 discloses a modified L-asparaginase enzyme from *E. coli* with substitutions at positions 58 and 59, which exhibit reduced L-glutaminase activity. US 2013/0330316 describes a mutant of L-asparaginase from *Pyrococcus furiosus*, which includes the substitutions Lys274Glu, Thr53Gln, and Thr53Gln/Lys274Glu, and has high thermostability, pH stability and no L-glutaminase activity.

Post-translationally modified versions of L-asparaginases have also been described. For example, L-asparaginase has been linked to polyethylene glycol (PEG-asparaginase) in order to reduce the immune side effects of the L-asparaginase treatment and prolong the half-life of the enzyme during the therapy. See US 2010/0143324 and US 2012/0100121. Fusion of an albumin binding peptide to L-asparaginase has been also suggested for use in increasing the half-life of this enzyme. See US 2012/0009123 and US 2016/0213759.

Other approaches for treating cancer using L-asparaginase have included co-administration of the L-asparaginase with a TNF-related apoptosis-inducing ligand (TRAIL) agonist or TRAIL receptor agonist, e.g., three soluble TRAIL domains and an additional functional domain such as an antibody fragment. See US 2015/0337027; US 2009/0131317 and WO 2012/170640. In this respect, L-asparaginase has been shown to overcome resistance to both intrinsic apoptosis induced by the Bcl-2/Bcl-xL inhibitor, ABT263, and extrinsic apoptosis mediated by TRAIL in glioma cells that are resistant toward L-asparaginase single treatment (Karpel-Massler, et al. (2016) *Oncotarget* 7(23): 33512-28).

SUMMARY OF THE INVENTION

This invention provides *Erwinia chrysanthemi* L-asparaginase (ErA) variants having an amino acid substitution at one or more of positions 31, 63 and 254 of SEQ ID NO:1. In some embodiments, the amino acid substitution at position 31 includes an isoleucine, valine, leucine, or threonine; the amino acid substitution at position 63 includes a glutamine, asparagine, or aspartate; and the amino acid substitution at position 254 includes an asparagine or glutamine. In certain embodiments, the ErA variant has an amino acid sequence as set forth in SEQ ID NO:2, SEQ ID NO:3, SEQ ID NO:4, SEQ ID NO:5, SEQ ID NO:6 or SEQ ID NO:7. Ideally, the ErA variant exhibits: an L-asparaginase reaction rate ($k_{cat}$) of least 75% of wild-type ErA enzyme; exhibits a Km for Asn of less than 250 µM; a L-glutaminase reaction rate ($k_{cat}$) of less than 60% of wild-type ErA enzyme; and/or a Km for Gln of greater than 3 mM. In further embodiments, the ErA variant further includes: a histidine tag, a SUMO tag, an albumin-binding domain, PEGylation, and/or three tandem soluble domains of TRAIL. In particular embodiments, the soluble domains of TRAIL include residues 115-281 of human TRAIL; the three tandem soluble domains of TRAIL are linked to one another via a peptide linking group including one to eight amino acid residues, e.g., selected from glycine and serine; and/or the three tandem soluble domains of TRAIL are linked to the ErA variant via a peptide linking group including one to twenty amino acid residues, e.g., selected from glycine and serine. In some embodiments, PEGylation is achieved with an ErA variant having a cysteine residue at position 72, 76, 79, 84, 85, 206, 210, 215, 216, 235, 239, 240, 261, 264, 265, 268, 269, 318, 322, or a combination thereof.

The invention also provides a fusion protein composed of an L-asparaginase linked to three tandem soluble domains of TRAIL. In some embodiments, the soluble domains of TRAIL include residues 115-281 of human TRAIL; the three tandem soluble domains of TRAIL are linked to one another via a peptide linking group including one to eight amino acid residues, e.g., selected from glycine and serine; and/or the three tandem soluble domains of TRAIL are linked to the ErA variant via a peptide linking group including one to twenty amino acid residues, e.g., selected from glycine and serine. In other embodiments, the L-asparaginase of the fusion protein is an L-asparaginase from *Erwinia chrysanthemi* or *Escherichia coli*. In certain embodiments, the *E. chrysanthemi* L-asparaginase (ErA) is a variant having an amino acid substitution at one or more of positions 31, 63 and 254 of SEQ ID NO:1. Additionally, the fusion protein further includes: a histidine tag, a SUMO tag, an albumin-binding domain, and/or PEGylation. In some embodiments, the PEGylated L-asparaginase is an L-asparaginase from *Erwinia chrysanthemi* having a cysteine residue at position 72, 76, 79, 84, 85, 206, 210, 215, 216, 235, 239, 240, 261, 264, 265, 268, 269, 318, 322, or a combination thereof.

Nucleic acid molecules, expression vectors, host cells and pharmaceutical compositions containing the ErA variant or fusion proteins are also provided, as are methods of treating cancer by administering to a subject in need of treatment an effective amount of the ErA variant or fusion proteins, optionally in combination with a stable form of TRAIL.

BRIEF DESCRIPTION OF THE DRAWINGS

FIG. 1A) and SUP-B15 (human B-ALL; FIG. 1B) cell lines.

FIG. 3 shows a sequence alignment of L-asparaginases from *Erwinia chrysanthemi* (A; UniProt entry P06608; SEQ ID NO:1), *E. carotovora* (B; UniProt entry Q6Q4F4; SEQ ID NO:8), *Escherichia coli* (C; UniProt entry P00805; SEQ ID NO:9), *Helicobacter pylori* (D; UniProt entry O25424; SEQ ID NO:10), *Wolinella succinogenes* (E; UniProt entry P50286; SEQ ID NO:11), and *Cavia porcellus* (guinea pig) (F; UniProt entry H0W0T5; SEQ ID NO:12). Strictly conserved residues are indicated with underlining. The four sites selected for mutagenesis for the goal of reducing the L-glutaminase activity are indicated. The *E. chrysanthemi*, *E. carotovora* and *E. coli* enzymes contain an N-terminal signal peptide, which is not included in the alignment. For the guinea pig enzyme, only residues in its N-terminal L-asparaginase domain are shown.

DETAILED DESCRIPTION OF THE INVENTION

Figure 1A:
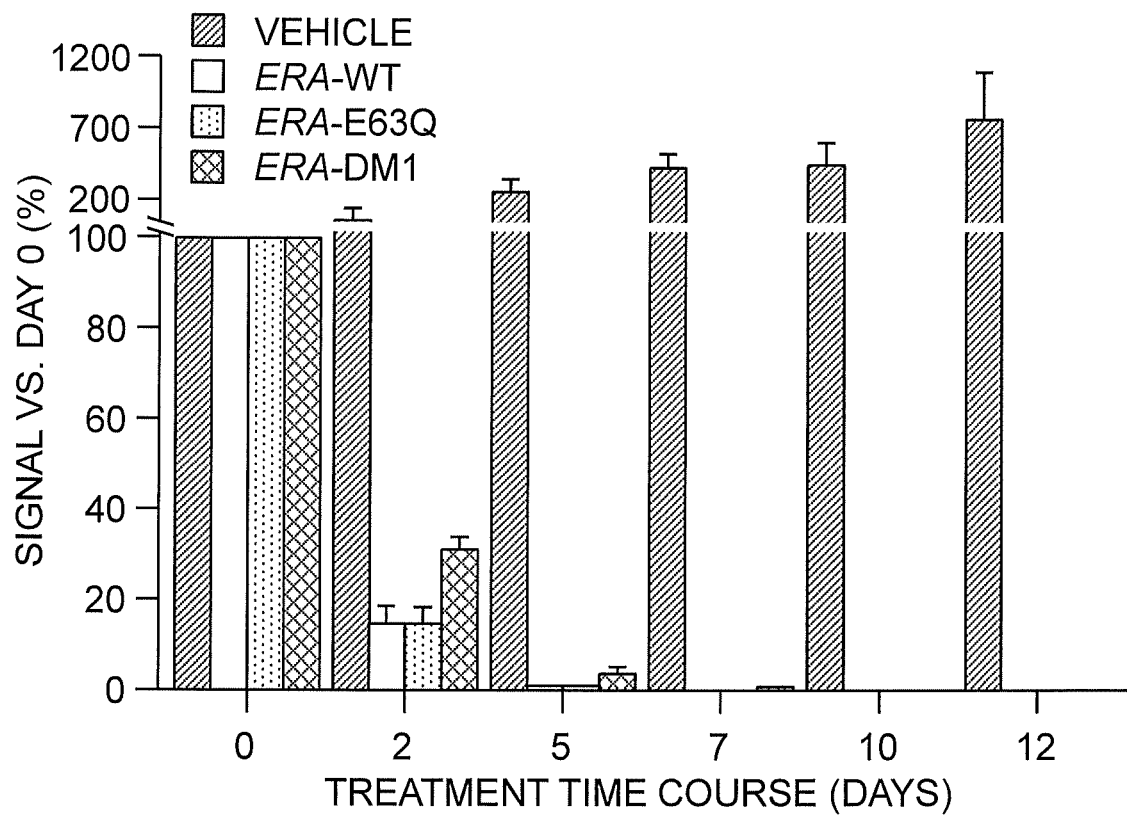
FIGS. 1A and 1B show that L-asparaginases with reduced L-glutaminase activity rapidly decrease the number of cancer cells in an animal of ALL using luciferase-expressing LOUCY (human T-ALL.

It has now been found that the toxic side effects attributed to the L-glutaminase activity of *Erwinia chrysanthemi* L-asparaginase (ErA) can be diminished by mutation of one or more of amino acid residues 31, 63 and 254 of the ErA enzyme. In addition, in vivo circulation time of L-asparaginase can be increased by the N- or C-terminal addition of a histidine tag, SUMO tag, and/or albumin binding domain. Moreover, fusion of a L-asparaginase to three tandem soluble domains of TRAIL has now been demonstrated to facilitate cell death by both providing the necessary signals for apoptosis (L-asparaginase) and inducing the process of apoptosis (TRAIL). Accordingly, this invention provides variant L-asparaginases and fusion proteins containing L-asparaginases, as well as combinations thereof, for use in the treatment of cancers such as lymphomas and leukemias, which are dependent upon the presence of an external supply of Asn. The improved safety of the instant L-asparaginases will provide benefit to current patient populations (e.g., those with pediatric ALL), and extended use in other patient populations (e.g., adult ALL, AML, and other cancers).

As is known in the art, L-asparaginases (L-asparagine aminohydrolase, E.C. 3.5.1.1) are amidases that hydrolyses the amide bond in Asn to Asp and ammonia (Kumar & Verma (2012) *Asian J. Biochem. Pharma Res.* 3:197-205). An L-asparaginase of use in this invention can be obtained from any suitable organism including an animal, microbe, or plant. Ideally, the L-asparaginase is obtained from a microorganism such as a bacterium, fungus, yeast, actinomycete or alga. Bacterial species from which the present L-asparaginase can be obtained include, but are not limited to, *E. coli* (Cedar & Schwartz (1968) *J. Bacteriol.* 96:2043-8; see also UniProt entry P00805), *Erwinia carotovora* (Kotzia & Labrou (2005) *J. Bacteriol.* 119:309-323), *Pseudomonas stutzeri* (Manna, et al. (1995) *Curr. Microbiol.* 30:291-8), *Pseudomonas acidovoras* (Davis, et al. (1977) *J. Bacteriol.* 129:1379-86), *Erwinia aroideae* (Peterson & Ciegler (1969) *Appl. Microbiol.* 18:64-7), *Thermus thermophiles* (Pritsa, et al. (2001) *Anticancer Drugs* 12:137-42), *Thermus aquaticus* (Curran, et al. (1985) *Arch. Biochem. Biophys.* 241:571-6), *Staphylococcus aureus* (Rozalska & Mikucki (1992) *Acta Microbiol. Pol.* 41:145-50), *Vibrio succinogenes* (Kafkewitz & Goodman (1974) *Appl. Microbiol.* 27:206-9), *Citrobacter freundi* (Davison, et al. (1977) *Biochim. Biophys. Acta* 480:282-94), *Proteus vulgaris* (Tosa, et al. (1972) *J. Biochem.* 11:217-22), *Zymomonas mobilis* (Pinheiro, et al. (2001) *Biomater. Diagn.* 6:243-4), *Bacillus subtilis* (Fisher & Wray (2002) *J. Bacteriol.* 184:2148-54), *Bacillus licheni-* formis (Golden & Bernlohr (1985) *J. Bacteriol.* 164:938-40), *Bacillus circulans* MTCC 8574 (Hymavathi, et al. (2009) *Appl. Biochem. Biotechnol.* 159:191-98), *Enterobacter aerogenes* (Mukherjee, et al. (2000) *Appl. Microbiol. Biotechnol.* 53:180-4), *Serratia marcescens* (Khan, et al. (1970) *Biochem. Biophys. Res. Commun.* 41:525-33), *Wolinella succinogenes* (see UniProt entry P50286), *Helicobacter pylori* (see UniProt entry O25424), and *Cavia porcellus* (guinea pig) (see UniProt entry H0W0T5). Fungal and yeast species such as *Aspergillus tamari, Aspergillus terreus, Aspergillus awamori, Cylindrocarpon obtusisporum, Fusarium roseum, Fusarium saloni, Saccharomyces cerevisae, Candida utilis, Candida guilliermondii* and *Rhodosporodium toruloids* can also be sources of the present L-asparaginase.

The most widely used and commercially available L-asparaginases are derived from *E. coli* or from *Erwinia* sp. Within the *Erwinia* species, *E. chrysanthemi*- and *E. carotovora*-derived enzymes are known and include, but are not limited to enzymes isolated from *E. chrysanthemi* NCPPB 1066 (see UniProtKB Accession No. P06608), *E. chrysanthemi* 3937 (see GENBANK Accession No. AAS67028), *E. chrysanthemi* NCPPB 1125 (see GENBANK Accession No. CAA31239), *E. carotovora* subsp. *atroseptica* (see GENBANK Accession No. AAS67027 or UniProtKB Accession No. Q6Q4F4) and *E. carotovora* (see GENBANK Accession No. AAP92666). Accordingly, it is preferred that the L-asparaginase used herein is derived from *E. coli, E. chrysanthemi* or *E. carotovora*. In particular, it is preferable that the L-asparaginase is obtained from *E. chrysanthemi*. In certain embodiments, an L-asparaginase used herein lacks an N-terminal leader sequence and has an N-terminal methionine residue. An exemplary *E. chrysanthemi* L-asparaginase has the amino acid sequence set forth in SEQ ID NO:1.

An "ErA variant" refers to any non-naturally occurring form of an ErA enzyme that displays L-asparaginase activity and includes at least one mutation or modification that reduces or diminishes L-glutaminase activity, increases stability, and/or increases in vivo circulation time of the ErA as compared to a wild-type ErA enzyme. By comparison, a "wild-type" L-asparaginase refers to the typical form of L-asparaginase when isolated from a naturally occurring source. A wild-type is that which is most frequently observed in a natural population and is thus arbitrarily designated the normal or wild-type form.

As demonstrated herein, mutation of one or more of positions 31, 63 and 254 of *E. chrysanthemi* L-asparaginase (ErA; SEQ ID NO:1) provides an enzyme with reduced or diminished L-glutaminase activity (see Table 7). In particular, 1-glutaminase activity of an. ErA variant is reduced to between 0 and 65%, 0 and 50%, 0 and 35%, 0 and 25%, 0 and 20%, 0 and 15%, or 0 and 10% of wild-type ErA activity. Ideally, the ErA variant of the invention exhibits a L-glutaminase reaction rate ($k_{cat}$) of less than 60%, 50%, 40%, 30% or 20% of the $k_{cat}$ of a wild-type ErA enzyme. Moreover, it is preferred that the ErA variant exhibits a Km for Gln of greater than 2, 3, 5, 10, 15, 20, 25, 30, 35, 40, 45, 50, 55, 60, 65, 70, 75 or 80 mM. In particular, the invention includes an ErA variant exhibiting a Km for Gln in the range of 2 to 100 mM, 3 to 100 mM, 10 to 100 mM, or 20 to 100 mM.

ErA variants include proteins having a mutation at position 31, 63 and/or 254 of SEQ ID NO:1. Accordingly, ErA variants include mutation of position 31; position 63; position 254; positions 31 and 63; positions 31 and 254; positions 63 and 254; and positions 31, 63 and 254 of SEQ ID NO:1. Mutations in ErA variant proteins include the substitution of Ala31 with an isoleucine, valine, leucine, or threonine; substitution of Glu63 with glutamine, asparagine, or aspartate; and/or substitution of Ser254 with an asparagine or glutamine. Exemplary ErA variant proteins having a mutation at one or more of positions 31, 63 and 254 of SEQ ID NO:1 are provided under SEQ ID NO:2 (E63Q), SEQ ID NO:3 (E63Q-S254N), SEQ ID NO:4 (A31I-E63Q), SEQ ID NO:5 (E63Q-S254Q), SEQ ID NO:6 (A31I-E63Q-S254Q), and SEQ ID NO:7 (A31I-E63Q-S254N).

In addition to ErA, mutations at a corresponding position in other L-asparaginases can also be made. The term "corresponding," when used in the context of comparing, aligning, or identifying equivalent amino acids in one polypeptide sequence with another polypeptide sequence, refers to the comparison or alignment that will yield the highest percent identity when aligned with the other polypeptide sequence. For example, the corresponding position of residues 31, 63 and 254 of ErA in L-asparaginases from *E. carotovora* (UniProt entry Q6Q4F4) are located at positions 29, 61 and 252 of SEQ ID NO:8.

Advantageously, the ErA variant of this invention has an L-asparaginase activity comparable to that of wild-type ErA. In particular, the ErA variant exhibits an L-asparaginase reaction rate ($k_{cat}$) of least 70% of wild-type ErA enzyme. Ideally, the ErA variant exhibits an L-asparaginase $k_{cat}$ in the range of 50 to 150%, 60 to 140%, 70 to 130%, or 80 to 125% of the $k_{cat}$ of a wild-type ErA enzyme. Moreover, it is preferred that the ErA variant exhibits a Km for Asn of less than 250, 200, 150, 140, 130, 120, 110, 100, 90, 80, 70, 60, 50, or 40 µM. In particular, the invention includes an ErA variant exhibiting a Km for Asn in the range of 10 to 250 µM, 20 to 200 µM, 30 to 190 µM, or 50 to 150 µM.

To increase the in vivo circulation time of L-asparaginases disclosed herein (including wild-type asparaginases and fusion proteins), this invention also provides the variants, in particular ErA variants, having a histidine tag (His), a SUMO tag (SUMO), an albumin-binding domain (ABD), or a combination thereof. The L-asparaginase variant can include the histidine tag, SUMO tag and/or an albumin-binding domain at its C-terminus and/or N-terminus. By way of illustration, the L-asparaginase variant can have the N→C-terminal structure of SUMO-Asparaginase-ABD, His-SUMO-ABD-Asparaginase, His-SUMO-Asparaginase-ABD, His-SUMO-Asparaginase, His-ABD-Asparaginase, ABD-Asparaginase, ABD-SUMO-Asparaginase, and the like. Nucleic acids encoding the His, SUMO or ABD can be inserted in-frame either 5' or 3' of the nucleic acids encoding the L-asparaginase thereby creating a fusion protein.

Ideally, the inclusion of one or more of a histidine tag, a SUMO tag, an albumin-binding domain, or a combination thereof significantly increases the in vivo circulation time of an L-asparaginase. Alternatively stated, the variant has a longer than wild-type L-asparaginase administered at an equivalent protein dose. As used herein, the term "t½" or "half life" refers to the time that would be required for the concentration of an L-asparaginase or a variant or fusion protein thereof to fall by half in vitro or in vivo, for example, after injection in a mammal. In particular, the variant has a t½ of at least about 50, 52, 54, 56, 58, 59, 60, 61, 62, 63, 64, or hours at a dose of about 50 µg/kg (protein content basis). Alternatively, the variant has a of at least about 30, 32, 34, 36, 37, 38, 39, or 40 hours at a dose of about 10 µg/kg (protein content basis). In another embodiment, the variant has a t½ of at least about 100 to about 200 hours at a dose ranging from about 10,000 to about 15,000 IU/m$^2$ (about 20-30 mg protein/m$^2$). Given that efficacy of L-asparaginases is related to the in vivo half-life of the drug, the variants of this invention are particularly useful in the treatment of cancers, such as leukemias and lymphomas.

As used herein, a "histidine tag" refers to an amino acid motif composed of at least six histidine (His) residues. The histidine tag includes a polyhistidine of 6 (hexa histidine tag, 6×His tag, or His$_6$ tag), 7, 8, 9, 10, or up to 20 histidine residues.

A "SUMO tag" refers to the fusion of a SUMO (small ubiquitin-related modifier) protein to a protein of interest to enhance the solubility/stability of the protein of interest. The inclusion of a SUMO tag can be achieved using known expression systems such as the CHAMPION pET SUMO expression system (Invitrogen), the EXPRESSO T7 SUMO cloning and expression system (Lucigen), or pET His6 SUMO TEV LIC cloning vector (Addgene). In addition to SUMO tag, it is contemplated that other Ubl proteins can be used including, but not limited to, Ub, Rub1, Hub1, ISG15, Ubi-L (MNSF), FAT10, Apg12, Apg8 and Urm1 (Larsen & Wang (2002) *J. Proteome Res.* 1(5):411-9). See also U.S. Pat. No. 7,655,413, incorporated herein by reference in its entirety.

An "albumin-binding domain" refers to a polypeptide that binds albumin in vivo or in vitro and enhances the serum half-life and biodistribution of a therapeutic agent. Albumin may be derived from any animal species, for example human, monkey, or rodent. Albumin-binding domains are described, for example, in U.S. Pat. No. 6,267,964, WO 1991/19741, WO 2005/097202, WO 2001/45746, WO 2013/043071 and US 2004/0001827. Further, U.S. Pat. No. 9,156,887 discloses non-natural albumin-binding domains, which may be used in this invention. In some embodiments, the albumin-binding domain has the amino acid sequence set forth in SEQ ID NO:13, SEQ ID NO:14 or SEQ ID NO:15.

PEGylation of the L-asparaginases disclosed herein (including wild-type L-asparaginases, ErA variants and fusion proteins) can also be used to increase in vivo circulation time. The term "PEGylated" or "PEGylation" refers to conjugation of an L-asparaginase with polyethylene glycol (PEG). PEG can be coupled (e.g., covalently linked) to active agents through the hydroxy groups at the end of the PEG chain via chemical methods. Methods of PEGylation that can be used to PEGylate an L-asparaginase of the invention are provided, for example, in U.S. Pat. Nos. 4,179,337, 5,766,897, US 2002/0065397, and US 2009/0054590. Alternatively, as disclosed herein, an L-asparaginase can be PEGylated by site-specific PEGylation of between 1 and 5 cysteine residues introduced into the amino acid sequence of the L-asparaginase by amino acid substitution. See Example 6. In some embodiments, the L-asparaginase is an L-asparaginase from *E. chrysanthemi* (wild-type, variant or fusion protein) having a cysteine residue at position 72, 76, 79, 84, 85, 206, 210, 215, 216, 235, 239, 240, 261, 264, 265, 268, 269, 318, 322, or a combination thereof. In particular embodiments, PEGylation of a L-asparaginase of this invention is achieved by replacing Asp84 of a wild-type L-asparaginase (e.g., ErA of SEQ ID NO:1), a variant L-asparaginase (e.g., variants of SEQ ID NO:2, SEQ ID NO:3, SEQ ID NO:4, SEQ ID NO:5, SEQ ID NO:6 or SEQ ID NO:7) or a fusion protein thereof with cysteine thereby providing a specific site for maleimide-based PEGylation of the L-asparaginase.

Enhanced cytotoxic activity of the L-asparaginases disclosed herein (i.e., wild-type and Era variants) can be achieved by conjugating or fusing the L-asparaginase to three tandem soluble domains of TRAIL or co-administering the L-asparaginase with a stable form of TRAIL. As demonstrated herein, the resulting fusion protein was found to provide at least a 25-fold decrease in IC$_{50}$ value compared to an L-asparaginase lacking the three tandem soluble domains of TRAIL. Accordingly, a fusion protein disclosed herein is particularly useful in the treatment of cancer, in particular, L-asparaginase-insensitive cancers.

A "fusion protein" refers to a chimeric protein containing proteins or protein fragments (e.g., L-asparaginase or variants thereof) operably linked in a non-native way. In accordance with the fusion protein of this invention, three tandem soluble domains of TRAIL (TRAIL$_{trimer}$) are fused, in-frame, with an L-asparaginase (e.g., an *Erwinia chrysanthemi* or *Escherichia coli* L-asparaginase), or variant thereof (e.g. an ErA variant). The fusion protein can include TRAIL at its C-terminus or N-terminus. By way of illustration, the fusion protein can have the N→C-terminal structure of TRAIL-Asparaginase or Asparaginase-TRAIL. When used in combination with a tag or modification, the fusion protein can have the structure of: SUMO-TRAIL-Asparaginase-ABD, His-SUMO-ABD-TRAIL-Asparaginase, His-SUMO-TRAIL-Asparaginase-ABD, His-SUMO-Asparaginase-TRAIL, His-ABD-TRAIL-Asparaginase, ABD-Asparaginase-TRAIL, ABD-SUMO-TRAIL-Asparaginase, and the like. Nucleic acids encoding TRAIL in particular TRAIL$_{trimer}$ can be inserted in-frame either 5' or 3' of the nucleic acids encoding the L-asparaginase thereby creating the fusion protein.

Preferably, the soluble domains of TRAIL are derived from a mammalian, particularly human TRAIL including allelic variants and/or derivatives thereof. The soluble domains include the extracellular portion of TRAIL including the receptor binding domain without membrane localized domains. Like other proteins of the TNF superfamily, TRAIL is anchored to the membrane via an N-terminal portion of 15-30 amino acids, the so-called stalk-region. The stalk region contributes to trimerization and provides a certain distance to the cell membrane. However, the stalk region is not part of the receptor binding domain (RBD). Accordingly, it is preferred that the soluble TRAIL domains include the receptor binding domain of the TRAIL lacking any amino acids from the stalk region (see US 2015/0337027).

The soluble TRAIL domain may be derived from human TRAIL as set forth in SEQ ID NO:16. Preferably, the soluble TRAIL domains are derived from human TRAIL, particularly starting from amino acids 115-122, and include amino acid residues 115-281, 120-281, 121-281 or 122-281 of SEQ ID NO:16. In certain embodiments, each of the soluble domains of TRAIL$_{trimer}$ are composed of residues 115-281 of human TRAIL (SEQ ID NO:16). Residues 115-281 of human TRAIL are set forth herein in SEQ ID NO:17.

Derivatives and variants of the death receptor binding TRAIL domains are all contemplated and can be made by altering their amino acid sequences by substitutions, additions, and/or deletions/truncations or by introducing chemical modifications that result in functionally equivalent polypeptides. It will be understood by one of ordinary skill in the art that certain amino acids in a sequence of any polypeptide may be substituted for other amino acids without adversely affecting the activity of the polypeptides.

The TRAIL domains disclosed herein include substitutions of one or more of the amino acids in the disclosed sequences. A skilled artisan will be able to determine using well-known techniques suitable sequence variants of the peptides set forth herein. In certain embodiments, one skilled in the art may identify suitable areas of the molecule that may be changed without destroying activity by targeting regions not believed to be important for activity. In other embodiments, the skilled artisan can identify residues and portions of the molecules that are conserved among similar polypeptides. In further embodiments, even amino acid residues important for biological activity or for structure may be subject to conservative amino acid substitutions without destroying the biological activity thereof or without adversely affecting the peptide structure.

The three soluble domains of TRAIL are preferably linked to one another via peptide linking group composed of one to eight amino acid residues. Likewise, it is preferable that $TRAIL_{trimer}$ is linked to the L-asparaginase via a peptide linking group composed of one to twenty amino acid residues. The term "peptide linking group" or "linker" is meant to refer to a peptide moiety that acts as a molecular bridge to operably link two different molecules together. Desirably, the linkers of this invention are composed of glycine or serine, or a combination thereof. In particular embodiments, each of the soluble domains of $TRAIL_{trimer}$ are preferably linked to one another by a single glycine or single serine residue. An exemplary $TRAIL_{trimer}$ including a single glycine residue between the three soluble TRAIL domains is set forth herein in SEQ ID NO:18. Regarding the peptide linking group located between the $TRAIL_{trimer}$ and L-asparaginase, it is desirable that this linker is a flexible linker. The flexible linker preferably has a length of one to 20 amino acid residues, particularly a length of 6, 9, 12, 15 or 18 amino residues. The flexible linker is preferably a glycine/serine linker, i.e., a peptide linker composed primarily of the amino acids glycine and serine. In a particular embodiment, the linker between the $TRAIL_{trimer}$ and L-asparaginase is a $(GGGS)_n$ linker (SEQ ID NO:19), wherein n is 1 to 4, or a permutation thereof including, e.g., GGGS $(GGGGS)_n$ (SEQ ID NO:20), herein n is 1 to 4. In certain embodiments, the linker between the $TRAIL_{trimer}$ and L-asparaginase has the amino acid sequence set forth in SEQ ID NO:21. An exemplary $TRAIL_{trimer}$-ErA variant (TM2) fusion protein having a $TRAIL_{trimer}$ including a single glycine residue between the three soluble TRAIL domains and a glycine/serine linker between the $TRAIL_{trimer}$ and L-asparaginase is set forth herein in SEQ ID NO:22.

A stable form of TRAIL is intended to refer to a form of TRAIL that promotes trimerization. In particular, to promote trimerization of TRAIL, the FOLDON sequence (GYIPEAPRDGQAYVRKDGEWVLLSTFL; SEQ ID NO:31), a small trimerization domain, has been shown to maintain TRAIL stability and biological activity at 37° C. for at least 48 hours (Kouno, et al. (2013) *J. Invest. Dermatol.* 133(9): 2212-2220). Accordingly, the FOLDON peptide was inserted between a His-SUMO tag and the N-terminus of TRAIL to result in a His-SUMO-FOLDON-TRAIL fusion protein. The fusion protein was expressed and a yield of >10 mg/L of the fusion protein was obtained in the bacterial culture. The protein was very stable, showing that the inclusion of FOLDON results in a stable form of TRAIL. Accordingly, a stable form of TRAIL can be co-administered and/or combined in a pharmaceutical composition with L-asparaginase to enhance cytotoxic activity of the L-asparaginase.

The stable form of TRAIL and TRAIL-asparaginase fusion protein can be further modified to include a histidine tag, a SUMO tag, an albumin-binding domain, PEGylation, or a combination thereof. An exemplary TRAIL-ErA variant (TM2) fusion protein further including a polyhistidine tag and SUMO tag at the N-terminus is set forth herein in SEQ ID NO:23. Further an exemplary stable form of TRAIL can have the structure: His-SUMO-FOLDON-TRAIL.

The variants and fusion proteins disclosed herein can be readily prepared by conventional recombinant protein techniques, wherein recombinant host cells are transformed or transduced with an expression construct or vector harboring a nucleic acid molecule encoding the variant or fusion protein, the recombinant host cells are grown under suitable conditions to provide for expression of the variant or fusion protein, and the variant or fusion protein is subsequently isolated and optionally purified. Accordingly, this invention also provides a nucleic acid molecule encoding an ErA variant (i.e., an ErA with an amino acid substitution at one or more of positions 31, 63 and 254 of SEQ ID NO:1 and/or including a histidine tag, a SUMO tag, an albumin-binding domain, or a combination thereof) or a fusion protein (i.e., an L-asparaginase linked to three tandem soluble domains of TRAIL), as well as a expression cassette and/or expression vector containing the same. Ideally, the expression cassette and expression vector contain the necessary regulatory sequences (e.g., promoter, terminator, and the like) to facilitate expression in the host cell of interest. Host cells including a nucleic acid molecule encoding an ErA variant or fusion protein are also included within the scope of this invention. Host cells can include eukaryotic cells (e.g., mammalian, fungal or yeast cells) or prokaryotic cells (e.g., *E. coli*).

Once produced and isolated/purified, the ErA variant and/or fusion protein of the invention can be used as is or formulated in a pharmaceutical composition containing a pharmaceutically acceptable excipient. Pharmaceutical compositions provided herein can be specially formulated for intravenous administration in solid or liquid form or for intravenous injection. Optimal pharmaceutical compositions can be determined by one skilled in the art depending upon, for example, the intended route of administration, delivery format and desired dosage. See, for example, Remington's Pharmaceutical Sciences (19th edition, 1995).

ErA variant and/or fusion protein can be incorporated in a conventional systemic dosage form, such as an injectable formulation. The dosage forms may also include the necessary physiologically acceptable carrier material, excipient, lubricant, buffer, surfactant, antibacterial, bulking agent (such as mannitol), antioxidants (ascorbic acid or sodium bisulfite) or the like.

The primary carrier or excipient in a pharmaceutical composition may be either aqueous or non-aqueous in nature. For example, a suitable carrier or excipient may be water for injection, physiological saline solution or artificial cerebrospinal fluid, possibly supplemented with other materials common in compositions for parenteral administration. Neutral-buffered saline or saline mixed with serum albumin are further exemplary vehicles. Pharmaceutical compositions can include Tris buffer of about pH 7.0-8.5, or acetate buffer of about pH 4.0-5.5, which may further include sorbitol or a suitable substitute therefor. Pharmaceutical compositions of the invention may be prepared for storage by mixing the selected composition having the desired degree of purity with optional formulation agents (Remington's Pharmaceutical Sciences, Id.) in the form of a lyophilized cake or an aqueous solution. Further, the ErA variant or fusion protein of the invention may be formulated as a lyophilizate using appropriate excipients such as sucrose or glycine.

Administration routes for the ErA variant, fusion protein, or pharmaceutical compositions of the invention include injection by intravenous, intraperitoneal, intracerebral (intra-parenchymal), intracerebroventricular, intramuscular, intra-ocular, intraarterial, intraportal, or intralesional routes;

by sustained release systems or by implantation devices. Compositions may be administered by bolus injection or continuously by infusion, or by implantation device. Compositions also can be administered locally via implantation of a membrane, sponge or another appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

The compositions of the invention can be delivered parenterally. When parenteral administration is contemplated, the therapeutic compositions for use in this invention may be in the form of a pyrogen-free, parenterally acceptable aqueous solution comprising the desired compound identified in a screening method of the invention in a pharmaceutically acceptable vehicle. A particularly suitable vehicle for parenteral injection is sterile distilled water in which the compound identified in a screening method of the invention is formulated as a sterile, isotonic solution, appropriately preserved. Preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which may then be delivered via a depot injection. Formulation with hyaluronic acid has the effect of promoting sustained duration in the circulation. Implantable drug delivery devices may be used to introduce the desired molecule.

The compositions may also be formulated for inhalation. In these embodiments, the ErA variant or fusion protein is formulated as a dry powder for inhalation, or inhalation solutions may also be formulated with a propellant for aerosol delivery, such as by nebulization. Pulmonary administration is further described in WO 1994/020069, which describes pulmonary delivery of chemically modified proteins.

The compositions of the invention can be delivered through the digestive tract, such as orally. The preparation of such pharmaceutically acceptable compositions is within the skill of the art. The ErA variant or fusion protein of the invention that is administered in this fashion may be formulated with or without those carriers customarily used in the compounding of solid dosage forms such as tablets and capsules. A capsule may be designed to release the active portion of the formulation at the point in the gastrointestinal tract when bioavailability is maximized and pre-systemic degradation is minimized. Additional agents can be included to facilitate absorption of the peptides of the invention disclosed herein. Diluents, flavorings, low melting point waxes, vegetable oils, lubricants, suspending agents, tablet disintegrating agents, and binders may also be employed.

These compositions may also contain adjuvants such as preservative, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

The ErA variant and/or fusion protein of the invention find particular use in the treatment of a disease or condition treatable by depletion of asparagine. Accordingly, this invention also provides methods for treating a disease, in particular cancer, by administering to a subject in need of treatment and effective amount of a ErA variant or fusion protein. An "effective amount" is used herein to refer to an amount of an active ingredient sufficient to achieve the intended purpose of (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); (e) limiting or preventing recurrence of symptoms in patients that were previously symptomatic for the disorder(s); (f) reduction of mortality after occurrence of a disease or a disorder; (g) healing; and (h) prophylaxis of a disease. The effective amount in each individual case may be determined empirically by a skilled artisan according to established methods in the art. As used in the context of the invention, "administering" includes in vivo administration to an individual as well as administration directly to cells or tissue in vitro or ex vivo. An effective amount of an ErA variant or fusion protein is generally that which can induce apoptosis and reduce circulating L-asparagine in cancer cells or a tumor of the subject. A clinician may titer the dosage or route of administration to obtain the optimal therapeutic effect.

In certain embodiments, the ErA variant or fusion protein is useful in the treatment or the manufacture of a medicament for use in the treatment of acute lymphoblastic Leukemia (ALL) in both adults and children, as well as other conditions where asparagine depletion is expected to have a useful effect. Such conditions include, but are not limited to, malignancies or cancers, including but not limited to hematalogic malignancies, non-Hodgkin's lymphoma, NK lymphoma, pancreatic cancer, Hodgkin's disease, acute myelocytic Leukemia, acute myelomonocytic Leukemia, chronic lymphocytic Leukemia, lymphosarcoma, reticulosarcoma, and melanosarcoma. Representative non-malignant hematologic diseases which respond to asparagine depletion include immune system-mediated Blood diseases, e.g., infectious diseases such as those caused by HIV infection (i.e., AIDS). Non-hematologic diseases associated with asparagine dependence include autoimmune diseases, for example rheumatoid arthritis, SLE, autoimmune, collagen vascular diseases, AIDS, etc. Other autoimmune diseases include osteo-arthritis, Issac's syndrome, psoriasis, insulin dependent diabetes mellitus, multiple sclerosis, sclerosing panencephalitis, systemic lupus erythematosus, rheumatic fever, inflammatory bowel disease (e.g., ulcerative colitis and Crohn's disease), primary billiary cirrhosis, chronic active hepatitis, glomerulonephritis, myasthenia gravis, pemphigus vulgaris, and Graves' disease. In particular embodiments, the ErA variant or fusion protein is used in the treatment of non-Hodgkin's lymphoma, leukemia, acute lymphoblastic leukemia, acute myeloid leukemia, B cell lymphoma, Burkitt's lymphoma, chronic myelocytic leukemia, chronic lymphocytic leukemia, and hairy cell leukemia.

Cells suspected of causing disease can be tested for asparagine dependence in any suitable in vitro or in vivo assay, e.g., an in vitro assay wherein the growth medium lacks asparagine. Thus, in one aspect, the invention is directed to a method of treating a disease treatable in a patient, the method comprising administering to the patient an effective amount of a conjugate of the invention. In a specific embodiment, the disease is ALL. In a particular embodiment, the ErA variant or fusion protein used in the treatment of a disease treatable by asparagine depletion includes an L-asparaginase from *Erwinia* species, more specifically *Erwinia chrysanthemi*.

The ErA variant or fusion protein can be administered on a schedule ranging from about 3-times a week to about once a month, typically once per week or once every other week, as a single agent (e.g., monotherapy) or as part of a combination of chemotherapy drugs, including, but not limited to glucocorticoids, corticosteroids, anticancer compounds or other agents, including, but not limited to methotrexate, dexamethasone, prednisone, prednisolone, vincristine, cyclophosphamide, and anthracycline. As an example, patients with ALL will be administered the ErA variant or fusion protein of the invention as a component of multi-agent chemotherapy during 3 chemotherapy phases including induction, consolidation or intensification, and maintenance. In a specific example, the ErA variant or fusion protein is not administered with an asparagine synthetase inhibitor (e.g., see WO 2007/103290). In another specific example, the ErA variant or fusion protein is not administered with an asparagine synthetase inhibitor, but is administered with other chemotherapy drugs. The ErA variant or fusion protein can be administered before, after, or simultaneously with other compounds as part of a multi-agent chemotherapy regimen.

In a specific embodiment, the method involves administering an ErA variant or fusion protein of the invention at an amount of about 1 U/kg to about 1000 U/kg. In a more specific embodiment, the ErA variant or fusion protein is administered at an amount selected from the group consisting of about 20, 50, 60, 70, 100, 200, 300, 400, 500 and 600 U/kg. In another specific embodiment, the ErA variant or fusion protein is administered at a dose ranging from about 1000 IU/m$^2$ to about 20000 IU/m$^2$ (e.g., 1000 IU/m$^2$, 2000 IU/m$^2$, 3000 IU/m$^2$, 4000 IU/m$^2$, 5000 IU/m$^2$, 6000 IU/m$^2$, 7000 IU/m$^2$, 8000 IU/m$^2$, 9000 IU/m$^2$, 10000 IU/m$^2$, 11000 IU/m$^2$, 12000 IU/m$^2$, 13000 IU/m$^2$, 14000 IU/m$^2$, 15000 IU/m$^2$, 16000 IU/m$^2$, 17000 IU/m$^2$, 18000 IU/m$^2$, 19000 IU/m$^2$, or 20000 IU/m$^2$). In another specific embodiment, the ErA variant or fusion protein is administered at a dose that depletes Asn to undetectable levels for a period of about 3 days to about 10 days (e.g., 3, 4, 5, 6, 7, 8, 9, or 10 days) for a single dose. In another embodiment, the method involves administering a ErA variant or fusion protein of the invention that has a longer in vivo circulating half-life after a single dose compared to the wild-type L-asparaginase.

The following non-limiting examples are provided to further illustrate the present invention.

Example 1: Materials and Methods

ErA Gene Cloning and Mutagenesis.

A codon-optimized synthetic gene corresponding to the amino acid sequence of ErA (UniProt entry P06608) lacking the first 21-amino acid residue signal peptide was synthesized by Genscript as previously described (Schalk, et al. (2014) *J. Biol. Chem.* 289:33175-33186). The synthetic gene was digested with NdeI and BamHI-HF restriction enzymes, gel purified, and ligated into a His$_6$-SUMO-pET14b vector (where the His$_6$ tag is followed by the yeast protein SUMO (small ubiquitin modifier, Smt3p) using Instant Sticky End DNA ligase (New England Biolabs), generating His$_6$-SUMO-ErA-WT plasmid. This plasmid was subsequently used as template to create the following 13 ErA single-mutant variants: Ala31Ser (A31S), Ala31Ile (A31I), Ala31Leu (A31L), Ala31Met (A31M), Ala31Asn (A31N), Ala31Thr (A31T), Ala31Val (A31V), Glu63Leu (E63L), Glu63Gln (E63Q), Pro123Ser (P123S), Pro123Asn (P123N), Ser254Asn (S254N), Ser254Pro (S254P). The plasmid carrying the mutant E63Q was then used as template to create ErA double-mutant variants (A31T-E63Q, A31I-E63Q, S254N-E63Q and S254Q-E63Q) while the mutant S254N was used to generate two other double-mutants (A31I-S254N and A31T-S254N). The plasmid carrying the double mutation A31I-E63Q was used as template to create two triple mutants A31I-E63Q-S254N and A31I-E63Q-S254Q.

ErA Protein Expression and Purification.

Protein expression and purification were performed as previously described (Schalk, et al. (2014) *J. Biol. Chem.* 289:33175-33186). In brief, plasmids corresponding to wild-type ErA (ErA-WT) or mutated insert (verified by sequencing) were transformed into *E. coli* BL21(DE3) C41 cells for expression. A single colony was picked and expanded at 37° C. in 2×YT medium. Protein expression was induced with 0.3 mM Isopropyl β-D-1-thiogalactopyranoside (IPTG) when the culture reached an optical density (at 600 nm) of 0.6-0.8. The incubation temperature was then reduced and maintained at 18° C. for the next 12 hours. The cells were disrupted by sonication and the debris was cleared by centrifugation at 20,000 g at 4° C. for 30 minutes. The supernatant was loaded onto a 5 mL HISTRAP nickel affinity column (GE Healthcare). The column was subsequently washed with buffers composed of 25 mM Tris-HCl, pH 8.5, 500 mM NaCl, and 25, 50 and 75 mM imidazole. The bound protein was eluted with the same buffer but containing 500 mM imidazole. The N-terminal His$_6$-SUMO tag was cleaved with SUMO protease and the protein solution was loaded back onto a nickel affinity column to separate the tag. The flow-through fraction containing the purified enzyme was dialyzed into 25 mM Tris, pH 8.5, 100 mM NaCl, concentrated to 20-80 mg/ml, aliquoted, flash frozen in liquid nitrogen, and stored at −80° C.

TRAIL Gene Cloning and Mutagenesis.

A synthetic gene (codon-optimized for protein expression in *Escherichia coli*) containing three repeats of human TRAIL (UniProt entry P50591) was synthesized by Genscript. Each repeat included amino acid residues 115 to 281 of TRAIL (SEQ ID NO:17). A single glycine or a single serine residue was inserted between the first and second repeat and second and third repeat. In addition, a 57 bp oligonucleotide (5'-GGC GGT GGC AGC GGT GGA GGA GGC TCT GGT GGA GGC GGT AGC GGA GGC GGA GGG TCG-3'; SEQ ID NO:24), encoding a GGGS (GGGGS)$_3$ linker (SEQ ID NO:21), was added to the end of the repeat third repeat between restriction sites BglIII and NdeI. The resulting gene was inserted into a pUC57 vector.

Using site-directed mutagenesis and the primers Hano-203: 5'-CGA ATG CAT CTA GAT CTC GAG cgt gag cgt g-3' (SEQ ID NO:25) and Hano-204: 5'-cac gct cac gCT CGA GAT CTA GAT GCA TTC G-3' (SEQ ID NO:26), the unique BglIII site of the vector pUC57 containing BglIII-TRAIL$_1$-G-TRAIL$_2$-G-TRAIL$_3$-linker-NdeI was modified to an XhoI site to facilitate sub-cloning. The plasmid obtained was then digested with XhoI and NdeI restriction enzymes, gel-purified to generate the double-digested and purified insert, XhoI-TRAIL$_1$-G/S-TRAIL$_2$-G/S-TRAIl$_3$-linker-NdeI.

The vector His$_6$-SUMO-NdeI-ErA-TM2-pET14b, encoding the ErA A31I-E63Q-S254Q triple mutant (TM2) was amplified using the primers Hano-201: 5'-gaa cag att ggt ggt CTC GAG gga gga att cCA TAT Gga taa act g-3' (SEQ ID NO:27) and Hano-202: 5'-cag ttt atc CAT ATG gaa ttc ctc cCT CGA Gac cac caa tct gtt c-3' (SEQ ID NO:28) thereby creating an XhoI site. The resulting pET14b plasmid containing His$_6$-SUMO-XhoI-NdeI-ErA-TM2 was digested with XhoI and NdeI restriction enzymes and gel-purified to generate the double-digested and purified vector pET14b-His$_6$-SUMO-XhoI-NdeI-ErA-TM2.

The double-digested and purified insert, XhoI-TRAIL$_1$-G/S-TRAIL$_2$-G/S-TRAIL$_3$-linker-NdeI, was ligated into the double-digested and purified vector pET14b-His$_6$-SUMO-XhoI-NdeI-ErA-TM2 using Instant Sticky End DNA ligase (New England BioLabs), generating the pET14b-His$_6$-SUMO-XhoI-TRAIL$_1$-G/S-TRAIL$_2$-G/S-TRAIL$_3$-linker-NdeI-ErA-TM2 plasmid. The correct sequence was confirmed by DNA sequence analysis. Using the primers Hano-211: 5'-gca cgc tat atc acc atg acg aac gct tcg acc-3' (SEQ ID NO:29) and Hano-212: 5'-ggt cga agc gtt cgt cat ggt gat ata gcg tgc-3' (SEQ ID NO:30), this plasmid was used as template to generate the inactive mutant pET14b-His$_6$-SUMO-XhoI-TRAIL$_1$-G-TRAIL$_2$-G-TRAIL$_3$-linker-NdeI-ErA-TM2-K168M.

Fusion Protein Expression and Purification.

The pET14b-His$_6$-SUMO-XhoI-TRAIL$_1$-G/S-TRAIL$_2$-G/S-TRAIL$_3$-linker-NdeI-ErA-TM2 and pET14b-His$_6$-SUMO-XhoI-TRAIL$_1$-G/S-TRAIL$_2$-G/S-TRAIL$_3$-linker-NdeI-ErA-TM2-K168M plasmids were separately transformed into *E. coli* BL21(DE3) C41 cells for expression, wherein the resulting proteins are referred to herein as TRAIL$_{trimer}$-ErA-TM2 and TRAIL$_{trimer}$-ErA-TM2-K168M, respectively. A single colony was picked and grown overnight at 37° C. in 2YT medium. Two protocols were established to express the proteins toward similar high production yield.

In the first protocol, an overnight culture was transferred into fresh 2YT medium and grown at 37° C. until the culture reached an optical density (at 600 nm) of 0.6-0.8. Protein expression was induced with 0.1 mM IPTG for four to five hours at 37° C. before cells were harvested.

In the second protocol, an overnight culture was transferred into fresh ZY medium (1% N—Z-Amine or tryptone plus 0.5% yeast extract) supplemented with 20 mL sterile 50×M (1.25 M Na$_2$HPO$_4$, 1.25 M KH$_2$PO$_4$, 2.5 M NH$_4$Cl and 0.25 M Na$_2$SO$_4$), 20 mL sterile 50×5052 (25% glycerol, 2.5% glucose and 10% α-lactose monohydrate), 1 mL sterile 2 M MgSO$_4$, and 0.1-1 mL sterile 1000× metal mix (50 mM FeCl$_3$×6 H$_2$O; 20 mM CaCl$_2$×2H$_2$O; 10 mM MnCl$_2$; 10 mM ZnSO$_4$×7 H$_2$O; 2 mM CoCl$_2$×6 H$_2$O; 2 mM CuCl$_2$; 2 mM NiCl$_2$×6 H$_2$O; 2 mM Na$_2$MoO$_4$×2 H$_2$O; 2 mM Na$_2$SeO$_3$; 2 mM H$_2$BO$_3$) per 1 L of ZY. The incubation temperature was then reduced and maintained at 20° C. for overnight before cells were harvested.

Cells obtained by the first or second protocol were disrupted by sonication, and the debris was cleared by centrifugation at 20,000 g at 4° C. for 30 minutes. The supernatant was loaded onto a 5-ml HISTRAP nickel affinity column (GE Healthcare). The column was subsequently washed with buffers composed of 25 mM Tris-HCl, pH 8.5, 500 mM NaCl, and either 25, 50, or 75 mM imidazole. The bound protein was eluted with the same buffer but containing 500 mM imidazole. The N-terminal His$_6$-SUMO tag was cleaved by His$_6$-tagged SUMO protease. The flow-through fraction containing the purified enzyme was dialyzed into Dulbecco's phosphate-buffered saline (DPBS, Mediatech). The purity of the fusion proteins of 97 kDa was confirmed by SDS-PAGE.

Kinetic Assays.

L-asparaginase activity was determined using a continuous spectroscopic enzyme-coupled assay as previously described (Schalk, et al. (2014) *J. Biol. Chem.* 289:33175-33186). In brief, the assay measures the production of L-aspartate through the 1:1 oxidation of reduced NADH. The conversion of NADH to NAD$^+$ was measured spectrophotometrically as a decrease in absorbance at 340 nm at 37° C. All measurements were taken in triplicate. Rates were fit to the Michaelis-Menten equation using SIGMAPLOT software (Systat Software Inc). Notably, the fusion protein TRAIL$_{trimer}$-ErA-TM2 had a specific activity of ~10 International Units (IU) per mg; while the inactive fusion protein TRAIL$_{trimer}$-ErA-TM2-K168M had only <0.2 IU per mg.

A conventional assay for determining L-glutaminase activity (Gella & Pascual (1982) *Anal. Biochem.* 127:322-5) was used with some modifications. The purified enzyme was mixed into a solution containing 50 mM Tris-HCl pH 8.5, 1 mg/mL BSA, 7 U GDH (Glutamate dehydrogenase, Sigma-Aldrich), 3 mM INT (Iodonitrotetrazolium chloride, Sigma-Aldrich), 100 mM PMS (Phenazine methosulfate, Sigma-Aldrich), and 100 mM NAD+. Adding different concentrations of L-glutamine triggered the first reaction to produce ammonia and L-glutamic acid. The latter, in the presence of NAD+ and under the catalysis of GDH, is broken further into α-ketoglutarate and ammonia. NADH produced by this second reaction, together with INT serve as inputs to the third reaction, where the formation of INT-formazan under the catalysis of PMS can be followed spectrophotometrically as an increase in absorbance at 500 nm. All reactions were carried out at 37° C. 1 IU of enzyme is defined as the amount of enzyme used to produce 1 μmole of product in 1 minute at 37° C.

Cultivation of Cells.

The LOUCY cell line was verified to be *mycoplasma* free and confirmed to match 100% to corresponding STR (Short Tandem Repeat) profile data from the Global Bioresource Center ATCC. Cells were cultivated in a humid atmosphere (5% CO$_2$, 37° C.) using RPMI 1640 media supplemented with 10% FBS (Hyclone) and 1× penicillin-streptomycin solution (Invitrogen). L-Glutamine was added directly into cell cultures to a final concentration of 2 mM.

Cell Viability-Proliferation Assay.

Ninety μL aliquots of cell suspension (2.5×10$^5$ cells per mL) were cultured in triplicate in round-bottomed 96-well microtiter plates in the presence of 10 μL of either DPBS (Dulbecco's phosphate-buffered saline, Mediatech) or L-asparaginases to a final concentration ranging from 0.0001 to 1 IU/mL. After incubating the plates for 4 days at 37° C. in humidified air containing 5% CO$_2$, Alamar Blue (Invitrogen) was added to a final concentration of 10% v/v and the plates were incubated for an additional four hours, followed by reading of the fluorescence signal. The leukemic cell viability was calculated as percentage of fluorescence counts in the presence of L-asparaginase versus that in the DPBS control.

Crystallization, X-Ray Data Collection, and Refinement.

Crystals of the ErA mutants were grown at 285 K using the hanging-drop vapor-diffusion method. Two μL of enzyme at 2.5-10 mg/mL were mixed with 1-4 μL of reservoir buffer solution. The reservoir solution was composed of 0.1M HEPES, pH 7.5 and 24% of PEG MME 2000.

Prior to data collection, crystals were soaked for 5 minutes with 10 mM L-aspartic acid (Sigma-Aldrich) or 25 mM L-glutamic acid (Sigma-Aldrich) in 0.1 M HEPES, pH 7.5 and 24% of PEG MME 2000. Soaked crystals were then transferred to the same solutions respectively but supplemented with 25% of glycerol for cryoprotection.

Diffraction data were collected on the Life Sciences Collaborative Access Team (LS-CAT) beamline 21-ID-F located at Argonne National Laboratory. Data were processed with the XDS package (Kabsch (2010) *Acta Crys-* tallogr. D Biol. Crystallogr. 66:133-144). Structures were determined by molecular replacement with MOLREP (Roberts (1976) *J. Biol. Chem.* 251:2119-2123) using the atomic resolution structure (PDB entry 1O7J) as a search model. Refinement was conducted using REFMAC (Steckel, et al. (1983) *Biochem. Pharmacol.* 32:971-977) and model building was conducted using Coot (Steckel, et al. (1983) *Biochem. Pharmacol.* 32:971-977). Data collection and refinement statistics are listed in Table 1. Structures were prepared using the PyMOL Molecular Graphics System (version 1.6.0, Schrödinger).

Inspection of the electron density showed the presence of the soaked Asp at the active site. In contrast, electron density for the soaked Glu was not observed.

Example 2: High L-Glutaminase Co-Activity is not Required for In Vivo Efficacy of L-Asparaginases Design and Characterization of ErA Variants with High L-Asparaginase and Low L-Glutaminase Activities.

It was posited that for an L-asparaginase to be a successful in treating ALL, the enzyme needs as high as possible L-asparaginase activity (to kill the cancer cells), but as low as possible L-glutaminase activity (to minimize toxic side effects). Of the two FDA-approved bacterial L-asparaginases, the one from *E. chrysanthemi* (ErA) has a higher L-asparaginase activity than that from *E. coli* (EcA). See Table 2.

TABLE 1

| Structure | E63Q + Asp | ErA-A31I-E63Q + Asp | ErA-E63Q-S254Q + Asp |
|---|---|---|---|
| PDB codes | 5I3Z | 5I3Z | 5I3Z |
| Data collection statistics | | | |
| X-ray source and detector | LS-CAT ID-D MARCCD 300 | LS-CAT ID-F MARCCD 225 | LS-CAT ID-D MARCCD 300 |
| Wavelength (Å) | 1.008264 | 0.97872 | 1.008264 |
| Temperature (K) | 100 | 100 | 100 |
| Resolution$^a$ (Å) | 1.008264 | 1.008264 | 1.60 (1.69-1.60) |
| No. of Reflections | | | |
| Observed | 437716 (49641) | 1278167 (118300) | 682869 (105570) |
| Unique | 74069 (10093) | 183230 (23339) | 122786 (19113) |
| Completeness (%) | 97.2 (83.5) | 95.7 (76.2) | 98.2 (95.7) |
| $R_{sym}$ (%) | 12.6 (53.7) | 5.5 (60.8) | 10.1 (61.6) |
| Average I/σ(I) | 16.88 (4.08) | 23.09 (3.01) | 14.71 (3.36) |
| Space group | $P2_12_12_1$ | $P2_12_12_1$ | I222 |
| Unit cell (Å): a, b, c | 77.89, 87.89, 175.99 | 77.19, 87.69, 175.11 | 76.98, 123.12, 198.44 |
| Wilson B-factors (Å2) | 16.5 | 16.6 | 17.1 |
| Refinement statistics | | | |
| Refinement program | REFMAC5 | REFMAC5 | REFMAC5 |
| $R_{cryst}$ (%) | 17.39 | 12.02 | 15.43 |
| $R_{free}$ (%) | 20.93 | 17.06 | 18.28 |
| Resolution range (Å) | 30.00-2.05 | 30.0-1.5 | 30.0-1.6 |
| Protein molecules per a.u. | 4 | 4 | 3 |
| No. of atoms: | | | |
| Protein$^b$ | 2455, 2455, 2464, 2463 | 2487, 2481, 2466, 2487 | 2521, 2499, 2503 |
| H$_2$O molecules | 976 | 1004 | 954 |
| Asp molecules | 4 | 4 | 3 |
| R.m.s. deviation from ideal: | | | |
| Bond length (Å) | 0.0135 | 0.0226 | 0.0193 |
| Bond angles (°) | 1.5853 | 1.9611 | 1.9204 |
| Average B-factors (Å2) | 21.0 | 20.0 | 16.0 |
| Protein$^b$ | 22.1, 20.0, 19.9, 20.4 | 18.7, 19.9, 21.4, 19.4 | 14.9, 15.1, 16.5 |
| Water molecules | 27.4 | 30.9 | 26.7 |
| Asp molecules | 21.3, 22.6, 18.8, 22.1 | 17.5 | 16.3, 16.6, 16.4 |
| Most favored regions | 96.81 | 96.67 | 97.38 |
| Additionally allowed regions | 2.88 | 3.01 | 2.29 |
| Outlier regions | 0.31 | 0.32 | 0.33 |

$^a$High resolution shell in parenthesis.
$^b$ProtA, protB, protC, protD.

TABLE 2

| Enzyme Name | $k_{cat}$ (sec$^{-1}$) | Km (μM) | $k_{cat}$/Km (sec$^{-1}$μM$^{-1}$) | $k_{obs}$@50 μM (sec$^{-1}$) |
|---|---|---|---|---|
| ErA-WT | 194.9 ± 2.5 | 44.2 ± 1.6 | 4.41 | 105.3 |
| ErA-E63Q-S254Q (DM3) | 147.3 ± 1.0 | 179.1 ± 5.6 | 0.82 | 36.3 |
| ErA-E63Q | 179.9 ± 1.4 | 48.1 ± 1.1 | 3.74 | 92.2 |
| EcA-WT | 44.4 ± 0.3 | 15.0 ± 0.5 | 2.96 | 41.3 |

The parameters that define the asparagine-depleting power of such enzyme drugs are of significance. The rate of the reaction ($k_{cat}$) is important (a slow enzyme would be inefficient at depleting the Asn), but probably more critical is the Km value. To achieve the required low micromolar concentration of blood Asn, the enzyme must have a Km value in this range. Enzymologists often combine these two parameters into a single value ($k_{cat}$/Km) that is thought to represent the efficiency of the enzyme. Since human blood contains about 50 μM Asn, the rate of Asn hydrolysis by the enzyme at this exact substrate concentration is also a parameter that informs on the clinical suitability of an L-asparaginase. Table 2 presents these values for the FDA-approved wild-type ErA and EcA (i.e., ErA-WT and EcA-WT). These numbers show that ErA-WT is ~2-fold better than EcA-WT in hydrolyzing Asn under physiological concentration of Asn. Therefore, the ErA enzyme was selected for developing a variant with low L-glutaminase activity.

In addition to superior L-asparaginase activity, ErA-WT also has higher L-glutaminase activity (Table 3).

TABLE 3

| Enzyme Name | $k_{cat}$ (sec$^{-1}$) | $K_m$ (mM) | $k_{cat}$/$K_m$ (sec$^{-1}$mM$^{-1}$) | $k_{obs}$@ 50 mM (sec$^{-1}$) |
|---|---|---|---|---|
| ErA-WT | 26.84 ± 0.26 | 0.36 ± 0.02 | 74.56 | 15.87 |
| ErA-E63Q-S254Q (DM3) | 2.93 ± 0.03 | 15.8 ± 0.3 | 0.19 | 0.11 |
| ErA-E63Q | 8.33 ± 0.16 | 3.86 ± 0.23 | 3.68 | 0.74 |
| EcA-WT | 0.89 ± 0.01 | 1.38 ± 0.09 | 0.64 | 0.22 |

Wild-type ErA has >70-fold higher L-glutaminase activity compared to EcA-WT at the physiological concentration of 0.5 mM Gln. The result of the ErA engineering effort geared at lowering the intrinsic L-glutaminase activity while maintaining its high L-asparaginase activity resulted in several variants that fulfill these criteria, with the top two variants listed in Table 3.

The single mutation of Glu63 to glutamine reduced the L-glutaminase activity by >21-fold. Adding to the E63Q, the Ser254 to asparagine mutation resulted in a double mutant (ErA-DM1) with an additional 7-fold reduction of the L-glutaminase activity. Not only do both ErA mutants have significantly reduced L-glutaminase activity compared to ErA-WT, ErA-DM1 is even lower compared to that of EcA-WT (Table 3). However, the L-asparaginase activity of the ErA-DM1 was reduced to a level similar to that of EcA-WT (see $k_{obs}$ @50 μM Asn, Table 2).

For clinical utility, the relative L-asparaginase to L-glutaminase ratio is of importance. Therefore, this ratio was calculated based on rates observed at physiological substrate concentrations (50 μM for Asn, 500 μM for Gln) and on IUs (clinically, L-asparaginases are dosed based on International Units). Both ratios show that ErA-DM2 is a superior enzyme relative to ErA-WT (Table 4). Notably, even when compared to EcA-WT, an enzyme with an intrinsically low L-glutaminase activity, ErA-DM1 showed a lower L-glutaminase activity. This point was validated using NMR spectroscopy, which was used to follow the L-glutaminase rate of the enzymes listed in Table 4.

TABLE 4

| Enzyme Name | $K_{obs}$ [Asn$_{phs}$]/ $K_{obs}$ [Gln$_{phs}$] | Specific Activity (Asn)/ Specific Activity (Gln) |
|---|---|---|
| ErA-WT | 6.6 | 7.3 |
| ErA-DM1 | 330 | 59.9 |
| ErA-E63Q | 124.6 | 21.6 |
| EcA-WT | 187.7 | 49.9 |

These experiments demonstrate the reduced L-glutaminase rate for the designed ErA mutants, and the exceptionally low L-glutaminase activity of ErA-DM1.

In Vitro Testing of L-Asparaginases.

The dependence on exogenous Asn for growth of mouse leukemia L5178Y cells (Haley, et al. (1961) *Cancer Res.* 21:532-536) has made this cell line a useful model for assessing L-asparaginase activity. Therefore, the activity of the ErA-E63Q mutant as compared to ErA-WT and EcA-WT was assessed using this cell line. It was observed that, under conventional cell culture conditions, all three enzymes were efficient at preventing the proliferation of these cells (Table 5).

TABLE 5

| Enzyme Name | IC$_{50}$ (IU/mL) -Gln | IC$_{50}$ (IU/mL) +Gln | Fold Increase |
|---|---|---|---|
| ErA-WT | 0.0036 | 0.0538 | 14.94 |
| ErA-E63Q | 0.0223 | 0.4259 | 19.10 |
| EcA-WT | 0.0174 | 0.4114 | 23.64 |

Using the IC$_{50}$ value as an indicator for the cell killing power of the enzymes, ErA-WT was more efficient (i.e., lower IC$_{50}$ value) than EcA-WT or ETA-63Q. Since this order mirrors the relative L-glutaminase activity of these enzymes (ErA-WT>EcA-WT>ErA-63Q), it was surmised that this difference in IC$_{50}$ was largely due to this side activity of the enzymes. To test this, the dose response experiment was repeated, but this time the cell culture medium was supplemented with Gln. Indeed, the IC$_{50}$ values increased (Table 5). The effect of Gln supplementation on the observed IC$_{50}$ values was dramatic, ranging from a ~15-25-fold increase (Table 5). It was noted that the enzyme with the lowest L-glutaminase side activity was the best protected by Gln supplementation. Said differently, enzymes with high L-glutaminase activity (e.g., ErA-WT) overcome Gln supplementation to a larger degree compared to enzymes with decreased L-glutaminase activity (e.g., ErA-e63Q). This is presumably due to high L-glutaminase activity enzymes hydrolyzing the additional Gln.

Previous work addressing the role of the L-glutaminase side activity of L-asparaginases has relied on cell culture as the experimental model. Since any cell line grown in culture requires Gln, it is apparent that enzymes with high L-glutaminase activity will show better killing. However, this does not necessarily mean that this side activity of L-asparaginase drugs is required for clinical efficacy. In fact, at the extreme case, an enzyme endowed with low L-asparaginase but high L-glutaminase activities will appear in cell culture to be very effective, but will have no clinical relevance in treating cancers such as ALL that depend on exogenous Asn. Accordingly, an in vivo model is preferably used to test the importance of L-glutaminase side activity present in an L-asparaginase.

Development of a Human Xenograft Model of ALL for Assessment of L-Asparaginase Variants.

Past researchers have used the L5178Y murine cell line for in vivo evaluation of L-asparaginases (e.g., Abuchowski, et al. (1984) *Cancer Biochem. Biophys.* 7:175-186; Kwon, et al. (2009) *J. Control Rel.* 139:182-189). Apart from this cell line not being of human origin, an additional disadvantage of this syngeneic ALL mouse model is the inability to quantitatively track the animal's disease burden. This makes it difficult to correctly assess different L-asparaginase preparations. Therefore, a quantitative in vivo model for ALL was developed using luciferase-expressing LOUCY (human T-ALL) and SUP-B15 (human B-ALL) cell lines. The advantage of these systems is the ability to use in vivo imaging, where the bioluminescence signal produced by the implanted luciferase-expressing cells act as a quantitative measure for disease burden.

Initially, the in vitro sensitivity of these human ALL cell lines to the wild-type versions of ErA and EcA, and to the low L-glutaminase ErA variants was determined. This analysis showed that both cell lines were sensitive to L-asparaginase administration. As expected from their higher L-glutaminase activity, the $IC_{50}$ values determined in culture for ErA-WT and EcA-WT were determined to be 50 to 100% lower compared to the low L-glutaminase ErA mutants (Table 6).

TABLE 6

| Enzyme Name | $IC_{50}$ (IU/mL) | |
| --- | --- | --- |
| | LOUCY | SUP-B15 |
| ErA-WT | 0.00033 | 0.00016 |
| ErA-E63Q | 0.00055 | 0.00024 |
| ErA-DM1 | 0.00065 | 0.00031 |
| EcA-WT | 0.00035 | 0.00022 |

After verifying the L-asparaginase sensitivity of the human ALL cell lines, it was confirmed that these cells could be implanted in mice. Based upon an increase in the bioluminescence signal over time, demonstrating the proliferation of the cells and increase in diseases burden.

In Vivo Testing of ErA-WT and ErA Variants in T-ALL and B-ALL Mouse Models.

To test whether the very high intrinsic L-glutaminase activity present in ErA-WT is required for clinical efficacy, mice implanted with LOUCY or SUP-B15 cells were treated with the FDA-approved L-asparaginase and activity was compared to the low L-glutaminase variants described herein. It is important to note that, in addition to enzymatic parameters of the enzymes, other variables can influence the in vivo response. For example, an enzyme with long in vivo stability will be more efficient in depleting blood Asn compared to one with short half-life. In humans, ErA-WT is known to have a much shorter half-life than EcA-WT (0.65 vs 1.24 days; Asselin, et al. (1993) *J. Clin. Oncol.* 11:1780-1786). During the first experiments with ErA-WT, there was no observed decrease in tumor cell growth. It was posited that this was due to the low stability of ErA-WT in the mice, mirroring the observations in humans. To test this, a SUMO tag was added to the N-terminus of ErA-WT to impart increased stability without adversely effecting enzymatic properties. Indeed, mice treated with SUMO-ErA-WT showed a marked decrease in tumor burden. Therefore, all ErA enzymes used in the following in vivo studies contained this stability tag.

Mice implanted with LOUCY T-ALL cells were treated with L-asparaginase daily via intraperitoneal injection (i.p.) for 14 days with a dose of 50 IU/mouse. This dose is equivalent to about ⅓ of the ErA-WT dose given to humans, though in humans it is administered three times a week and is given intramuscularly or intravenously. This difference in administration mode is noted because efficacy in the animal model may be influenced by the amount of drug that makes it into circulation. In other words, while the goal is to test the ability of the L-glutaminase ErA variants to limit cancer growth in vivo, there may be other factors that determine in vivo efficacy. However, since the comparison was between nearly identical enzymes (ErA-WT and ErA mutants), it was assumed that these enzymes would have very similar pharmacokinetic properties.

The high L-glutaminase ErA-WT, the low L-glutaminase ErA-E63Q, and the very low L-glutaminase ErA-DM2 rapidly decreased the number of cancer cells in the animals (FIG. 1A). The slightly slower decrease in luciferase signal observed with ErA-DM1 can be attributed to the higher Asn Km of this mutant. Nevertheless, by treatment end, the level of luciferase signal coming from all ErA variants was close to background, demonstrating very potent killing of these cells.

Figure 1B:
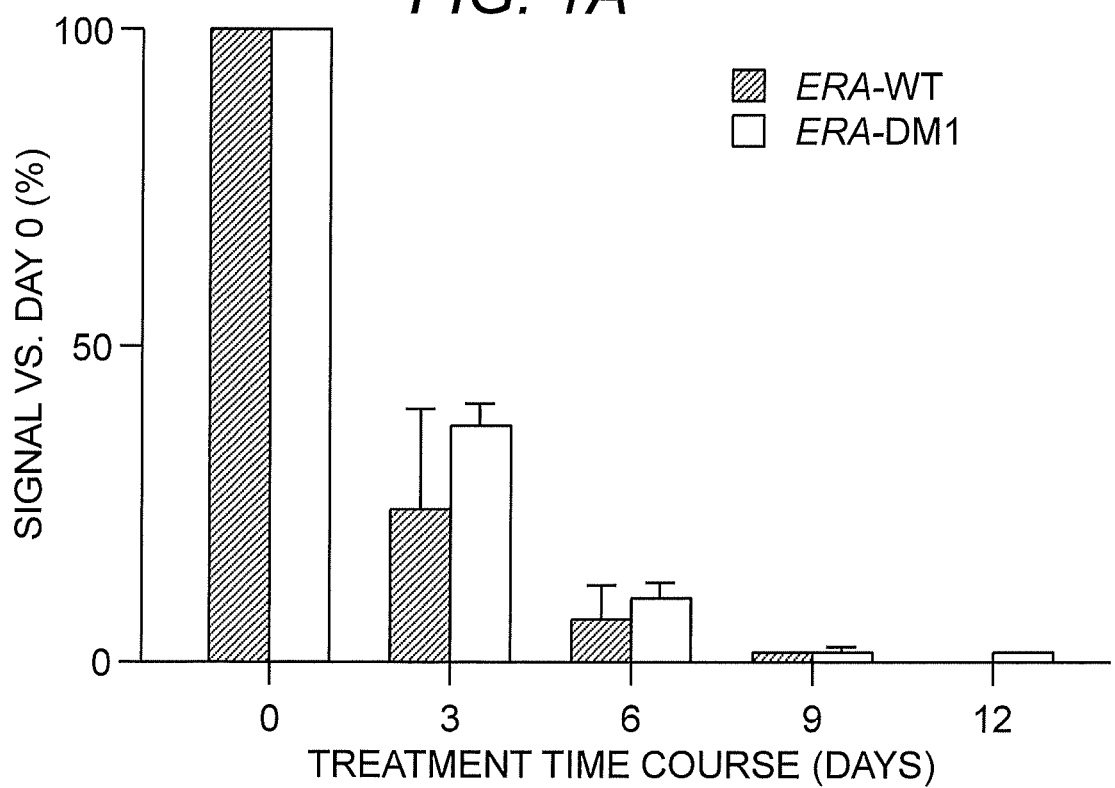

These experiments were repeated with the B-ALL SUP-B15 cell line. This time, only ErA-WT and ErA-DM1 were compared since these enzymes represent the extremes in terms of L-glutaminase activity (highest in ErA-WT, lowest in ErA-DM2). As seen for the T-ALL LOUCY cell line, both ErA-WT and ErA-DM1 dramatically reduced the number of cancer cells in the mice (FIG. 1B).

Indication for Reduced Toxicity of the Low L-Glutaminase ErA Variants.

Figure 2:
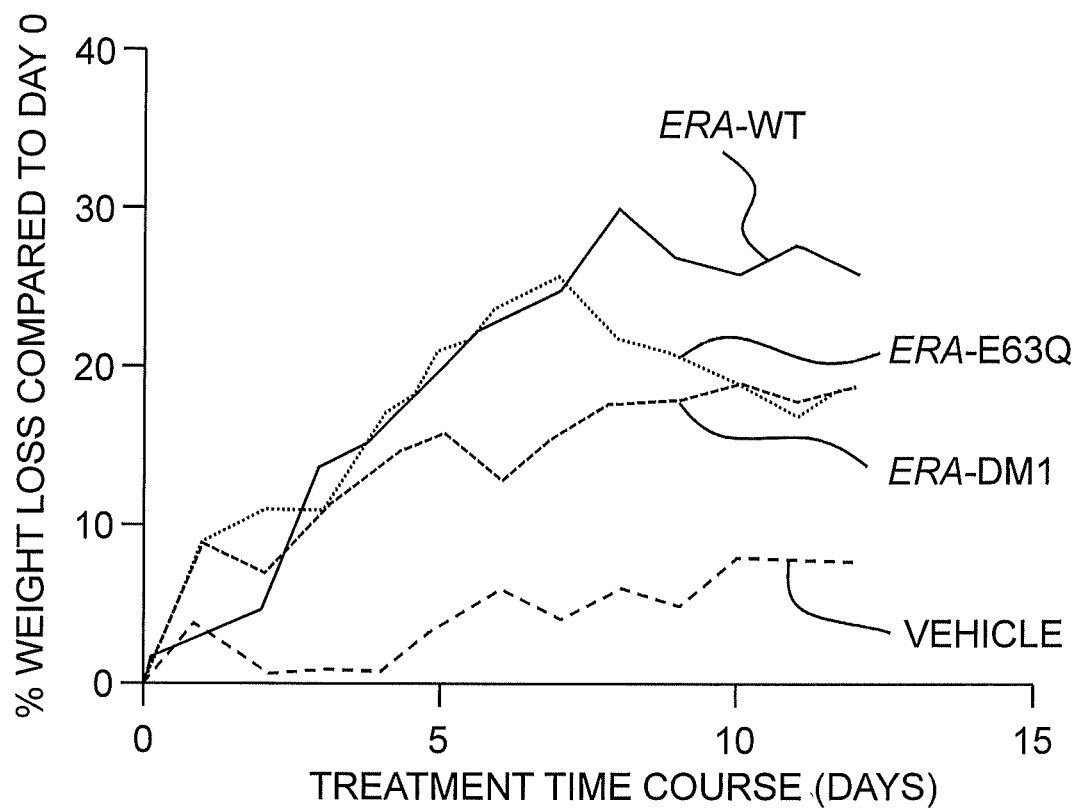
FIG. 2 shows that weight loss of animals inoculated with LOUCY (human T-ALL) cells and administered wild-type and ErA variants (ErA-E63Q and ErA-E63Q-S254N (ErA-DM1)) correlated with the L-glutaminase activity, wherein higher L-glutaminase activity resulted in more weight loss. Similar results were obtained for animals inoculated with SUP-B15 (human B-ALL) cells. Since weight loss is an indicator of toxicity, the reduced weight loss of animals treated with the low L-glutaminase ErA variants indicates that these enzymes possess reduced toxicity.

The data presented herein demonstrate that L-asparaginases that contain only very low L-glutaminase activity are potent inhibitors of ALL proliferation in vivo. In addition, it was noted that the weights of the animals were dramatically affected by drug administration, an effect which correlated with the relative L-glutaminase activity. The higher the L-glutaminase activity of the drug, the larger the weight loss (FIG. 2). Of note, the weight loss had no correlation with disease burden. In fact, the vehicle-treated mice (the sickest cohort) suffered the least weight loss. This indicates that the observed weight loss was due to Gln depletion by the enzymes, with higher depletion (as would be expected for ErA-WT) leading to largest weight loss. Conversely, mice treated with the enzyme expected to induce the least Gln depletion, i.e., ErA-DM2, imparted the lowest amount of weight loss.

To further probe the difference in activities between ErA-WT, ErA-DM1, and that of EcA-WT, NMR was used to follow the asparagine and glutamine levels as a function of time in solution at 37° C. For these experiments, the concentration present in the cell culture experiments was selected as the starting concentrations of these amino acids, i.e., 2.05 mM Gln and 0.375 mM Asn. Notably, human blood contains ~0.6 mM Gln and ~0.05 mM Asn. For all enzymes, added at a dose of 0.5 IU/ml, all of the Asn had been hydrolyzed to Asp by the time the first time point was taken. This shows that the tested enzymes were very similar in terms of the ability to deplete Asn.

By comparison, when assessing Gln depletion, the enzymes displayed very different properties. As expected from its kinetic properties, ErA-WT was very efficient at depleting Gln; by the 48-hour time point all of the Gln had been hydrolyzed to Glu. Even after 24 hours, the Gln level had been reduced by ErA-WT from ~2 mM to ~0.1 mM. Since cell culture studies evaluating L-asparaginases often incubate the cells with the drugs for 72 or even 96 hours, it was not surprising that ErA-WT demonstrated very potent cell killing ability, as the cells would be deprived for a very long time of essential Gln. EcA-WT has intrinsically lower L-glutaminase activity, but showed the same Gln depletion as ErA-WT at the 24- and 48-hour time points (its slower L-glutaminase activity was noticeable in the 5 hour time point).

Most importantly, the ErA-DM1 variant had significantly reduced Gln depletion. At the 24 hour time point, the Gln levels of the solution incubated with this enzyme were still ~0.4 mM, and at 48 hours ~0.1 mM. Only at the 72-hour time point was Gln fully depleted by ErA-DM1. Of note, Gln undergoes spontaneous hydrolysis, and under the experimental conditions used, significant Gln was hydrolyzed during the 4-day incubation period of the experiment. Therefore, the amount of Gln depletion at the later time is a combination of L-asparaginase catalyzed hydrolysis and spontaneous hydrolysis. Thus, if one limits the analysis to the 24-hour time point, at which negligible spontaneous Gln hydrolysis has occurred, it is very apparent that ErA-DM1 causes much less Gln depletion relative to ErA-WT or EcA-WT.

In light of the high L-asparaginase activity and concomitant decrease in L-glutaminase activity, the ErA variants described herein can be readily used, in particular in a PEGylated a fusion protein form to increase in vivo half-life, in the treatment of cancers such as ALL.

Example 3: Structural Basis for Low L-Glutaminase Activity of Engineered ErA

Residue Selection for Mutagenesis.

Figure 3:
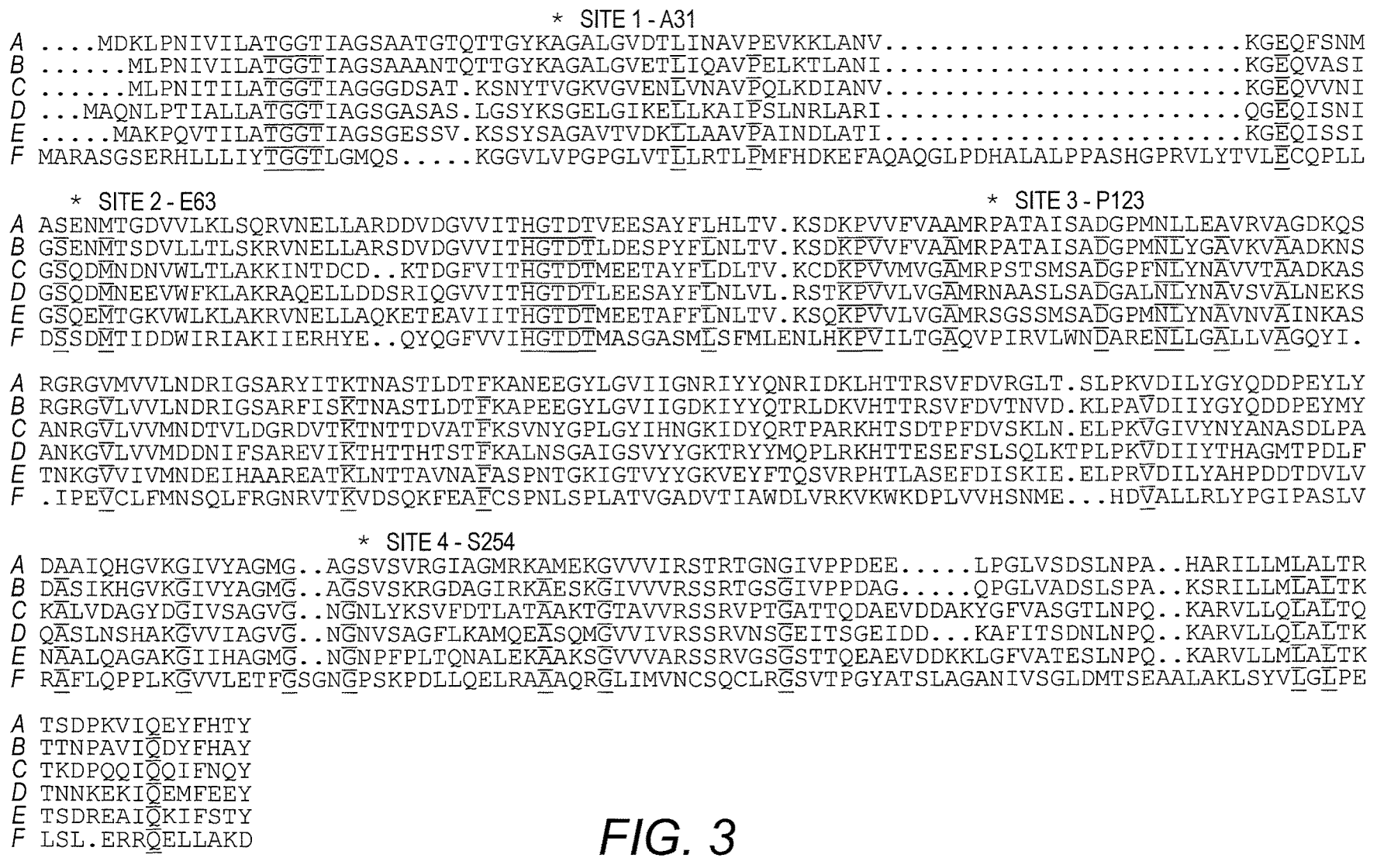

Four residues Ala31, Glu63, Pro123, and Ser254 were identified as candidate sites that may influence the L-glutaminase/L-asparaginase ratio. Due to their role in catalysis, residues present in consensus motifs among the L-asparaginase/L-glutaminase superfamily (indicated with asterisks in FIG. 3 and includes T12GGT15, H93GTDT97, S62, K168) were excluded from consideration for mutation. Instead, non-conserved residues that surround the active site and that do not necessarily interact with the substrate were targeted. Based on a multiple sequence alignment (FIG. 3), and combined with analysis of the crystal structure of ErA in complex with the product Asp and Glu, Ala31, Glu63, Pro123 and Ser254 were identified as four potential candidate sites for mutagenesis. Interestingly, of these four residues, only one, Glu63, makes a direct interaction with the substrate.

Site 1, Ala31, is part of the flexible N-terminal loop that closes and becomes ordered in the presence of ligand at the active site. When ordered, Ala31 is located at the entrance of the substrate-binding pocket. While not interacting directly with the preferred substrate Asn, it is within 4 Å of the Cα atom of the amino acid. In the ErA structure with the larger substrate Gln, it was observed that the extra methylene atom present in this amino acid twists in the direction of Ala31. To maintain accommodation of Asn, but exclude Gln, the aim was to sterically constrain the cavity by replacing the small alanine side chain with a bulkier one. That is, this design was made to sterically repeal the extra Gln methylene group. Based on modeling studies, the side chains present in valine, isoleucine, leucine and methionine were identified as being most appropriate. Additionally, as shown in the sequence alignment (FIG. 3), Ala31 is replaced by a valine or serine in the case of the *E. coli* and *Helicobacter pylori* L-asparaginases, respectively. Compared to ErA, these enzymes have been reported to have either lower or negligible L-glutaminase activity (Parmentier, et al. (2015) *Leuk. Res.* 39:757-762; Cappelletti, et al. (2008) *Biochem. Biophys. Res. Commun.* 377:1222-1226). Accordingly, Ala31 was replaced with either serine or threonine (the latter mimicking valine but retaining hydroxyl group of serine).

Site 2, Glu63, is a residue that directly interacts with the α-amino group of the amino acid substrate. Structural analysis of ErA in complex with Asp and Glu showed that in order to accommodate the larger Glu, the substrate shifts in the direction of Glu63 relative to binding position adopted by the small Asp. To make this repositioning of Gln less favorable, Glu63 was replaced with a glutamine. This choice of mutation was reinforced by the fact that the counterpart of Glu63 in the low L-glutaminase *Helicobacter pylori* and *E. coli* L-asparaginases is a glutamine. Both the glutamate and glutamine side chains contain an oxygen atom that can participate in binding the α-amino group of either Asn or Gln. However, it was posited that the amino group present in the glutamine side chain (contrasted with a second oxygen atom in glutamate) may be less favorable for accommodating Gln. In addition to the E63Q mutant, an E63L mutation was also created in accordance with the identification of a Q59L ErA variant exhibiting high L-asparaginase activity (Chan, et al. (2014) *Blood* 123:3596-3606).

The third site chosen for mutagenesis was Pro123. This site was selected because this residue is either serine or asparagine in *Wolinella succinogenes* L-asparaginase and *Helicobacter pylori* L-asparaginase, respectively (FIG. 3), both of which exhibit low L-glutaminase activity. Based on the location of Pro123, it was expected that this residue may play an indirect role in increasing the preference for Asn over Gln. To demonstrate this, P123S and P123N ErA variants were prepared.

Residue Ser254, Site 4 for modification, is located at the entrance of the substrate-binding pocket and originates from an adjacent protomer. Therefore, as rationalized above for Ala31, it was postulated that replacing this serine with a residue having a larger side chain would exclude Gln. The multiple sequence alignment (FIG. 3) revealed the counterparts of this residue in *E. coli* and guinea pig enzymes (lower to no L-glutaminase activity) are asparagine and proline, respectively. Therefore, mutants S254N and S254P were created to probe the effect of this site on the L-glutaminase/L-asparaginase preference.

Kinetic Characterization of ErA Mutants.

In addition to ErA-WT, the 18 ErA mutants listed in Table 7 were expressed and purified.

TABLE 7

| Enzyme | % Glnase vs ErA-WT | % Asnase vs ErA-WT | % (Glnase/Asnase) within same protein[a] |
|---|---|---|---|
| ErA-WT | 100% | 100% | 14% |
| ErA-A31V | 72% | 81% | 13% |
| ErA-A31S | 124% | 110% | 16% |
| ErA-A31T | 18% | 28% | 9% |
| ErA-A31N | 3% | 33% | 1% |
| ErA-A31M | 7% | 26% | 3% |
| ErA-A31I | 65% | 85% | 12% |
| ErA-A31L | 6% | 12% | 4% |
| ErA-E63L | 0% | 12% | 0% |
| ErA-E63Q[b] | 31% | 90% | 5% |

TABLE 7-continued

| Enzyme | % Glnase vs ErA-WT | % Asnase vs ErA-WT | % (Glnase/Asnase) within same protein[a] |
|---|---|---|---|
| ErA-P123S | 2% | 3% | 11% |
| ErA-P123N | 1% | 2% | 6% |
| ErA-S254N | 34% | 40% | 12% |
| ErA-S254P[b] | 0% | 120% | 0% |
| ErA-A31T + E63Q | 8% | 15% | 7% |
| ErA-A31I + E63Q[b] | 22% | 60% | 5% |
| ErA-S254N + E63Q[b] | 0% | 82% | 0% |
| ErA-S254N + A31T | 9% | 18% | 7% |
| ErA-S254N + A31I | 22% | 25% | 12% |
| EcA-WT | 100% | 100% | 2% |

[a]Observed Glnase rate measured with 20 mM Gln and 5 nM enzyme; observed Asnase rate measured with 2 mM Asn and 0.5 nM enzyme.
[b]Mutants that were selected for determination of $k_{cat}$ and Km parameters.

Using colorimetric enzyme-coupled assays, L-asparaginase and L-glutaminase activity of the enzymes was determined. To assure that the rate at saturating substrate concentrations was measured, 10 mM Gln and 2 mM Asn were used as substrates for the L-glutaminase and L-asparaginase assays, respectively. Seventeen of the 18 mutants had reduced L-glutaminase activity (Table 7). However, for most of the mutants, this decrease was concomitant with a decline in the L-asparaginase activity. Using the criteria of (i) ≥60% retained L-asparaginase activity (relative to Erw-WT) and (ii) ≤5% L-glutaminase versus and L-asparaginase activity, mutants ErA-E63Q, ErA-S254P, ErA-A31I+E63Q and ErA-S254N+E63Q were selected for further study.

From the initial mutant screen at saturating substrate concentrations, the single mutant ErA-S245P seemed to have the most desired properties: The L-glutaminase activity being below the detection sensitivity of the assay conditions, whereas the L-asparaginase activity at 120% relative to the wild-type enzyme (Table 7). Further kinetic characterization of the mutant's L-asparaginase activity confirmed the high turnover rate with Asn. However, it also revealed a 25-fold increase (relative to ErA-WT) in the Km value for Asn (Table 8).

TABLE 8

| Enzyme | Km (μM) | $k_{obs}$ @50 μM (sec$^{-1}$) | $k_{obs}$ @20 μM (sec$^{-1}$) |
|---|---|---|---|
| ErA-WT | 47.5 ± 3.5 | 105.3 | 50.7 |
| ErA-S254P | 1154.2 ± 25.5 | 10.5 | 4.5 |

TABLE 8-continued

| Enzyme | Km (μM) | $k_{obs}$ @50 μM (sec$^{-1}$) | $k_{obs}$ @20 μM (sec$^{-1}$) |
|---|---|---|---|
| ErA-E63Q | 50.7 ± 2.0 | 92.2 | 46.3 |
| ErA-A31I-E63Q (DM2) | 36.9 ± 2.2 | 69.7 | 38.8 |
| ErA-E63Q-S254N (DM1) | 185.3 ± 5.5 | 36.3 | 18.9 |
| ErA-E63Q-S254Q (DM3) | 179.1 ± 5.6 | 30.8 | 14.2 |
| ErA-A31I-E63Q-S254Q (TM2) | 95.0 ± 3.5 | 89.1 | 40.8 |
| EcA-WT | 15.0 ± 0.5 | 41.3 | 28.3 |

Since clinical use of L-asparaginase requires complete depletion of blood Asn levels, the Km of the enzyme must be in the low micromolar range to be effective. Hence, while the goal of largely eliminating the L-glutaminase activity was achieved, the ErA-S245P variant was not selected for further analysis in light of the unacceptable increase in the Km value of Asn in the L-asparaginase reaction.

Further inspection of the properties of the mutants from the initial screen (Table 7) indicated that the three next most promising variants were the E63Q (ErA-E63Q) single mutant and the A31I-E63Q (ErA-DM2) and E63Q-S254N (ErA-DM1) double mutants. Further kinetic characterization of these mutants revealed that the critical Km value for the substrate Asn is comparable to that of ErA-WT (Tables 8 and 9). In fact, ErA-DM2 acquired an even lower Asn Km than that of ErA-WT (37 vs. 48 μM). In contrast, ErA-DM1 variant exhibited a 4-fold increase in Asn Km. Together with near wild-type $k_{cat}$ (range 60-90% of ErA-WT), these mutants fulfill the criteria required to achieve efficient depletion of Asn from the blood.

TABLE 9

| Enzyme name | $k_{cat}$ (sec$^{-1}$) | Km (μM) | $K_{cat}$/Km (sec$^{-1}$μM$^{-1}$) | $k_{obs}$ @50 μM (sec$^{-1}$) | $k_{obs}$ @20 μM (sec$^{-1}$) | Specific activity (IU/mg)[a] |
|---|---|---|---|---|---|---|
| ErA-WT | 207.5 ± 3.6 | 47.5 ± 3.5 | 4.37 | 105.3 | 50.7 | 353.2 ± 6.1 |
| ErA-E63Q | 186.8 ± 1.7 | 50.7 ± 2.0 | 3.68 | 92.2 | 46.3 | 317.8 ± 2.9 |
| ErA-A31I-E63Q (DM2) | 123.0 ± 1.8 | 36.9 ± 2.2 | 3.33 | 69.7 | 38.8 | 209.1 ± 3.1 |
| ErA-E63Q-S254N (DM1) | 169.8 ± 1.5 | 185.3 ± 5.5 | 0.92 | 36.3 | 18.9 | 288.8 ± 2.6 |
| ErA-S254P | 250.0 ± 2.8 | 1154.2 ± 25.5 | 0.22 | 10.5 | 4.5 | 425.4 ± 4.8 |
| EcA-WT | 44.4 ± 0.3 | 15.0 ± 0.5 | 2.96 | 41.3 | 28.3 | 76.3 ± 0.5 |
| ErA-E63Q-S254Q (DM3) | 147.3 ± 1.0 | 179.1 ± 5.6 | 0.82 | 30.8 | 14.2 | 250.4 ± 1.7 |
| ErA-A31I-E63Q-S254N (TM1) | 109.7 ± 0.8 | 124.2 ± 4.3 | 0.89 | 29.2 | 16.4 | 186.4 ± 1.4 |
| ErA-A31I-E63Q-S254Q (TM2) | 261.2 ± 2.8 | 95.0 ± 3.5 | 2.75 | 89.1 | 40.8 | 443.5 ± 4.8 |

[a] 1 IU of enzyme is defined as the amount of enzyme used to produce 1 μmole of product in 1 minute at 37° C.

The precise kinetic parameters for the undesired L-glutaminase activity were subsequently determined. This work established that the reduced L-glutaminase activity of these mutants is due to a reduced $k_{cat}$ (3-9 fold lower) and much increased Km (8-44 fold higher) compared ErA-WT (Tables 10 and 11).

TABLE 10

| Enzyme | Km (μM) | $k_{obs}$ @500 μM (sec$^{-1}$) | $k_{obs.}$ @100 μM (sec$^{-1}$) |
|---|---|---|---|
| ErA-WT | 360 ± 20 | 15.06 | 6.118 |
| ErA-E63Q | 3860 ± 230 | 0.72 | 0.098 |
| ErA-A31I-E63Q (DM2) | 2730 ± 20 | 0.73 | 0.105 |
| ErA-E63Q-S254N (DM1) | 15800 ± 300 | 0.07 | 0.019 |

TABLE 10-continued

| Enzyme | Km (μM) | $k_{obs}$ @500 μM (sec$^{-1}$) | $k_{obs.}$ @100 μM (sec$^{-1}$) |
|---|---|---|---|
| ErA-E63Q-S254Q (DM3) | 84000 ± 560 | 0.02 | 0.009 |
| ErA-A31I-E63Q-S254Q (TM2) | 47500 ± 700 | 0.0083 | 0.0045 |
| EcA-WT | 1380 ± 90 | 0.22 | 0.047 |

TABLE 11

| Enzyme name | $k_{cat}$ (sec$^{-1}$) | Km (μM) | $k_{cat}$/Km (sec$^{-1}$μM$^{-1}$) | $k_{obs}$ @1 mM (sec$^{-1}$) | $k_{obs}$ @0.5 mM (sec$^{-1}$) | Specific activity (IU/mg)[a] |
|---|---|---|---|---|---|---|
| ErA-WT | 26.84 ± 0.26 | 360 ± 20 | 74.56 × 10$^{-3}$ | 19.22 | 15.87 | 45.68 ± 0.44 |
| ErA-E63Q | 8.33 ± 0.16 | 3,860 ± 230 | 3.68 × 10$^{-3}$ | 2.16 | 0.74 | 14.17 ± 0.27 |
| ErA-A31I-E63Q (DM2) | 6.01 ± 0.13 | 2,730 ± 200 | 2.2 × 10$^{-3}$ | 2.20 | 0.83 | 10.22 ± 0.22 |
| ErA-E63Q-S254N (DM1) | 2.93 ± 0.03 | 15,800 ± 300 | 0.19 × 10$^{-3}$ | 0.18 | 0.11 | 4.98 ± 0.05 |
| EcA-WT | 0.89 ± 0.01 | 1,380 ± 90 | 0.64 × 10$^{-3}$ | 0.36 | 0.22 | 1.53 ± 0.02 |
| ErA-E63Q-S254Q (DM3) | 7.17 ± 0.64 | 84,000 ± 12,000 | 0.85 × 10$^{-3}$ | 0.19 | 0.0226 | 12.17 ± 1.19 |
| ErA-A31I-E63Q-S254N (TM1) | 5.6 ± 0.2 | 28,200 ± 2,300 | 0.19 × 10$^{-3}$ | 0.33 | 0.11 | 9.51 ± 0.34 |
| ErA-A31I-E63Q-S254Q (TM2) | 1.836 ± 0.11 | 47,460 ± 695 | 0.04 × 10$^{-3}$ | — | 0.0083 | 3.12 ± 0.02 |

[a] 1 IU of enzyme is defined as the amount of enzyme used to produce 1 μmole of product in 1 minute at 37° C.

As indicated by the $k_{cat}$/Km parameter, the L-glutaminase efficiency of the mutants was reduced by about 20-400 fold. Likewise, at the physiological blood concentration of 0.5 mM, the observed L-glutaminase rate was reduced by 95-99% relative to ErA-WT. This analysis demonstrates that these three mutants largely fulfill the design criteria of being severely impaired in their L-glutaminase activity but with near ErA-WT L-asparaginase activity.

Molecular Basis for Improved L-Asparaginase Selectivity.

Although structural considerations were incorporated into the design of the mutants discussed above, the mechanism for the increased Asn selectivity was verified. Accordingly, the ErA-E63Q, ErA-DM1, and ErA-DM2 enzyme variants were crystallized with either Asp or Glu (the products of the L-asparaginase and L-glutaminase reaction, respectively). High resolution diffraction data was collected on both Asp and Glu soaked crystals. For the Asp soaked crystals (see Table 1 for data collection and refinement statistics), inspection of the electron density at the enzymes' active sites unambiguously showed the presence of the ligand. However, despite several attempts under different soak conditions (e.g., increasing soak time, increasing Glu concentration), electron density for the soaked Glu was not observes. Instead, the active site of the Glu soaked crystals had electron density for HEPES buffer, which is a component of the crystallization solution. A molecule of HEPES was previously observed bound at the active site of apo ErA-WT, which was crystallized using the same conditions. Of note, for ErA-WT, both soaked Asp and Glu are able to displace the buffer molecule from the active site. In contrast, for the three ErA mutants discussed here, only Asp (but not Glu) was successful in fully displacing the bound HEPES molecule. This inability of soaked Glu to displace the buffer molecule in the ErA mutant crystals correlates with their much-increased Gln Km value relative to the wild-type enzyme.

Overall Structure of the ErA Variants.

ErA-WT builds a tetramer composed of a dimer-of-dimers, irrespective of the presence or absence of Asp/Glu at the active site. However, in the absence of Asp/Glu, the N-terminal region (residues 18-34) lacks clear electron density. This so-called flexible N-terminal loop was observed ordered and approaching the active site when either Asp or Glu bound to ErA-WT. For the three ErA variants analyzed here (ErA-E63Q, ErA-DM1, ErA-DM2), the tetrameric organization is maintained, and the flexible N-terminal loop displayed clear electron density and adopted its closed conformation. The ErA-E63Q-Asp, ErA-DM1-Asp, and ErA-DM2-Asp structures were solved at a resolution of 2.05 Å, 1.50 Å, and 1.60 Å, respectively (Table 1) and all are very similar to the ErA-WT-ASP structure (PDB ID 5F52; rmsd of 0.09-0.135 Å).

Binding of ASP to ErA-E63Q.

As indicated, in the wild-type enzyme, Glu63 directly interacts with the α-amino group of the amino acid ligand (Asp or Glu); in the specific case of ErA-WT-Asp, that interaction distance is 2.8 Å. It was postulated that replacing Glu63 with a glutamine would result in interaction that is more distance sensitive since, whereas Glu63 forms a salt-bridge with the α-amino group of the substrate, Gln63 would form a H-bond. The increase in distance sensitivity of this interaction was predicted to affect the binding of Gln but not of Asn. The assignment of the Gln63 side chain orientation (carbonyl oxygen atom versus amide nitrogen atom) was done based on chemical reasoning, where the amide nitrogen atom of Gln63 (a H-bond donor) would be the one further away from the α-amino group of the ligand (also a H-bond donor).

The analysis indicated that in the ErA-E63Q-Asp structure the interaction distance between the α-amino group of the ligand (Asp) and the carbonyl moiety of the glutamine side-chain of Gln63 had increased to 3.0 Å. Importantly, the distance between the amide nitrogen atom of Gln63 and the α-amino group of the ASP ligand was acceptably long at 3.9 Å. In other words, in the case of ASP (and holding true also for the substrate Asn), there was sufficient separation between these H-bond donor moieties so as not to negatively affect the L-asparaginase reaction. This explains why this mutant maintains a high L-asparaginase activity.

Binding of Asp to ErA-DM1.

The crystal structure of the A31I-E63Q double mutant (ErA-DM2) in complex with Asp (ErA-DM2-Asp) was subsequently determined. The minimal effect of the E63Q mutation on ErA-DM2 was similar to that seen for ErA-E63Q. In contrast, the effect of the A31I mutation was more significant, impacting the conformation of the flexible N-terminal loop. While still closed, this loop adopted a different conformation to the one seen in the ErA-WT-Asp complex structure. The isoleucine in position 31 that replaced the smaller alanine prevented this section of the N-terminal flexible loop from approaching the substrate binding site. In ErA-WT-Asp, the alanine at position 31 was 4.1 and 5.3 Å away from the Cα and Cβ atoms of the bound Asp, respectively. When Ala31 was replaced by the larger isoleucine, the position of the flexible N-terminal loop adjusted such that the tip of the isoleucine in the ErA-DM2-Asp was nearly at the same distance from the ASP (4.2 and 5.3 Å). Hence, this structure revealed how the mutant adapts to maintain its L-asparaginase activity.

Binding of Asp to ErA-DM1.

The single substitution of Ser254 to asparagine resulted in a mutant with a comparable decrease in L-asparaginase and L-glutaminase activities (Table 7). Interestingly, combining the S254N mutation with the E63Q mutation (ErA-DM1) resulted in a variant that was highly selective toward Asn (Tables 8 and 10). To understand this phenomenon, the crystal structure of ErA-DM1 in complex with Asp (ErA-DM1-Asp) was solved. Again, the minor effect of the E63Q mutation was similar to that previously discussed. Residue 254, the site of the second mutation, originated from a neighboring protomer in the tetrameric enzyme (denoted with a prime after the number). In ErA-WT, Ser254' did not interact directly with the bound ASP (distance 4.0 Å to the α-amino group of Asp) but rather functioned to position the side chain of the conserved Asp96 (2.7 Å distance between the Ser254' hydroxyl and the side chain of Asp96). When Ser254' was mutated to an asparagine, the larger side chain was now closer to the bound ASP (3.5 Å to the α-amino group of Asp) and maintained the positioning interaction with Asp96 (3.1 Å). The orientation of the Asn254' was dictated by Asp96, such that the Asn254' side chain amide nitrogen atom (H-bond donor) faced the carboxylic acid moiety of Asp96 (H-bond acceptor). This is an important point, since the Asn254' side chain amide nitrogen atom, as positioned by Asp96, now generates repulsion to the α-amino group of Asn or Gln. This explains why the ErA-S254N single mutant had decreased activity with both Asn and Gln (Table 7).

The kinetic property of the enzyme was markedly different when the S254N mutation was combined with the E63Q mutation (i.e., ErA-DM1). Similar to the previous E63Q containing variants, the distance in the ErA-DM1-Asp structure between the side chain at position 63 and Asp increased to 3.0 Å. This increase in distance, while small, increased the separation between Asn254' and the substrate Asn to 3.5 Å. This shift in the position of Asp (due to the E63Q mutation) allowed it to lessen the repulsive interaction with the side chain of Asn254'. In other words, the E63Q mutation sufficiently displaced the ligand such as to limit the repulsive interaction between the ligand α-amino group (H-bond donor) and the Asn254' amide nitrogen atom (also a H-bond donor). This allows ErA-DM1 to maintain high L-asparaginase activity.

Modeling the Glu Binding Mode to the ErA Variants.

The preceding structural analysis demonstrates the compatibility of the mutations with the enzymatic activity with Asn. Accordingly, basis for the incompatibility of the mutations with the hydrolysis of Gln was sought. However, direct experimental view of how the mutants bind Gln was not possible since the Glu-soaked crystals of the mutant enzymes failed to bind the amino acid. Therefore, the ErA-WT-Glu was overlaid with the mutant structures. While not being bound by theory, in this type of analysis it was postulated that Glu binds to the mutant enzymes the same as observed to ErA-WT. This analysis provides insight into the potential Glu binding mode to the mutant variants.

The E63Q mutation must play a key role in the discrimination between Asn and Gln as it is present in all three mutants discussed so far that have high L-asparaginase/low L-glutaminase properties. The overlay of ErA-WT-Glu and the ErA-E63Q structure provided the putative Glu binding mode to ErA-E63Q, and revealed a short distance between the Glu α-amino group and the Gln63 amide nitrogen atom (3.5 Å). Since both of these moieties are H-bond donors, such proximity would be detrimental for the binding of this amino acid. As discussed, in the case of ASP, whose smaller size allowed it to reposition away from Gln63, the analogous H-bond:H-bond distance was 3.9 Å, and was therefore less detrimental. In the wild-type enzyme, instead of an amide nitrogen, there was the second oxygen atom of the Glu63 side chain carboxylate, which was an H-bond acceptor, and this explains why Gln is a relatively good substrate of ErA-WT. The Glu does not reposition, as ASP does to increase the distance to the amide nitrogen atom of Gln63 since the Glu side chain carboxylate (and that of Asp) is anchored by Thr95. This threonine, in combination with Thr15, is important for the enzymatic hydrolysis of Asn and Gln. Hence, the E63Q mutation discriminates against Gln by exploiting the requirement of this large amino acid to fit in the active site by shifting in the direction of Glu63/Gln63, which in turn would place the Gln α-amino group at an unfavorable proximity to the Gln63 amide nitrogen atom (but is compatible with wild-type Glu63).

The A31I (as present in ErA-DM2) does not act to increase the discrimination against Gln, but rather, reduces the Km of Asn (from 51 µM in ErA-E63Q to 37 µM in ErA-DM2). This mutation also reduces the Km of Gln. The ErA-DM1-ASP structure revealed that this mutation forces the flexible N-terminal loop to adopt a different closed conformation relative to the one adopted by the wild-type enzyme. How this reduces the Asn Km value is not apparent from the structure. It was speculated that this mutation influences the dynamics of loop closure, and that this ultimately influences the substrate Km value.

The S254N mutation (as present in ErA-DM1) does increase the selectivity between Asn and Gln, and it does so in a similar manner to the E63Q mutation. Namely, this mutation introduces a H-bond donor in proximity to the Gln α-amino group. Overlay of ErA-WT-Glu and ErA-DM1-Asp revealed the likely position Glu would adopt when bound to the mutant enzyme. This superposition revealed that the larger Glu, by shifting towards Asn254', would result in an unfavorably short (3.2 Å) separation between H-bond groups. The reason that the smaller substrate Asn was not affected by this mutation to a significant degree (though its Km is also increased from 51 µM in ErA-E63Q to 185 in ErA-DM1) was due to the larger separation (3.5 Å) between these H-bond donor groups.

Exploiting the Structural Analysis to Develop Improved $2^{nd}$-Generation Mutants.

The previous work has identified positions 63 and 254 as "hot-spots" for Asn/Gln selectivity, and position 31 for reducing the substrate Km value. Accordingly, it was determined whether a variant with substitutions at all three hot-spots would have improved properties. The triple mutant ErA-A31I-E63Q-S254N (ErA-TM1) did indeed have a lower Km for Asn (110 versus 170 µM for ErA-DM1, Table 9) but its L-glutaminase rate increased (Table 11). Together, ErA-TM1 was only marginally better than the previous best variant, ErA-DM1.

The structure of ErA-DM1-Asp indicated that glutamine at position 254 may better discriminate against Gln. Indeed, the ErA-E63Q-S254Q (ErA-DM3) variant was endowed with an even higher Gln Km compared to ErA-DM1 (84 versus 15.8 mM) (Table 8). Critically, the L-asparaginase activity of ErA-DM3 was not negatively impacted by changing Ser254 from an asparagine (as in ErA-DM1) to a glutamine (Table 8).

Since a variant with an extremely high Gln Km value (ErA-DM3) was identified, the A31A mutation was added to this variant. A benefit of adding to this variant the A31A mutation included a reduction in the Asn Km value. Indeed, ErA-A31I-E63Q-S254Q (ErA-TM2) had an Asn Km value that was approximately half of that of ErA-DM3 (95 versus 179 µM, Table 8). The Km value of Gln was also reduced (47.5 versus mM), but despite this reduction, remained 100-fold higher than the physiological blood Gln concentration. Accordingly, the ErA triple mutant A31I-E63Q-S254Q (ErA-TM2) possessed the best combination of high L-asparaginase/low L-glutaminase properties (Table 12).

TABLE 12

| Enzyme Name | $k_{obs}$ [Asn$_{50}$]/ $k_{obs}$ [Gln$_{500}$]$^a$ | Specific activity (Asn)/ Specific Activity (Gln)$^b$ |
|---|---|---|
| ErA-WT | 6.6 | 7.3 |
| ErA-E63Q | 125 | 22 |
| ErA-E63Q-S254N (DM1) | 330 | 60 |
| ErA-A31I-E63Q-S254Q (TM2) | 8910 | 142 |
| EcA-WT | 188 | 50 |

$^a k_{obs}$ for Asn@50 µM, $k_{obs}$ for Gln@500 µM.
$^b$Specific activity (units of IU/mg) was determined at saturating substrate concentration (Asn or Gln).

The Ultra-Low L-Glutaminase ErA-TM2 Variant Maintains Its Cell Killing Properties.

This work designed and characterized several ErA variants that had high L-asparaginase and low L-glutaminase activity, with two variants (ErA-DM3 and ErA-TM2) having ultra-low L-glutaminase properties. To test whether variants with ultra-low L-glutaminase activity maintained the ability to kill ALL cells, the human T-ALL LOUCY cell line was exposed to increasing concentrations of ErA-TM2, and the IC$_{50}$ value of this enzyme was determined. This analysis indicated that the ErA-TM2 had a comparable IC$_{50}$ value (0.00061 IU/mL) to that of ErA-WT (0.00033 IU/mL).

Efficacy of the Ultra-Low L-Glutaminase ErA-TM2 in Mice.

Figure 4:
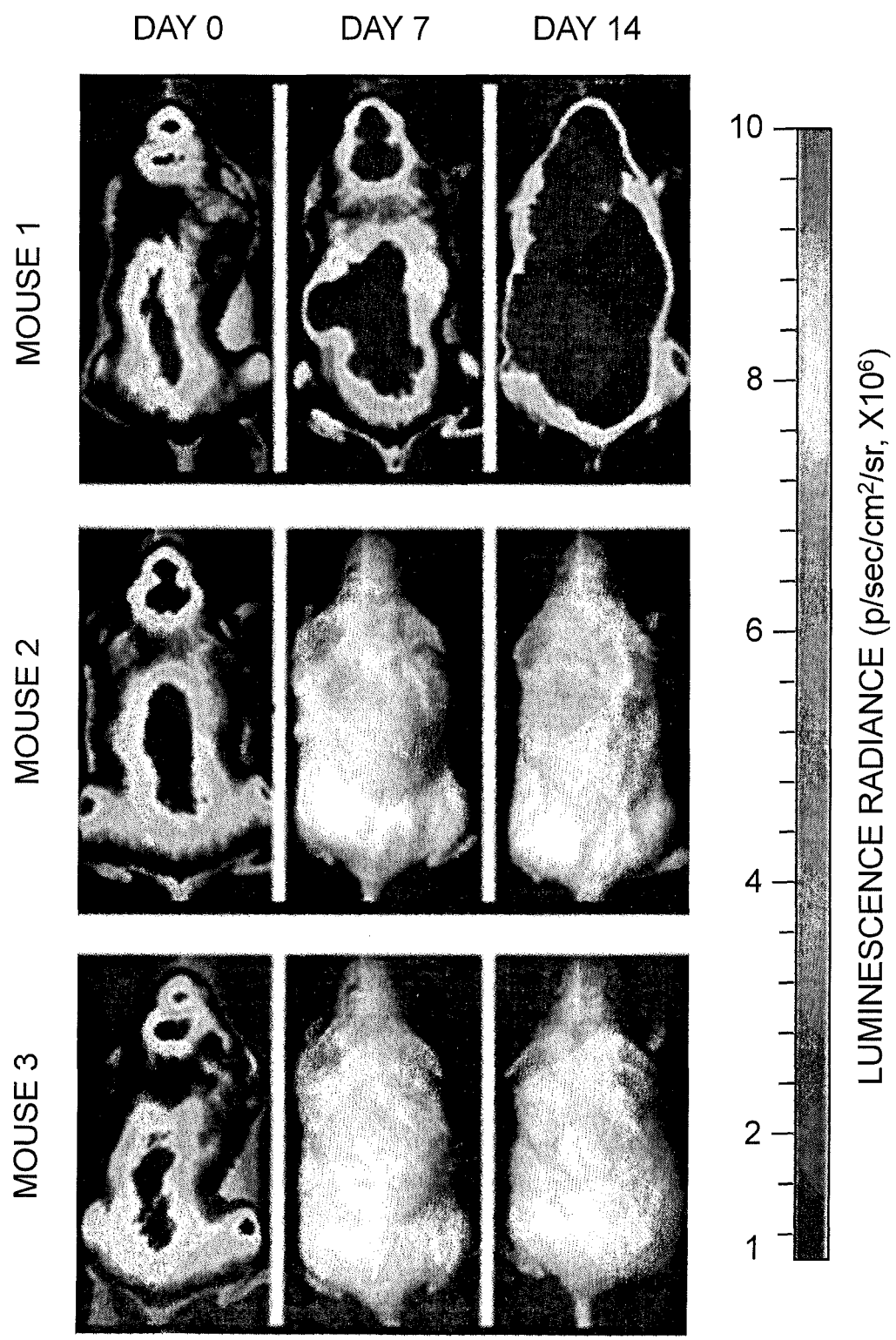
FIG. 4 shows that the ultra-low L-glutaminase ErA-TM2 variant eliminates T-ALL LOUCY cells as effectively as the high L-glutaminase ErA-WT. Female mice tail vein-injected with luciferase-expressing LOUCY cells four weeks prior were treated daily with vehicle (n=3); ErA-WT (n=4); and ErA-TM (n=4) for 14 days (drug dose 50 IU/mouse/day; i.p.). For each group, the representative animal shown had the highest bioluminescence imaging signal at day 0 of treatment.

Female mice were tail vein-injected with luciferase-expressing LOUCY cells. Four weeks later, mice were treated daily with vehicle (n=3), ErA-WT (n=4), or ErA-TM2 (n=4) for 14 days (drug dose 50 IU/mouse/day; i.p.). The bioluminescence signal was measured at days 0, 7 and 14. Relative bioluminescence imaging (BLI) flux at day 14 was assessed and found to increase 10-fold relative to day 0 in the vehicle treated mice. For both treated groups (ErA-WT and ErA-TM2), the flux decreased dramatically relative to vehicle control (p-value <0.0001), returning to background levels by day 14, with no significant difference between the treated groups. Peripheral blood % huCD45+ levels were determined one week prior to treatment initiation (day −7), at treatment start (day 0), and at end of treatment (day 14). At day 0, all animals were highly engrafted, as indicated by % huCD45+>8%. By day 14, for the vehicle-treated mice, the % huCD45+ increased to 40-60%, whereas for both treatment groups, the % huCD45+ was undetectable (p-value <0.0001 between vehicle- and enzyme-treated groups). At day 0, assessment of bone marrow % huCD45+ in three mice with similar BLI flux as the ones used for treatment revealed high engraftment. At day 14, bone marrow % huCD45+ remained high in the vehicle-treated mice, but was undetectable in both enzyme-treated groups (p-value <0.0001 between vehicle- and enzyme-treated groups). Spleens from the vehicle-treated mice were highly enlarged, whereas spleens from the ErA-WT and ErA-TM2 groups resembled normal mouse spleens in size. H&E-stained paraffin sections of livers from vehicle-, ErA-WT- and ErA-TM2-treated mice showed that vehicle-treated animals had livers filled with deposits of lymphoblastic leukemic cells. In contrast, livers of mice treated with ErA-WT or ErA-TM2 had no detectable leukemic cells present. Regarding killing activity, the results of this analysis indicated a remarkable killing effect of the ALL cells by ErA-TM2 (FIG. 4). In particular, the ultra-low L-glutaminase ErA-TM2 eliminates T-ALL LOUCY cells as effectively as the high L-glutaminase ErA-WT. Further, using weight loss (in grams, relative to day 0) as an indicator of toxicity, it was observed that whereas ErA-WT-treated mice exhibited a pronounced daily weight loss, weight loss was ameliorated in the ErA-TM2-treated group by 0.29 g/day (p-value <0.0001).

To further correlate L-glutaminase activity and toxicity, CD-1 mice were subjected to an acute single dose-escalation toxicity study. Each group had 3 males and 3 females, except group 6 which had only 4 animals (3 females, 1 male) due to a shortage of ErA-TM2. Animals administered ErA-WT presented significant physical and behavioral symptoms, whereas the ErA-TM2 administered animals were largely devoid of such symptoms (Table 13).

TABLE 13

| | ErA-WT | | | ErA-TM2 | | |
|---|---|---|---|---|---|---|
| Group | 1 | 2 | 3 | 4 | 5 | 6 |
| Dose (IU/g) | 40 | 80 | 160 | 40 | 80 | 160 |
| Hunched posture | 6 (2-4) | 6 (2-4) | 6 (1-4) | 0* | 0* | 4(1) |
| Decreased activity | 0 | 6(3) | 0 | 0 | 0* | 0 |
| Sunken eyes | 1 (2-3) | 6 (2-3) | 6 (1-4) | 0 | 0* | 0* |
| Rough coat | 6 (1-4) | 6 (1-4) | 6 (1-4) | 4 (1-2) | 0* | 0* |

The number of animals (out of 6 total) presenting symptoms is indicated. In parenthesis, the day(s) on which the symptom was observed is noted. One male in group 3 was dosed with 136 IU/g, and one female in group 5 was dosed with 60 IU/g.
*p < 0.05, analysis by Fisher's exact test: (Group 1 vs. Group 4, Group 2 vs. Group 5, Group 3 vs. Group 6).
*p < 0.05, analysis by Mann-Whitney U Test: (Group 1 vs. Group 4, Group 2 vs. Group 5, Group 3 vs. Group 6).

Example 4: TRAIL-ErA Fusion Protein

TRAIL (TNF-related apoptosis inducing ligand) is a protein that induces cell death by apoptosis. Accordingly, a TRAIL-Asparaginase fusion protein was created to combine the activity of these two proteins. Using this fusion protein, the L-asparaginase component signals the cell to undergo apoptosis, and the TRAIL component induces cell death.

Efficacy of the Fusion Protein TRAIL$_{trimer}$-ErA-TM2 Toward Human AML Cells.

Human acute myeloid leukemia MV4;11 cells were cultivated in a humid atmosphere (5% $CO_2$, 37° C.) using RPMI 1640 media (with L-Glutamine) supplemented with 10% FBS (Hyclone) and 1× penicillin-streptomycin solution (Invitrogen). Ninety μL aliquots of cell suspension ($2.5 \times 10^5$ cells per mL) were cultured in triplicate in round-bottomed 96-well microtiter plates in the presence of 10 μL of either DPBS or $TRAIL_{trimer}$-ErA-TM2 to a final concentration ranging from 0.0001 to 2.5 IU/ml. After incubating the plates for 4 days at 37° C. in humidified air containing 5% $CO_2$, Alamar Blue (Invitrogen) was added to a final concentration of 10% v/v, and the plates were incubated for an additional 4 hours followed by reading of the fluorescence signal. The leukemic cell viability was calculated as the percentage of fluorescence counts in the presence of L-asparaginase versus that in the DPBS control. This analysis indicated that the active $TRAIL_{trimer}$-ErA-TM2 fusion protein possessed remarkably better killing property against the MV4;11 cell line ($IC_{50}$=0.064 IU/mL) compared to the L-asparaginase ErA-TM2 alone ($IC_{50}$=1.631 IU/mL).

To confirm that the better anticancer effect of $TRAIL_{trimer}$-ErA-TM2 resulted from the synchronization of both $TRAIL_{trimer}$ and L-asparaginase and not from the activity of $TRAIL_{trimer}$ alone, $TRAIL_{trimer}$-ErA-TM2 was replaced with the same quantity of the inactive mutant $TRAIL_{trimer}$-ErA-TM2-K168M. The results of this analysis demonstrated that with impaired L-asparaginase activity, the fusion $TRAIL_{trimer}$-ErA-TM2-K168M protein lost its MV4;11 cell killing effect.

Efficacy of the Fusion Protein $TRAIL_{trimer}$-ErA-TM2 Toward Human AML Cells in Mice.

Figure 5:
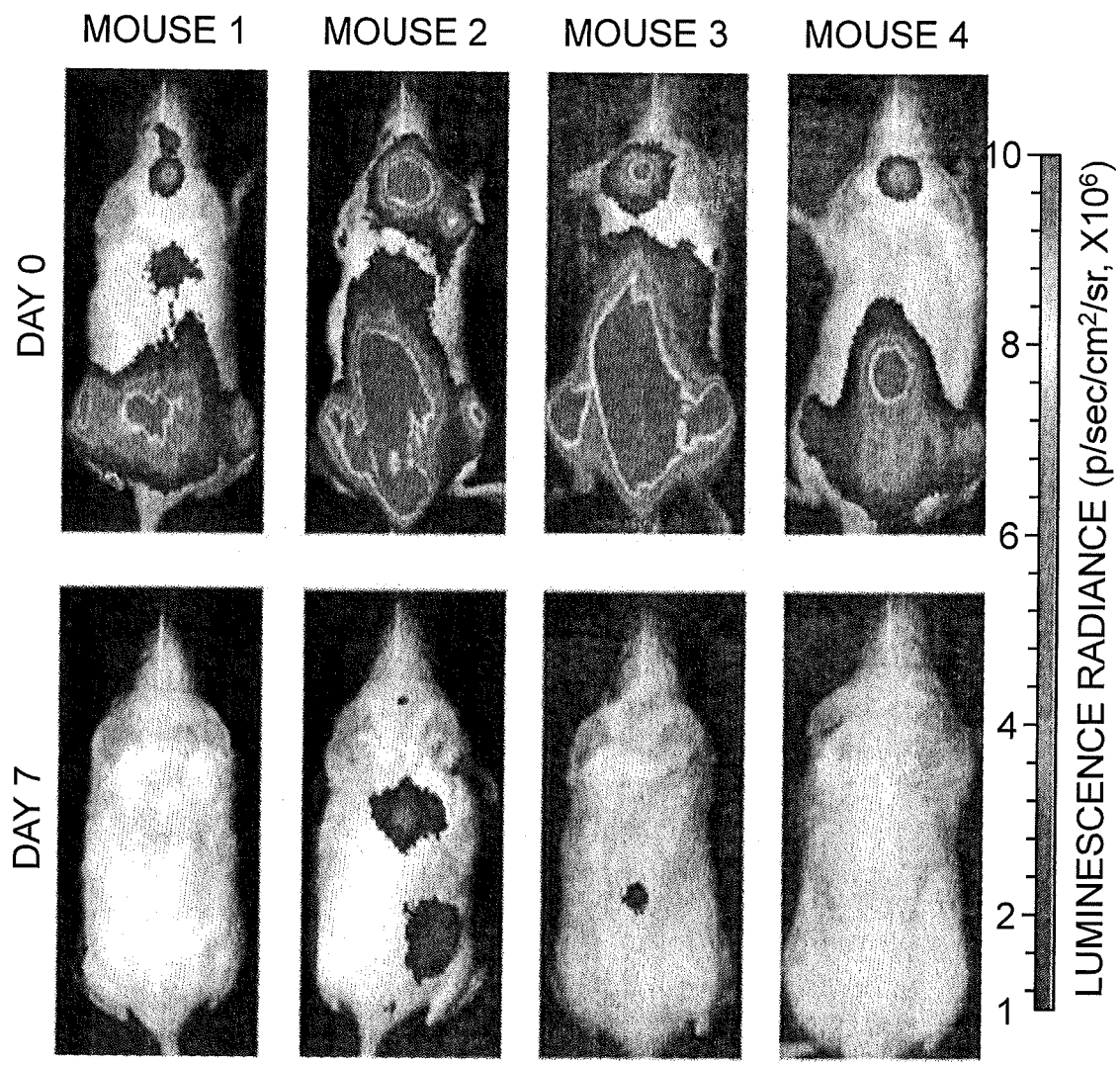
FIG. 5 shows the anticancer activity of the $TRAIL_{trimer}$-ErA-TM2 fusion protein in a mouse model of acute myeloid leukemia (AML).

Four non-obese diabetic/severe combined immune-deficient γ(NSG) mice (The Jackson Laboratory) were i.v.-injected at 6 weeks of age with 150 μL DPBS containing $5 \times 10^6$ luciferase-positive MV4;11 cells. At regular time points, the bioluminescence was measured using the IVIS Lumina II imaging system (PerkinElmer). After engraftment (Day 0), the mice were treated everyday for one week with an i.p. injection of 15 IU/mouse of $TRAIL_{trimer}$-ErA-TM2. The bioluminescence signal was measured at day 0 and day 7. The results of this analysis indicate a remarkable killing effect of the MV4;11 cells by $TRAIL_{trimer}$-ErA-TM2 (FIG. 5).

Example 5: Tags for Increasing In Vivo Half-Life

Efficacy of L-asparaginase is related to the in vivo half-life of the drug; the longer the half-life, the longer the enzyme acts to hydrolyze the blood asparagine. Accordingly, to increase the in vivo half-life of L-asparaginase, as well as the variants and fusion proteins disclosed herein, tags were fused to the N-terminus of L-asparaginase. The tags included a $His_6$-yeast SUMO tag, a $His_6$-human SUMO tag and an albumin-binding peptide SA21 tag. Each of the tags increased the circulation time of the L-asparaginase enzyme. In addition, combinations of tags were tested. In particular, the SA21 and yeast SUMO tags were combined to obtain variants with an even further extended half-life.

The Histidine Tag.

The DNA sequence specifying a string of six to nine histidine residues is frequently used in vectors for production of recombinant proteins. The result is expression of a recombinant protein with a 6×His or poly-His tag fused to its N- or C-terminus.

Expressed His-tagged proteins can be purified and detected easily and provide a means of specifically purifying or detecting the recombinant protein without a protein-specific antibody or probe. Kits are commercially available to His-tag proteins.

SUMO Modification.

It has been found that SUMO as an N-terminal fusion partner enhances functional protein production in prokaryotic and eukaryotic expression systems, based upon significantly improved protein stability and solubility.

Following the expression and purification of the fusion protein, the SUMO-tag can be cleaved by specific (SUMO) proteases via their endopeptidase activity in vitro to generate the desired N-terminus of the released protein partner. SUMO tag expression systems are commercially available. In some embodiments, the SUMO tag is a yeast SUMO tag (e.g., Smt3). In other embodiments, the SUMO tag is a human SUMO tag (e.g., SUMO-1, SUMO-2 or SUMO-3).

His-SUMO Modification.

Combining a polyhistidine (e.g., 6×His) tag and SUMO modification provides for efficient purification, increased expression and solubility, as well as increased half-life of L-asparaginases. Expression systems for providing the His-SUMO modification to a protein of interest are commercially available. See, e.g., the CHAMPION pET SUMO protein expression system (Invitrogen).

Albumin Binding Domain.

The albumin-binding domain is a small, three-helical protein domain found in various surface proteins expressed by gram-positive bacteria. Such albumin-binding regions have been used for protein purification or immobilization. Exemplary albumin binding domains include, but are not limited to, SA20 (QRLIEDICLPRWGCLWEDDF; SEQ ID NO:13), SA21 (RLIEDICLPRWGCLWEDD; SEQ ID NO:14), and SA31 (RLIEDICLPRWGCLW; SEQ ID NO:15).

Moreover, improvement of the pharmacokinetics, through the non-covalent association to albumin, by fusing such domains to therapeutic proteins has been shown to be successful. See Dennis, et al. (2002) *J. Biol. Chem.* 277(38): 35035-35043; US 2016/0185874; and US 2004/0001827.

Example 6: Site-Specific PEGylation

The function of PEG is to shield L-asparaginase from proteolytic degradation and from the host immune system. To allow for maleimide-based PEGylation of L-asparaginase, various amino acid residues were mutated to cysteine residues to identify a suitable location that had little to no effect on enzyme activity. Notably, ErA-WT and ErA-TM2 do not contain any cysteine residues. Therefore, the introduction of this amino acid residue had to be at an appropriate location of the enzyme so as not to disrupt folding or activity. Accordingly, the structure of ErA-TM2 was analyzed to identify regions of residues that could be mutated to cysteine. Five such regions were identified (Table 14), which: (1) were located on the surface, (2) were an appropriate distant from oligomerization interfaces (ErA-TM2 is a tetramer, so PEGylating a residue near an interface could be detrimental to the activity of the enzyme), and (3) included residues that pointed outward.

TABLE 14

| Region | Residue |
|---|---|
| 1 | K72 |
|  | R76 |
|  | E79 |
|  | D84 |
|  | D85 |

TABLE 14-continued

| Region | Residue |
|---|---|
| 2 | R206 |
|  | D210 |
|  | T215 |
|  | S216 |
| 3 | D235 |
|  | Q239 |
|  | H240 |
| 4 | A261 |
|  | R264 |
|  | K265 |
|  | E268 |
|  | K269 |
| 5 | K318 |
|  | E322 |

To demonstrate the use of the amino acid residues in Table 14 as sites for site-specific PEGylation, residue Asp84 of ErA-TM2 was mutated to cysteine. The resulting ErA-TM2-D84O protein was expressed, purified and PEGylated with mPEG-10K. Based upon SDS-PAGE analysis, ErA-TM2-D84C was PEGylated, as evidenced by a measurable increase in molecular weight of the ErA-TM2-D84C protein.

Subsequently, it was verified that the D84C mutation, and a PEGylated version thereof, does not negatively impact enzyme activity. When comparing the activity of ErA-TM2, ErA-TM2-D84C, and PEGylated-ErA-TM2-D84C, it was observed that the calculated rates of each enzyme were comparable, wherein PEGylation of ErA-TM2-D84C reduced the activity by less than 10% compared to ErA-TM2 (Table 15).

TABLE 15

| Variant | $k_{obs}$ at 2 mM Asn (1/sec) | % vs. ErA-TM2 |
|---|---|---|
| ErA-TM2 | 178.8 | 100 |
| ErA-TM2-D84C | 172.8 | 97 |
| 10K PEGylated-ErA-TM2-D84C | 163.4 | 91 |

In light of these data, there are 5 regions (Table 14) of an L-asparaginase disclosed herein that can be targeted to include the incorporation of a cysteine residue for PEGylation. In accordance with the invention, PEGylation can be achieved by maleimide-based conjugation of the cysteine residue(s) with large molecular weight PEG molecules such as PEG5K, PEG10K, PEG20K, PEG40K, as either linear or branched PEG molecules. It is contemplated that 1, 2, 3, 4 or 5 cysteine residues can be incorporated at the positions indicated in Table 14 thereby providing between 1 and 5 PEG attachment sites.

What is claimed is:

1. An *Erwinia chrysanthemi* L-asparaginase (ErA) variant comprising an amino acid substitution at (i) position 31 of SEQ ID NO:1, and (ii) position 63 or 254 of SEQ ID NO:1.

2. The ErA variant of claim 1, wherein the amino acid substitution at position 31 comprises an isoleucine, valine, leucine, or threonine.

3. The ErA variant of claim 1, wherein the amino acid substitution at position 63 comprises a glutamine, asparagine, or aspartate.

4. The ErA variant of claim 1, wherein the amino acid substitution at position 254 comprises an asparagine or glutamine.

5. The ErA variant of claim 1 comprising an amino acid sequence set forth in SEQ ID NO:4, SEQ ID NO:6 or SEQ ID NO:7.

6. The ErA variant of claim 1, wherein said ErA variant exhibits an asparaginase reaction rate ($k_{cat}$) of at least 75% of wild-type ErA enzyme.

7. The ErA variant of claim 1, wherein said ErA variant exhibits a Km for L-asparagine of less than 250 µM.

8. The ErA variant of claim 1, wherein said ErA variant exhibits a glutaminase reaction rate ($k_{cat}$) of less than 60% of wild-type ErA enzyme.

9. The ErA variant of claim 1, wherein said ErA variant exhibits a Km for L-glutamine of greater than 3 mM.

10. The ErA variant of claim 1, further comprising a histidine tag, a SUMO tag, an albumin-binding domain, or a combination thereof.

11. The ErA variant of claim 1, wherein said ErA variant is PEGylated.

12. A pharmaceutical composition comprising the ErA variant of claim 1 and a pharmaceutically acceptable excipient.

13. The pharmaceutical composition of claim 12, further comprising a stable form of TRAIL.

14. The pharmaceutical composition of claim 13, wherein the stable form of TRAIL comprises the FOLDON sequence GYIPEAPRDGQAYVRKDGEWVLLSTFL (SEQ ID NO:31).

15. A method of treating cancer comprising administering to a subject in need of treatment an effective amount of the ErA variant of claim 1 thereby treating the subject's cancer.

16. The method of claim 15, wherein the cancer is selected from non-Hodgkin's lymphoma, leukemia, acute lymphoblastic leukemia, acute myeloid leukemia, B cell lymphoma, Burkitt's lymphoma, chronic myelocytic leukemia, chronic lymphocytic leukemia, and hairy cell leukemia.

17. The method of claim 15, further comprising administering a stable form of TRAIL.

18. The method of claim 17, wherein the stable form of TRAIL comprises the FOLDON sequence GYIPEAPRDGQAYVRKDGEWVLLSTFL (SEQ ID NO:31).

19. A nucleic acid molecule encoding the ErA variant of claim 1.

20. An expression vector comprising the nucleic acid molecule of claim 19.

21. A host cell comprising the nucleic acid molecule of claim 19.

22. An *Erwinia chrysanthemi* L-asparaginase (ErA) variant comprising an amino acid substitution at one or more of positions 31, 63 and 254 of SEQ ID NO:1, wherein the ErA variant is PEGylated and further comprises a cysteine residue at position 72, 76, 79, 84, 85, 206, 210, 215, 216, 235, 239, 240, 261, 264, 265, 268, 269, 318, 322, or a combination thereof.

23. The ErA variant of claim 22, wherein the amino acid substitution at position 31 comprises an isoleucine, valine, leucine, or threonine.

24. The ErA variant of claim 22, wherein the amino acid substitution at position 63 comprises a glutamine, asparagine, or aspartate.

25. The ErA variant of claim 22, wherein the amino acid substitution at position 254 comprises an asparagine or glutamine.

26. The ErA variant of claim 22, further comprising a histidine tag, a SUMO tag, an albumin-binding domain, or a combination thereof.

27. A pharmaceutical composition comprising the ErA variant of claim 22 and a pharmaceutically acceptable excipient.

28. The pharmaceutical composition of claim 27, further comprising a stable form of TRAIL.

29. The pharmaceutical composition of claim 28, wherein the stable form of TRAIL comprises the FOLDON sequence GYIPEAPRDGQAYVRKDGEWVLLSTFL (SEQ ID NO:31).

30. A method of treating cancer comprising administering to a subject in need of treatment an effective amount of the ErA variant of claim 22 thereby treating the subject's cancer.

31. The method of claim 30, wherein the cancer is selected from non-Hodgkin's lymphoma, leukemia, acute lymphoblastic leukemia, acute myeloid leukemia, B cell lymphoma, Burkitt's lymphoma, chronic myelocytic leukemia, chronic lymphocytic leukemia, and hairy cell leukemia.

32. The method of claim 30, further comprising administering a stable form of TRAIL.

33. The method of claim 32, wherein the stable form of TRAIL comprises the FOLDON sequence GYIPEAPRDGQAYVRKDGEWVLLSTFL (SEQ ID NO:31).

34. A nucleic acid molecule encoding the ErA variant of claim 22.

35. An expression vector comprising the nucleic acid molecule of claim 34.

36. A host cell comprising the nucleic acid molecule of claim 34.

37. An *Erwinia chrysanthemi* L-asparaginase (ErA) variant comprising an amino acid substitution at one or more of positions 31, 63 and 254 of SEQ ID NO:1, further comprising three tandem soluble domains of TRAIL.

38. The ErA variant of claim 37, wherein the amino acid substitution at position 31 comprises an isoleucine, valine, leucine, or threonine.

39. The ErA variant of claim 37, wherein the amino acid substitution at position 63 comprises a glutamine, asparagine, or aspartate.

40. The ErA variant of claim 37, wherein the amino acid substitution at position 254 comprises an asparagine or glutamine.

41. The ErA variant of claim 37, wherein the soluble domains of TRAIL comprise residues 115-281 of SEQ ID NO:16.

42. The ErA variant of claim 37, wherein the three tandem soluble domains of TRAIL are linked to one another via a peptide linking group comprising one to eight amino acid residues.

43. The ErA variant of claim 42, wherein the amino acid residues are selected from glycine and serine.

44. The ErA variant of claim 37, wherein the three tandem soluble domains of TRAIL are linked to the ErA variant via a peptide linking group comprising one to twenty amino acid residues.

45. The ErA variant of claim 44, wherein the amino acid residues are selected from glycine and serine.

46. The ErA variant of claim 37, further comprising a histidine tag, a SUMO tag, an albumin-binding domain, or a combination thereof.

47. A pharmaceutical composition comprising the ErA variant of claim 37 and a pharmaceutically acceptable excipient.

48. A method of treating cancer comprising administering to a subject in need of treatment an effective amount of the ErA variant of claim 37 thereby treating the subject's cancer.

49. The method of claim 48, wherein the cancer is selected from non-Hodgkin's lymphoma, leukemia, acute lymphoblastic leukemia, acute myeloid leukemia, B cell lymphoma, Burkitt's lymphoma, chronic myelocytic leukemia, chronic lymphocytic leukemia, and hairy cell leukemia.

50. A nucleic acid molecule encoding the ErA variant of claim 37.

51. An expression vector comprising the nucleic acid molecule of claim 50.

52. A host cell comprising the nucleic acid molecule of claim 50.

53. A fusion protein comprising an L-asparaginase linked to three tandem soluble domains of TRAIL.

54. The fusion protein of claim 53, wherein the L-asparaginase is an L-asparaginase from *Erwinia chrysanthemi* or *Escherichia coli*.

55. The fusion protein of claim 54, wherein the *Erwinia chrysanthemi* L-asparaginase is a variant comprising an amino acid substitution at one or more of positions 31, 63 and 254 of SEQ ID NO:1.

56. The fusion protein of claim 53, wherein the soluble domains of TRAIL comprise residues 115-281 of SEQ ID NO:16.

57. The fusion protein of claim 53, wherein the three tandem soluble domains of TRAIL are linked to one another via a peptide linking group comprising one to eight amino acid residues.

58. The fusion protein of claim 57, wherein the amino acid residues are selected from glycine and serine.

59. The fusion protein of claim 53, wherein the three tandem soluble domains of TRAIL are linked to the L-asparaginase via a peptide linking group comprising one to twenty amino acid residues.

60. The fusion protein of claim 59, wherein the amino acid residues are selected from glycine and serine.

61. The fusion protein of claim 53, further comprising a histidine tag, a SUMO tag, an albumin-binding domain, or a combination thereof.

62. The fusion protein of claim 53, wherein said fusion protein is PEGylated.

63. The fusion protein of claim 62, wherein the L-asparaginase is an L-asparaginase from *Erwinia chrysanthemi* comprising the amino acid sequence of SEQ ID NO:1, SEQ ID NO:2, SEQ ID NO:3, SEQ ID NO:4, SEQ ID NO:5, SEQ ID NO:6 or SEQ ID NO:7, wherein said L-asparaginase has a cysteine residue at position 72, 76, 79, 84, 85, 206, 210, 215, 216, 235, 239, 240, 261, 264, 265, 268, 269, 318, 322, or a combination thereof.

64. A pharmaceutical composition comprising the fusion protein of claim 53 and a pharmaceutically acceptable excipient.

65. A method of treating cancer comprising administering to a subject in need of treatment an effective amount of the fusion protein of claim 53 thereby treating the subject's cancer.

66. The method of claim 65, wherein the cancer is selected from non-Hodgkin's lymphoma, leukemia, acute lymphoblastic leukemia, acute myeloid leukemia, B cell lymphoma, Burkitt's lymphoma, chronic myelocytic leukemia, chronic lymphocytic leukemia, and hairy cell leukemia.

67. A nucleic acid molecule encoding the fusion protein of claim 53.

68. An expression vector comprising the nucleic acid molecule of claim 67.

69. A host cell comprising the nucleic acid molecule of claim 67.

* * * * *

SEQUENCE LISTING

```
<160> NUMBER OF SEQ ID NOS: 31

<210> SEQ ID NO 1
<211> LENGTH: 327
<212> TYPE: PRT
<213> ORGANISM: Erwinia chrysanthemi

<400> SEQUENCE: 1

Met Asp Lys Leu Pro Asn Ile Val Ile Leu Ala Thr Gly Gly Thr Ile
1               5                   10                  15

Ala Gly Ser Ala Ala Thr Gly Thr Gln Thr Thr Gly Tyr Lys Ala Gly
            20                  25                  30

Ala Leu Gly Val Asp Thr Leu Ile Asn Ala Val Pro Glu Val Lys Lys
        35                  40                  45

Leu Ala Asn Val Lys Gly Glu Gln Phe Ser Asn Met Ala Ser Glu Asn
    50                  55                  60

Met Thr Gly Asp Val Val Leu Lys Leu Ser Gln Arg Val Asn Glu Leu
65                  70                  75                  80

Leu Ala Arg Asp Asp Val Asp Gly Val Val Ile Thr His Gly Thr Asp
                85                  90                  95

Thr Val Glu Glu Ser Ala Tyr Phe Leu His Leu Thr Val Lys Ser Asp
            100                 105                 110

Lys Pro Val Val Phe Val Ala Ala Met Arg Pro Ala Thr Ala Ile Ser
        115                 120                 125

Ala Asp Gly Pro Met Asn Leu Leu Glu Ala Val Arg Val Ala Gly Asp
    130                 135                 140

Lys Gln Ser Arg Gly Arg Gly Val Met Val Val Leu Asn Asp Arg Ile
145                 150                 155                 160

Gly Ser Ala Arg Tyr Ile Thr Lys Thr Asn Ala Ser Thr Leu Asp Thr
                165                 170                 175

Phe Lys Ala Asn Glu Glu Gly Tyr Leu Gly Val Ile Ile Gly Asn Arg
            180                 185                 190
```

```
Ile Tyr Tyr Gln Asn Arg Ile Asp Lys Leu His Thr Thr Arg Ser Val
            195                 200                 205

Phe Asp Val Arg Gly Leu Thr Ser Leu Pro Lys Val Asp Ile Leu Tyr
210                 215                 220

Gly Tyr Gln Asp Asp Pro Glu Tyr Leu Tyr Asp Ala Ala Ile Gln His
225                 230                 235                 240

Gly Val Lys Gly Ile Val Tyr Ala Gly Met Gly Ala Gly Ser Val Ser
            245                 250                 255

Val Arg Gly Ile Ala Gly Met Arg Lys Ala Met Glu Lys Gly Val Val
            260                 265                 270

Val Ile Arg Ser Thr Arg Thr Gly Asn Gly Ile Val Pro Pro Asp Glu
            275                 280                 285

Glu Leu Pro Gly Leu Val Ser Asp Ser Leu Asn Pro Ala His Ala Arg
290                 295                 300

Ile Leu Leu Met Leu Ala Leu Thr Arg Thr Ser Asp Pro Lys Val Ile
305                 310                 315                 320

Gln Glu Tyr Phe His Thr Tyr
            325

<210> SEQ ID NO 2
<211> LENGTH: 327
<212> TYPE: PRT
<213> ORGANISM: Artificial sequence
<220> FEATURE:
<223> OTHER INFORMATION: Synthetic polypeptide

<400> SEQUENCE: 2

Met Asp Lys Leu Pro Asn Ile Val Ile Leu Ala Thr Gly Gly Thr Ile
1               5                   10                  15

Ala Gly Ser Ala Ala Thr Gly Thr Gln Thr Thr Gly Tyr Lys Ala Gly
            20                  25                  30

Ala Leu Gly Val Asp Thr Leu Ile Asn Ala Val Pro Glu Val Lys Lys
        35                  40                  45

Leu Ala Asn Val Lys Gly Glu Gln Phe Ser Asn Met Ala Ser Gln Asn
50                  55                  60

Met Thr Gly Asp Val Val Leu Lys Leu Ser Gln Arg Val Asn Glu Leu
65                  70                  75                  80

Leu Ala Arg Asp Asp Val Asp Gly Val Val Ile Thr His Gly Thr Asp
            85                  90                  95

Thr Val Glu Glu Ser Ala Tyr Phe Leu His Leu Thr Val Lys Ser Asp
            100                 105                 110

Lys Pro Val Val Phe Val Ala Ala Met Arg Pro Ala Thr Ala Ile Ser
        115                 120                 125

Ala Asp Gly Pro Met Asn Leu Leu Glu Ala Val Arg Val Ala Gly Asp
        130                 135                 140

Lys Gln Ser Arg Gly Arg Gly Val Met Val Val Leu Asn Asp Arg Ile
145                 150                 155                 160

Gly Ser Ala Arg Tyr Ile Thr Lys Thr Asn Ala Ser Thr Leu Asp Thr
            165                 170                 175

Phe Lys Ala Asn Glu Glu Gly Tyr Leu Gly Val Ile Ile Gly Asn Arg
            180                 185                 190

Ile Tyr Tyr Gln Asn Arg Ile Asp Lys Leu His Thr Thr Arg Ser Val
            195                 200                 205

Phe Asp Val Arg Gly Leu Thr Ser Leu Pro Lys Val Asp Ile Leu Tyr
210                 215                 220
```

```
Gly Tyr Gln Asp Asp Pro Glu Tyr Leu Tyr Asp Ala Ile Gln His
225                 230                 235                 240

Gly Val Lys Gly Ile Val Tyr Ala Gly Met Gly Ala Gly Ser Val Ser
            245                 250                 255

Val Arg Gly Ile Ala Gly Met Arg Lys Ala Met Glu Lys Gly Val Val
            260                 265                 270

Val Ile Arg Ser Thr Arg Thr Gly Asn Gly Ile Val Pro Pro Asp Glu
            275                 280                 285

Glu Leu Pro Gly Leu Val Ser Asp Ser Leu Asn Pro Ala His Ala Arg
            290                 295                 300

Ile Leu Leu Met Leu Ala Leu Thr Arg Thr Ser Asp Pro Lys Val Ile
305                 310                 315                 320

Gln Glu Tyr Phe His Thr Tyr
                325
```

<210> SEQ ID NO 3
<211> LENGTH: 327
<212> TYPE: PRT
<213> ORGANISM: Artificial sequence
<220> FEATURE:
<223> OTHER INFORMATION: Synthetic polypeptide

<400> SEQUENCE: 3

```
Met Asp Lys Leu Pro Asn Ile Val Ile Leu Ala Thr Gly Gly Thr Ile
1               5                   10                  15

Ala Gly Ser Ala Ala Thr Gly Thr Gln Thr Thr Gly Tyr Lys Ala Gly
            20                  25                  30

Ala Leu Gly Val Asp Thr Leu Ile Asn Ala Val Pro Glu Val Lys Lys
            35                  40                  45

Leu Ala Asn Val Lys Gly Glu Gln Phe Ser Asn Met Ala Ser Gln Asn
        50                  55                  60

Met Thr Gly Asp Val Val Leu Lys Leu Ser Gln Arg Val Asn Glu Leu
65                  70                  75                  80

Leu Ala Arg Asp Asp Val Asp Gly Val Val Ile Thr His Gly Thr Asp
                85                  90                  95

Thr Val Glu Glu Ser Ala Tyr Phe Leu His Leu Thr Val Lys Ser Asp
            100                 105                 110

Lys Pro Val Val Phe Val Ala Ala Met Arg Pro Ala Thr Ala Ile Ser
            115                 120                 125

Ala Asp Gly Pro Met Asn Leu Leu Glu Ala Val Arg Val Ala Gly Asp
130                 135                 140

Lys Gln Ser Arg Gly Arg Gly Val Met Val Val Leu Asn Asp Arg Ile
145                 150                 155                 160

Gly Ser Ala Arg Tyr Ile Thr Lys Thr Asn Ala Ser Thr Leu Asp Thr
                165                 170                 175

Phe Lys Ala Asn Glu Glu Gly Tyr Leu Gly Val Ile Ile Gly Asn Arg
            180                 185                 190

Ile Tyr Tyr Gln Asn Arg Ile Asp Lys Leu His Thr Thr Arg Ser Val
            195                 200                 205

Phe Asp Val Arg Gly Leu Thr Ser Leu Pro Lys Val Asp Ile Leu Tyr
        210                 215                 220

Gly Tyr Gln Asp Asp Pro Glu Tyr Leu Tyr Asp Ala Ile Gln His
225                 230                 235                 240

Gly Val Lys Gly Ile Val Tyr Ala Gly Met Gly Ala Gly Asn Val Ser
            245                 250                 255
```

```
Val Arg Gly Ile Ala Gly Met Arg Lys Ala Met Glu Lys Gly Val Val
        260                 265                 270

Val Ile Arg Ser Thr Arg Thr Gly Asn Gly Ile Val Pro Pro Asp Glu
        275                 280                 285

Glu Leu Pro Gly Leu Val Ser Asp Ser Leu Asn Pro Ala His Ala Arg
        290                 295                 300

Ile Leu Leu Met Leu Ala Leu Thr Arg Thr Ser Asp Pro Lys Val Ile
305                 310                 315                 320

Gln Glu Tyr Phe His Thr Tyr
                325

<210> SEQ ID NO 4
<211> LENGTH: 327
<212> TYPE: PRT
<213> ORGANISM: Artificial sequence
<220> FEATURE:
<223> OTHER INFORMATION: Synthetic polypeptide

<400> SEQUENCE: 4

Met Asp Lys Leu Pro Asn Ile Val Ile Leu Ala Thr Gly Gly Thr Ile
1               5                   10                  15

Ala Gly Ser Ala Ala Thr Gly Thr Gln Thr Thr Gly Tyr Lys Ile Gly
                20                  25                  30

Ala Leu Gly Val Asp Thr Leu Ile Asn Ala Val Pro Glu Val Lys Lys
            35                  40                  45

Leu Ala Asn Val Lys Gly Glu Gln Phe Ser Asn Met Ala Ser Gln Asn
        50                  55                  60

Met Thr Gly Asp Val Val Leu Lys Leu Ser Gln Arg Val Asn Glu Leu
65                  70                  75                  80

Leu Ala Arg Asp Asp Val Asp Gly Val Val Ile Thr His Gly Thr Asp
                85                  90                  95

Thr Val Glu Glu Ser Ala Tyr Phe Leu His Leu Thr Val Lys Ser Asp
                100                 105                 110

Lys Pro Val Val Phe Val Ala Ala Met Arg Pro Ala Thr Ala Ile Ser
            115                 120                 125

Ala Asp Gly Pro Met Asn Leu Leu Glu Ala Val Arg Val Ala Gly Asp
        130                 135                 140

Lys Gln Ser Arg Gly Arg Gly Val Met Val Val Leu Asn Asp Arg Ile
145                 150                 155                 160

Gly Ser Ala Arg Tyr Ile Thr Lys Thr Asn Ala Ser Thr Leu Asp Thr
                165                 170                 175

Phe Lys Ala Asn Glu Glu Gly Tyr Leu Gly Val Ile Ile Gly Asn Arg
            180                 185                 190

Ile Tyr Tyr Gln Asn Arg Ile Asp Lys Leu His Thr Thr Arg Ser Val
        195                 200                 205

Phe Asp Val Arg Gly Leu Thr Ser Leu Pro Lys Val Asp Ile Leu Tyr
210                 215                 220

Gly Tyr Gln Asp Asp Pro Glu Tyr Leu Tyr Asp Ala Ala Ile Gln His
225                 230                 235                 240

Gly Val Lys Gly Ile Val Tyr Ala Gly Met Gly Ala Gly Ser Val Ser
                245                 250                 255

Val Arg Gly Ile Ala Gly Met Arg Lys Ala Met Glu Lys Gly Val Val
            260                 265                 270

Val Ile Arg Ser Thr Arg Thr Gly Asn Gly Ile Val Pro Pro Asp Glu
        275                 280                 285
```

```
Glu Leu Pro Gly Leu Val Ser Asp Ser Leu Asn Pro Ala His Ala Arg
        290                 295                 300

Ile Leu Leu Met Leu Ala Leu Thr Arg Thr Ser Asp Pro Lys Val Ile
305                 310                 315                 320

Gln Glu Tyr Phe His Thr Tyr
                325

<210> SEQ ID NO 5
<211> LENGTH: 327
<212> TYPE: PRT
<213> ORGANISM: Artificial sequence
<220> FEATURE:
<223> OTHER INFORMATION: Synthetic polypeptide

<400> SEQUENCE: 5

Met Asp Lys Leu Pro Asn Ile Val Ile Leu Ala Thr Gly Gly Thr Ile
1               5                   10                  15

Ala Gly Ser Ala Ala Thr Gly Thr Gln Thr Thr Gly Tyr Lys Ala Gly
            20                  25                  30

Ala Leu Gly Val Asp Thr Leu Ile Asn Ala Val Pro Glu Val Lys Lys
        35                  40                  45

Leu Ala Asn Val Lys Gly Glu Gln Phe Ser Asn Met Ala Ser Gln Asn
    50                  55                  60

Met Thr Gly Asp Val Val Leu Lys Leu Ser Gln Arg Val Asn Glu Leu
65                  70                  75                  80

Leu Ala Arg Asp Asp Val Asp Gly Val Val Ile Thr His Gly Thr Asp
                85                  90                  95

Thr Val Glu Glu Ser Ala Tyr Phe Leu His Leu Thr Val Lys Ser Asp
            100                 105                 110

Lys Pro Val Val Phe Val Ala Ala Met Arg Pro Ala Thr Ala Ile Ser
            115                 120                 125

Ala Asp Gly Pro Met Asn Leu Leu Glu Ala Val Arg Val Ala Gly Asp
        130                 135                 140

Lys Gln Ser Arg Gly Arg Gly Val Met Val Val Leu Asn Asp Arg Ile
145                 150                 155                 160

Gly Ser Ala Arg Tyr Ile Thr Lys Thr Asn Ala Ser Thr Leu Asp Thr
                165                 170                 175

Phe Lys Ala Asn Glu Glu Gly Tyr Leu Gly Val Ile Ile Gly Asn Arg
            180                 185                 190

Ile Tyr Tyr Gln Asn Arg Ile Asp Lys Leu His Thr Thr Arg Ser Val
        195                 200                 205

Phe Asp Val Arg Gly Leu Thr Ser Leu Pro Lys Val Asp Ile Leu Tyr
    210                 215                 220

Gly Tyr Gln Asp Asp Pro Glu Tyr Leu Tyr Asp Ala Ala Ile Gln His
225                 230                 235                 240

Gly Val Lys Gly Ile Val Tyr Ala Gly Met Gly Ala Gly Gln Val Ser
                245                 250                 255

Val Arg Gly Ile Ala Gly Met Arg Lys Ala Met Glu Lys Gly Val Val
            260                 265                 270

Val Ile Arg Ser Thr Arg Thr Gly Asn Gly Ile Val Pro Pro Asp Glu
        275                 280                 285

Glu Leu Pro Gly Leu Val Ser Asp Ser Leu Asn Pro Ala His Ala Arg
    290                 295                 300

Ile Leu Leu Met Leu Ala Leu Thr Arg Thr Ser Asp Pro Lys Val Ile
305                 310                 315                 320
```

Gln Glu Tyr Phe His Thr Tyr
            325

<210> SEQ ID NO 6
<211> LENGTH: 327
<212> TYPE: PRT
<213> ORGANISM: Artificial sequence
<220> FEATURE:
<223> OTHER INFORMATION: Synthetic polypeptide

<400> SEQUENCE: 6

Met Asp Lys Leu Pro Asn Ile Val Ile Leu Ala Thr Gly Gly Thr Ile
1               5                   10                  15

Ala Gly Ser Ala Ala Thr Gly Thr Gln Thr Thr Gly Tyr Lys Ile Gly
            20                  25                  30

Ala Leu Gly Val Asp Thr Leu Ile Asn Ala Val Pro Glu Val Lys Lys
        35                  40                  45

Leu Ala Asn Val Lys Gly Glu Gln Phe Ser Asn Met Ala Ser Gln Asn
    50                  55                  60

Met Thr Gly Asp Val Val Leu Lys Leu Ser Gln Arg Val Asn Glu Leu
65                  70                  75                  80

Leu Ala Arg Asp Asp Val Asp Gly Val Val Ile Thr His Gly Thr Asp
                85                  90                  95

Thr Val Glu Glu Ser Ala Tyr Phe Leu His Leu Thr Val Lys Ser Asp
            100                 105                 110

Lys Pro Val Val Phe Val Ala Ala Met Arg Pro Ala Thr Ala Ile Ser
        115                 120                 125

Ala Asp Gly Pro Met Asn Leu Leu Glu Ala Val Arg Val Ala Gly Asp
    130                 135                 140

Lys Gln Ser Arg Gly Arg Gly Val Met Val Val Leu Asn Asp Arg Ile
145                 150                 155                 160

Gly Ser Ala Arg Tyr Ile Thr Lys Thr Asn Ala Ser Thr Leu Asp Thr
                165                 170                 175

Phe Lys Ala Asn Glu Glu Gly Tyr Leu Gly Val Ile Ile Gly Asn Arg
            180                 185                 190

Ile Tyr Tyr Gln Asn Arg Ile Asp Lys Leu His Thr Thr Arg Ser Val
        195                 200                 205

Phe Asp Val Arg Gly Leu Thr Ser Leu Pro Lys Val Asp Ile Leu Tyr
    210                 215                 220

Gly Tyr Gln Asp Asp Pro Glu Tyr Leu Tyr Asp Ala Ala Ile Gln His
225                 230                 235                 240

Gly Val Lys Gly Ile Val Tyr Ala Gly Met Gly Ala Gly Gln Val Ser
                245                 250                 255

Val Arg Gly Ile Ala Gly Met Arg Lys Ala Met Glu Lys Gly Val Val
            260                 265                 270

Val Ile Arg Ser Thr Arg Thr Gly Asn Gly Ile Val Pro Pro Asp Glu
        275                 280                 285

Glu Leu Pro Gly Leu Val Ser Asp Ser Leu Asn Pro Ala His Ala Arg
    290                 295                 300

Ile Leu Leu Met Leu Ala Leu Thr Arg Thr Ser Asp Pro Lys Val Ile
305                 310                 315                 320

Gln Glu Tyr Phe His Thr Tyr
            325

<210> SEQ ID NO 7

<211> LENGTH: 327
<212> TYPE: PRT
<213> ORGANISM: Artificial sequence
<220> FEATURE:
<223> OTHER INFORMATION: Synthetic polypeptide

<400> SEQUENCE: 7

| | | | | | | | | | | | | | | | |
|---|---|---|---|---|---|---|---|---|---|---|---|---|---|---|---|
| Met | Asp | Lys | Leu | Pro | Asn | Ile | Val | Ile | Leu | Ala | Thr | Gly | Gly | Thr | Ile |
| 1 | | | | 5 | | | | | 10 | | | | | 15 | |
| Ala | Gly | Ser | Ala | Ala | Thr | Gly | Thr | Gln | Thr | Thr | Gly | Tyr | Lys | Ile | Gly |
| | | | 20 | | | | | 25 | | | | | 30 | | |
| Ala | Leu | Gly | Val | Asp | Thr | Leu | Ile | Asn | Ala | Val | Pro | Glu | Val | Lys | Lys |
| | | | 35 | | | | | 40 | | | | | 45 | | |
| Leu | Ala | Asn | Val | Lys | Gly | Glu | Gln | Phe | Ser | Asn | Met | Ala | Ser | Gln | Asn |
| 50 | | | | | 55 | | | | | 60 | | | | | |
| Met | Thr | Gly | Asp | Val | Val | Leu | Lys | Leu | Ser | Gln | Arg | Val | Asn | Glu | Leu |
| 65 | | | | | 70 | | | | | 75 | | | | | 80 |
| Leu | Ala | Arg | Asp | Asp | Val | Asp | Gly | Val | Val | Ile | Thr | His | Gly | Thr | Asp |
| | | | | 85 | | | | | 90 | | | | | 95 | |
| Thr | Val | Glu | Glu | Ser | Ala | Tyr | Phe | Leu | His | Leu | Thr | Val | Lys | Ser | Asp |
| | | | 100 | | | | | 105 | | | | | 110 | | |
| Lys | Pro | Val | Val | Phe | Val | Ala | Ala | Met | Arg | Pro | Ala | Thr | Ala | Ile | Ser |
| | | | 115 | | | | | 120 | | | | | 125 | | |
| Ala | Asp | Gly | Pro | Met | Asn | Leu | Leu | Glu | Ala | Val | Arg | Val | Ala | Gly | Asp |
| | 130 | | | | | 135 | | | | | 140 | | | | |
| Lys | Gln | Ser | Arg | Gly | Arg | Gly | Val | Met | Val | Val | Leu | Asn | Asp | Arg | Ile |
| 145 | | | | | 150 | | | | | 155 | | | | | 160 |
| Gly | Ser | Ala | Arg | Tyr | Ile | Thr | Lys | Thr | Asn | Ala | Ser | Thr | Leu | Asp | Thr |
| | | | | 165 | | | | | 170 | | | | | 175 | |
| Phe | Lys | Ala | Asn | Glu | Glu | Gly | Tyr | Leu | Gly | Val | Ile | Ile | Gly | Asn | Arg |
| | | | 180 | | | | | 185 | | | | | 190 | | |
| Ile | Tyr | Tyr | Gln | Asn | Arg | Ile | Asp | Lys | Leu | His | Thr | Thr | Arg | Ser | Val |
| | | | 195 | | | | | 200 | | | | | 205 | | |
| Phe | Asp | Val | Arg | Gly | Leu | Thr | Ser | Leu | Pro | Lys | Val | Asp | Ile | Leu | Tyr |
| | 210 | | | | | 215 | | | | | 220 | | | | |
| Gly | Tyr | Gln | Asp | Asp | Pro | Glu | Tyr | Leu | Tyr | Asp | Ala | Ala | Ile | Gln | His |
| 225 | | | | | 230 | | | | | 235 | | | | | 240 |
| Gly | Val | Lys | Gly | Ile | Val | Tyr | Ala | Gly | Met | Gly | Ala | Gly | Asn | Val | Ser |
| | | | | 245 | | | | | 250 | | | | | 255 | |
| Val | Arg | Gly | Ile | Ala | Gly | Met | Arg | Lys | Ala | Met | Glu | Lys | Gly | Val | Val |
| | | | 260 | | | | | 265 | | | | | 270 | | |
| Val | Ile | Arg | Ser | Thr | Arg | Thr | Gly | Asn | Gly | Ile | Val | Pro | Pro | Asp | Glu |
| | | | 275 | | | | | 280 | | | | | 285 | | |
| Glu | Leu | Pro | Gly | Leu | Val | Ser | Asp | Ser | Leu | Asn | Pro | Ala | His | Ala | Arg |
| | 290 | | | | | 295 | | | | | 300 | | | | |
| Ile | Leu | Leu | Met | Leu | Ala | Leu | Thr | Arg | Thr | Ser | Asp | Pro | Lys | Val | Ile |
| 305 | | | | | 310 | | | | | 315 | | | | | 320 |
| Gln | Glu | Tyr | Phe | His | Thr | Tyr | | | | | | | | | |
| | | | | 325 | | | | | | | | | | | |

<210> SEQ ID NO 8
<211> LENGTH: 325
<212> TYPE: PRT
<213> ORGANISM: Erwinia carotovora

<400> SEQUENCE: 8

```
Met Leu Pro Asn Ile Val Ile Leu Ala Thr Gly Gly Thr Ile Ala Gly
1               5                   10                  15

Ser Ala Ala Ala Asn Thr Gln Thr Thr Gly Tyr Lys Ala Gly Ala Leu
                20                  25                  30

Gly Val Glu Thr Leu Ile Gln Ala Val Pro Glu Leu Lys Thr Leu Ala
            35                  40                  45

Asn Ile Lys Gly Glu Gln Val Ala Ser Ile Gly Ser Glu Asn Met Thr
    50                  55                  60

Ser Asp Val Leu Leu Thr Leu Ser Lys Arg Val Asn Glu Leu Leu Ala
65                  70                  75                  80

Arg Ser Asp Val Asp Gly Val Val Ile Thr His Gly Thr Asp Thr Leu
                85                  90                  95

Asp Glu Ser Pro Tyr Phe Leu Asn Leu Thr Val Lys Ser Asp Lys Pro
            100                 105                 110

Val Val Phe Val Ala Ala Met Arg Pro Ala Thr Ala Ile Ser Ala Asp
        115                 120                 125

Gly Pro Met Asn Leu Tyr Gly Ala Val Lys Val Ala Ala Asp Lys Asn
    130                 135                 140

Ser Arg Gly Arg Gly Val Leu Val Val Leu Asn Asp Arg Ile Gly Ser
145                 150                 155                 160

Ala Arg Phe Ile Ser Lys Thr Asn Ala Ser Thr Leu Asp Thr Phe Lys
                165                 170                 175

Ala Pro Glu Glu Gly Tyr Leu Gly Val Ile Ile Gly Asp Lys Ile Tyr
            180                 185                 190

Tyr Gln Thr Arg Leu Asp Lys Val His Thr Thr Arg Ser Val Phe Asp
        195                 200                 205

Val Thr Asn Val Asp Lys Leu Pro Ala Val Asp Ile Ile Tyr Gly Tyr
    210                 215                 220

Gln Asp Asp Pro Glu Tyr Met Tyr Asp Ala Ser Ile Lys His Gly Val
225                 230                 235                 240

Lys Gly Ile Val Tyr Ala Gly Met Gly Ala Gly Ser Val Ser Lys Arg
                245                 250                 255

Gly Asp Ala Gly Ile Arg Lys Ala Glu Ser Lys Gly Ile Val Val Val
            260                 265                 270

Arg Ser Ser Arg Thr Gly Ser Gly Ile Val Pro Pro Asp Ala Gly Gln
        275                 280                 285

Pro Gly Leu Val Ala Asp Ser Leu Ser Pro Ala Lys Ser Arg Ile Leu
    290                 295                 300

Leu Met Leu Ala Leu Thr Lys Thr Thr Asn Pro Ala Val Ile Gln Asp
305                 310                 315                 320

Tyr Phe His Ala Tyr
                325

<210> SEQ ID NO 9
<211> LENGTH: 327
<212> TYPE: PRT
<213> ORGANISM: Escherichia coli

<400> SEQUENCE: 9

Met Leu Pro Asn Ile Thr Ile Leu Ala Thr Gly Gly Thr Ile Ala Gly
1               5                   10                  15

Gly Gly Asp Ser Ala Thr Lys Ser Asn Tyr Thr Val Gly Lys Val Gly
                20                  25                  30

Val Glu Asn Leu Val Asn Ala Val Pro Gln Leu Lys Asp Ile Ala Asn
            35                  40                  45
```

Val Lys Gly Glu Gln Val Val Asn Ile Gly Ser Gln Asp Met Asn Asp
     50                  55                  60

Asn Val Trp Leu Thr Leu Ala Lys Lys Ile Asn Thr Asp Cys Asp Lys
 65                  70                  75                  80

Thr Asp Gly Phe Val Ile Thr His Gly Thr Asp Thr Met Glu Glu Thr
                     85                  90                  95

Ala Tyr Phe Leu Asp Leu Thr Val Lys Cys Asp Lys Pro Val Val Met
                100                 105                 110

Val Gly Ala Met Arg Pro Ser Thr Ser Met Ser Ala Asp Gly Pro Phe
            115                 120                 125

Asn Leu Tyr Asn Ala Val Val Thr Ala Ala Asp Lys Ala Ser Ala Asn
        130                 135                 140

Arg Gly Val Leu Val Met Asn Asp Thr Val Leu Asp Gly Arg Asp
145                 150                 155                 160

Val Thr Lys Thr Asn Thr Thr Asp Val Ala Thr Phe Lys Ser Val Asn
                    165                 170                 175

Tyr Gly Pro Leu Gly Tyr Ile His Asn Gly Lys Ile Asp Tyr Gln Arg
                180                 185                 190

Thr Pro Ala Arg Lys His Thr Ser Asp Thr Pro Phe Asp Val Ser Lys
            195                 200                 205

Leu Asn Glu Leu Pro Lys Val Gly Ile Val Tyr Asn Tyr Ala Asn Ala
    210                 215                 220

Ser Asp Leu Pro Ala Lys Ala Leu Val Asp Ala Gly Tyr Asp Gly Ile
225                 230                 235                 240

Val Ser Ala Gly Val Gly Asn Gly Asn Leu Tyr Lys Ser Val Phe Asp
                    245                 250                 255

Thr Leu Ala Thr Ala Ala Lys Thr Gly Thr Ala Val Val Arg Ser Ser
                260                 265                 270

Arg Val Pro Thr Gly Ala Thr Thr Gln Asp Ala Glu Val Asp Asp Ala
            275                 280                 285

Lys Tyr Gly Phe Val Ala Ser Gly Thr Leu Asn Pro Gln Lys Ala Arg
    290                 295                 300

Val Leu Leu Gln Leu Ala Leu Thr Gln Thr Lys Asp Pro Gln Gln Ile
305                 310                 315                 320

Gln Gln Ile Phe Asn Gln Tyr
                325

<210> SEQ ID NO 10
<211> LENGTH: 330
<212> TYPE: PRT
<213> ORGANISM: Helicobacter pylori

<400> SEQUENCE: 10

Met Ala Gln Asn Leu Pro Thr Ile Ala Leu Leu Ala Thr Gly Gly Thr
1               5                   10                  15

Ile Ala Gly Ser Gly Ala Ser Ala Ser Leu Gly Ser Tyr Lys Ser Gly
                20                  25                  30

Glu Leu Gly Ile Lys Glu Leu Leu Lys Ala Ile Pro Ser Leu Asn Arg
            35                  40                  45

Leu Ala Arg Ile Gln Gly Glu Gln Ile Ser Asn Ile Gly Ser Gln Asp
        50                  55                  60

Met Asn Glu Glu Val Trp Phe Lys Leu Ala Lys Arg Ala Gln Glu Leu
65                  70                  75                  80

Leu Asp Asp Ser Arg Ile Gln Gly Val Val Ile Thr His Gly Thr Asp 85                  90                  95
Thr Leu Glu Glu Ser Ala Tyr Phe Leu Asn Leu Val Leu Arg Ser Thr
                100                 105                 110
Lys Pro Val Val Leu Val Gly Ala Met Arg Asn Ala Ala Ser Leu Ser
            115                 120                 125
Ala Asp Gly Ala Leu Asn Leu Tyr Asn Ala Val Ser Val Ala Leu Asn
        130                 135                 140
Glu Lys Ser Ala Asn Lys Gly Val Leu Val Met Asp Asp Asn Ile
145                 150                 155                 160
Phe Ser Ala Arg Glu Val Ile Lys Thr His Thr Thr His Thr Ser Thr
                165                 170                 175
Phe Lys Ala Leu Asn Ser Gly Ala Ile Gly Ser Val Tyr Tyr Gly Lys
            180                 185                 190
Thr Arg Tyr Tyr Met Gln Pro Leu Arg Lys His Thr Thr Glu Ser Glu
        195                 200                 205
Phe Ser Leu Ser Gln Leu Lys Thr Pro Leu Pro Lys Val Asp Ile Ile
        210                 215                 220
Tyr Thr His Ala Gly Met Thr Pro Asp Leu Phe Gln Ala Ser Leu Asn
225                 230                 235                 240
Ser His Ala Lys Gly Val Val Ile Ala Gly Val Asn Gly Asn Val
                245                 250                 255
Ser Ala Gly Phe Leu Lys Ala Met Gln Glu Ala Ser Gln Met Gly Val
            260                 265                 270
Val Ile Val Arg Ser Ser Arg Val Asn Ser Gly Glu Ile Thr Ser Gly
        275                 280                 285
Glu Ile Asp Asp Lys Ala Phe Ile Thr Ser Asp Asn Leu Asn Pro Gln
        290                 295                 300
Lys Ala Arg Val Leu Leu Gln Leu Ala Leu Thr Lys Thr Asn Asn Lys
305                 310                 315                 320
Glu Lys Ile Gln Glu Met Phe Glu Glu Tyr
                325                 330

<210> SEQ ID NO 11
<211> LENGTH: 330
<212> TYPE: PRT
<213> ORGANISM: Wolinella succinogenes

<400> SEQUENCE: 11

Met Ala Lys Pro Gln Val Thr Ile Leu Ala Thr Gly Gly Thr Ile Ala
1               5                   10                  15
Gly Ser Gly Glu Ser Ser Val Lys Ser Ser Tyr Ser Ala Gly Ala Val
            20                  25                  30
Thr Val Asp Lys Leu Leu Ala Ala Val Pro Ala Ile Asn Asp Leu Ala
        35                  40                  45
Thr Ile Lys Gly Glu Gln Ile Ser Ser Ile Gly Ser Gln Glu Met Thr
    50                  55                  60
Gly Lys Val Trp Leu Lys Leu Ala Lys Arg Val Asn Glu Leu Leu Ala
65                  70                  75                  80
Gln Lys Glu Thr Glu Ala Val Ile Ile Thr His Gly Thr Asp Thr Met
                85                  90                  95
Glu Glu Thr Ala Phe Phe Leu Asn Leu Thr Val Lys Ser Gln Lys Pro
                100                 105                 110
Val Val Leu Val Gly Ala Met Arg Ser Gly Ser Ser Met Ser Ala Asp
            115                 120                 125

Gly Pro Met Asn Leu Tyr Asn Ala Val Asn Val Ala Ile Asn Lys Ala
            130                 135                 140

Ser Thr Asn Lys Gly Val Val Ile Val Met Asn Asp Glu Ile His Ala
145                 150                 155                 160

Ala Arg Glu Ala Thr Lys Leu Asn Thr Thr Ala Val Asn Ala Phe Ala
                165                 170                 175

Ser Pro Asn Thr Gly Lys Ile Gly Thr Val Tyr Tyr Gly Lys Val Glu
            180                 185                 190

Tyr Phe Thr Gln Ser Val Arg Pro His Thr Leu Ala Ser Glu Phe Asp
                195                 200                 205

Ile Ser Lys Ile Glu Glu Leu Pro Arg Val Asp Ile Leu Tyr Ala His
210                 215                 220

Pro Asp Asp Thr Asp Val Leu Val Asn Ala Ala Leu Gln Ala Gly Ala
225                 230                 235                 240

Lys Gly Ile Ile His Ala Gly Met Gly Asn Gly Asn Pro Phe Pro Leu
                245                 250                 255

Thr Gln Asn Ala Leu Glu Lys Ala Ala Lys Ser Gly Val Val Val Ala
            260                 265                 270

Arg Ser Ser Arg Val Gly Ser Gly Ser Thr Thr Gln Glu Ala Glu Val
                275                 280                 285

Asp Asp Lys Lys Leu Gly Phe Val Ala Thr Glu Ser Leu Asn Pro Gln
290                 295                 300

Lys Ala Arg Val Leu Leu Met Leu Ala Leu Thr Lys Thr Ser Asp Arg
305                 310                 315                 320

Glu Ala Ile Gln Lys Ile Phe Ser Thr Tyr
                325                 330

<210> SEQ ID NO 12
<211> LENGTH: 353
<212> TYPE: PRT
<213> ORGANISM: Cavia porcellus

<400> SEQUENCE: 12

Met Ala Arg Ala Ser Gly Ser Glu Arg His Leu Leu Leu Ile Tyr Thr
1               5                   10                  15

Gly Gly Thr Leu Gly Met Gln Ser Lys Gly Val Leu Val Pro Gly
            20                  25                  30

Pro Gly Leu Val Thr Leu Leu Arg Thr Leu Pro Met Phe His Asp Lys
            35                  40                  45

Glu Phe Ala Gln Ala Gln Gly Leu Pro Asp His Ala Leu Ala Leu Pro
50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Asp Asp Trp Ile Arg Ile
                85                  90                  95

Ala Lys Ile Ile Glu Arg His Tyr Glu Gln Tyr Gln Gly Phe Val Val
                100                 105                 110

Ile His Gly Thr Asp Thr Met Ala Ser Gly Ala Ser Met Leu Ser Phe
            115                 120                 125

Met Leu Glu Asn Leu His Lys Pro Val Ile Leu Thr Gly Ala Gln Val
            130                 135                 140

Pro Ile Arg Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
                165                 170                 175

```
Asn Ser Gln Leu Phe Arg Gly Asn Arg Val Thr Lys Val Asp Ser Gln
            180                 185                 190

Lys Phe Glu Ala Phe Cys Ser Pro Asn Leu Ser Pro Leu Ala Thr Val
            195                 200                 205

Gly Ala Asp Val Thr Ile Ala Trp Asp Leu Val Arg Lys Val Lys Trp
            210                 215                 220

Lys Asp Pro Leu Val Val His Ser Asn Met Glu His Asp Val Ala Leu
225                 230                 235                 240

Leu Arg Leu Tyr Pro Gly Ile Pro Ala Ser Leu Val Arg Ala Phe Leu
            245                 250                 255

Gln Pro Pro Leu Lys Gly Val Val Leu Glu Thr Phe Gly Ser Gly Asn
            260                 265                 270

Gly Pro Ser Lys Pro Asp Leu Leu Gln Glu Leu Arg Ala Ala Ala Gln
            275                 280                 285

Arg Gly Leu Ile Met Val Asn Cys Ser Gln Cys Leu Arg Gly Ser Val
            290                 295                 300

Thr Pro Gly Tyr Ala Thr Ser Leu Ala Gly Ala Asn Ile Val Ser Gly
305                 310                 315                 320

Leu Asp Met Thr Ser Glu Ala Ala Leu Ala Lys Leu Ser Tyr Val Leu
            325                 330                 335

Gly Leu Pro Glu Leu Ser Leu Glu Arg Arg Gln Glu Leu Leu Ala Lys
            340                 345                 350

Asp

<210> SEQ ID NO 13
<211> LENGTH: 20
<212> TYPE: PRT
<213> ORGANISM: Artificial sequence
<220> FEATURE:
<223> OTHER INFORMATION: Synthetic peptide

<400> SEQUENCE: 13

Gln Arg Leu Ile Glu Asp Ile Cys Leu Pro Arg Trp Gly Cys Leu Trp
1               5                   10                  15

Glu Asp Asp Phe
            20

<210> SEQ ID NO 14
<211> LENGTH: 18
<212> TYPE: PRT
<213> ORGANISM: Artificial sequence
<220> FEATURE:
<223> OTHER INFORMATION: Synthetic peptide

<400> SEQUENCE: 14

Arg Leu Ile Glu Asp Ile Cys Leu Pro Arg Trp Gly Cys Leu Trp Glu
1               5                   10                  15

Asp Asp

<210> SEQ ID NO 15
<211> LENGTH: 15
<212> TYPE: PRT
<213> ORGANISM: Artificial sequence
<220> FEATURE:
<223> OTHER INFORMATION: Synthetic peptide

<400> SEQUENCE: 15

Arg Leu Ile Glu Asp Ile Cys Leu Pro Arg Trp Gly Cys Leu Trp
1               5                   10                  15
```

<210> SEQ ID NO 16
<211> LENGTH: 282
<212> TYPE: PRT
<213> ORGANISM: Homo sapiens

<400> SEQUENCE: 16

Met Ala Met Met Glu Val Gln Gly Gly Pro Ser Leu Gly Gln Thr Cys
1               5                   10                  15

Val Leu Ile Val Ile Phe Thr Val Leu Gln Ser Leu Cys Val Ala
            20                  25                  30

Val Thr Tyr Val Tyr Phe Thr Asn Glu Leu Lys Gln Met Gln Asp Lys
            35                  40                  45

Tyr Ser Lys Ser Gly Ile Ala Cys Phe Leu Lys Glu Asp Asp Ser Tyr
        50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly Leu
        275                 280

<210> SEQ ID NO 17
<211> LENGTH: 167
<212> TYPE: PRT
<213> ORGANISM: Homo sapiens

<400> SEQUENCE: 17

Arg Glu Arg Gly Pro Gln Arg Val Ala Ala His Ile Thr Gly Thr Arg
1               5                   10                  15

Gly Arg Ser Asn Thr Leu Ser Ser Pro Asn Ser Lys Asn Glu Lys Ala
            20                  25                  30

Leu Gly Arg Lys Ile Asn Ser Trp Glu Ser Ser Arg Ser Gly His Ser
        35                  40                  45

```
Phe Leu Ser Asn Leu His Leu Arg Asn Gly Glu Leu Val Ile His Glu
        50                  55                  60

Lys Gly Phe Tyr Tyr Ile Tyr Ser Gln Thr Tyr Phe Arg Phe Gln Glu
 65                  70                  75                  80

Glu Ile Lys Glu Asn Thr Lys Asn Asp Lys Gln Met Val Gln Tyr Ile
                 85                  90                  95

Tyr Lys Tyr Thr Ser Tyr Pro Asp Pro Ile Leu Leu Met Lys Ser Ala
                100                 105                 110

Arg Asn Ser Cys Trp Ser Lys Asp Ala Glu Tyr Gly Leu Tyr Ser Ile
                115                 120                 125

Tyr Gln Gly Gly Ile Phe Glu Leu Lys Glu Asn Asp Arg Ile Phe Val
        130                 135                 140

Ser Val Thr Asn Glu His Leu Ile Asp Met Asp His Glu Ala Ser Phe
145                 150                 155                 160

Phe Gly Ala Phe Leu Val Gly
                165

<210> SEQ ID NO 18
<211> LENGTH: 503
<212> TYPE: PRT
<213> ORGANISM: Artificial sequence
<220> FEATURE:
<223> OTHER INFORMATION: Synthetic polypeptide

<400> SEQUENCE: 18

Arg Glu Arg Gly Pro Gln Arg Val Ala Ala His Ile Thr Gly Thr Arg
 1               5                  10                  15

Gly Arg Ser Asn Thr Leu Ser Ser Pro Asn Ser Lys Asn Glu Lys Ala
                 20                  25                  30

Leu Gly Arg Lys Ile Asn Ser Trp Glu Ser Ser Arg Ser Gly His Ser
            35                  40                  45

Phe Leu Ser Asn Leu His Leu Arg Asn Gly Glu Leu Val Ile His Glu
        50                  55                  60

Lys Gly Phe Tyr Tyr Ile Tyr Ser Gln Thr Tyr Phe Arg Phe Gln Glu
 65                  70                  75                  80

Glu Ile Lys Glu Asn Thr Lys Asn Asp Lys Gln Met Val Gln Tyr Ile
                 85                  90                  95

Tyr Lys Tyr Thr Ser Tyr Pro Asp Pro Ile Leu Leu Met Lys Ser Ala
                100                 105                 110

Arg Asn Ser Cys Trp Ser Lys Asp Ala Glu Tyr Gly Leu Tyr Ser Ile
                115                 120                 125

Tyr Gln Gly Gly Ile Phe Glu Leu Lys Glu Asn Asp Arg Ile Phe Val
        130                 135                 140

Ser Val Thr Asn Glu His Leu Ile Asp Met Asp His Glu Ala Ser Phe
145                 150                 155                 160

Phe Gly Ala Phe Leu Val Gly Gly Arg Glu Arg Gly Pro Gln Arg Val
                165                 170                 175

Ala Ala His Ile Thr Gly Thr Arg Gly Arg Ser Asn Thr Leu Ser Ser
            180                 185                 190

Pro Asn Ser Lys Asn Glu Lys Ala Leu Gly Arg Lys Ile Asn Ser Trp
            195                 200                 205

Glu Ser Ser Arg Ser Gly His Ser Phe Leu Ser Asn Leu His Leu Arg
        210                 215                 220

Asn Gly Glu Leu Val Ile His Glu Lys Gly Phe Tyr Tyr Ile Tyr Ser
225                 230                 235                 240
```

```
Gln Thr Tyr Phe Arg Phe Gln Glu Glu Ile Lys Glu Asn Thr Lys Asn
                245                 250                 255

Asp Lys Gln Met Val Gln Tyr Ile Tyr Lys Tyr Thr Ser Tyr Pro Asp
            260                 265                 270

Pro Ile Leu Leu Met Lys Ser Ala Arg Asn Ser Cys Trp Ser Lys Asp
        275                 280                 285

Ala Glu Tyr Gly Leu Tyr Ser Ile Tyr Gln Gly Gly Ile Phe Glu Leu
    290                 295                 300

Lys Glu Asn Asp Arg Ile Phe Val Ser Val Thr Asn Glu His Leu Ile
305                 310                 315                 320

Asp Met Asp His Glu Ala Ser Phe Phe Gly Ala Phe Leu Val Gly Gly
                325                 330                 335

Arg Glu Arg Gly Pro Gln Arg Val Ala Ala His Ile Thr Gly Thr Arg
            340                 345                 350

Gly Arg Ser Asn Thr Leu Ser Ser Pro Asn Ser Lys Asn Glu Lys Ala
        355                 360                 365

Leu Gly Arg Lys Ile Asn Ser Trp Glu Ser Ser Arg Ser Gly His Ser
    370                 375                 380

Phe Leu Ser Asn Leu His Leu Arg Asn Gly Glu Leu Val Ile His Glu
385                 390                 395                 400

Lys Gly Phe Tyr Tyr Ile Tyr Ser Gln Thr Tyr Phe Arg Phe Gln Glu
                405                 410                 415

Glu Ile Lys Glu Asn Thr Lys Asn Asp Lys Gln Met Val Gln Tyr Ile
            420                 425                 430

Tyr Lys Tyr Thr Ser Tyr Pro Asp Pro Ile Leu Leu Met Lys Ser Ala
        435                 440                 445

Arg Asn Ser Cys Trp Ser Lys Asp Ala Glu Tyr Gly Leu Tyr Ser Ile
    450                 455                 460

Tyr Gln Gly Gly Ile Phe Glu Leu Lys Glu Asn Asp Arg Ile Phe Val
465                 470                 475                 480

Ser Val Thr Asn Glu His Leu Ile Asp Met Asp His Glu Ala Ser Phe
                485                 490                 495

Phe Gly Ala Phe Leu Val Gly
                500

<210> SEQ ID NO 19
<211> LENGTH: 16
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (5)..(15)
<223> OTHER INFORMATION: Residue may be present or absent

<400> SEQUENCE: 19

Gly Gly Gly Ser Gly Gly Gly Ser Gly Gly Gly Ser Gly Gly Gly Ser
1               5                   10                  15

<210> SEQ ID NO 20
<211> LENGTH: 24
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (10)..(24)
```

-continued

<223> OTHER INFORMATION: Residue may be present or absent.

<400> SEQUENCE: 20

```
Gly Gly Gly Ser Gly Gly Gly Ser Gly Gly Gly Ser Gly Gly
1               5                   10                  15

Gly Gly Ser Gly Gly Gly Gly Ser
            20
```

<210> SEQ ID NO 21
<211> LENGTH: 24
<212> TYPE: PRT
<213> ORGANISM: Artificial sequence
<220> FEATURE:
<223> OTHER INFORMATION: Synthetic peptide

<400> SEQUENCE: 21

```
Gly Gly Gly Ser Gly Gly Gly Ser Gly Gly Gly Ser Gly Gly
1               5                   10                  15

Gly Gly Ser Gly Gly Gly Gly Ser
            20
```

<210> SEQ ID NO 22
<211> LENGTH: 855
<212> TYPE: PRT
<213> ORGANISM: Artificial sequence
<220> FEATURE:
<223> OTHER INFORMATION: Synthetic polypeptide

<400> SEQUENCE: 22

```
Arg Glu Arg Gly Pro Gln Arg Val Ala Ala His Ile Thr Gly Thr Arg
1               5                   10                  15

Gly Arg Ser Asn Thr Leu Ser Ser Pro Asn Ser Lys Asn Glu Lys Ala
            20                  25                  30

Leu Gly Arg Lys Ile Asn Ser Trp Glu Ser Ser Arg Ser Gly His Ser
        35                  40                  45

Phe Leu Ser Asn Leu His Leu Arg Asn Gly Glu Leu Val Ile His Glu
    50                  55                  60

Lys Gly Phe Tyr Tyr Ile Tyr Ser Gln Thr Tyr Phe Arg Phe Gln Glu
65                  70                  75                  80

Glu Ile Lys Glu Asn Thr Lys Asn Asp Lys Gln Met Val Gln Tyr Ile
                85                  90                  95

Tyr Lys Tyr Thr Ser Tyr Pro Asp Pro Ile Leu Leu Met Lys Ser Ala
            100                 105                 110

Arg Asn Ser Cys Trp Ser Lys Asp Ala Glu Tyr Gly Leu Tyr Ser Ile
        115                 120                 125

Tyr Gln Gly Gly Ile Phe Glu Leu Lys Glu Asn Asp Arg Ile Phe Val
    130                 135                 140

Ser Val Thr Asn Glu His Leu Ile Asp Met Asp His Glu Ala Ser Phe
145                 150                 155                 160

Phe Gly Ala Phe Leu Val Gly Gly Arg Glu Gly Pro Gln Arg Val
                165                 170                 175

Ala Ala His Ile Thr Gly Thr Arg Gly Arg Ser Asn Thr Leu Ser Ser
            180                 185                 190

Pro Asn Ser Lys Asn Glu Lys Ala Leu Gly Arg Lys Ile Asn Ser Trp
        195                 200                 205

Glu Ser Ser Arg Ser Gly His Ser Phe Leu Ser Asn Leu His Leu Arg
    210                 215                 220

Asn Gly Glu Leu Val Ile His Glu Lys Gly Phe Tyr Tyr Ile Tyr Ser
```

```
            225                 230                 235                 240
        Gln Thr Tyr Phe Arg Phe Gln Glu Glu Ile Lys Glu Asn Thr Lys Asn
                            245                 250                 255

Asp Lys Gln Met Val Gln Tyr Ile Tyr Lys Tyr Thr Ser Tyr Pro Asp
                            260                 265                 270

Pro Ile Leu Leu Met Lys Ser Ala Arg Asn Ser Cys Trp Ser Lys Asp
                            275                 280                 285

Ala Glu Tyr Gly Leu Tyr Ser Ile Tyr Gln Gly Gly Ile Phe Glu Leu
                            290                 295                 300

Lys Glu Asn Asp Arg Ile Phe Val Ser Val Thr Asn Glu His Leu Ile
        305                 310                 315                 320

Asp Met Asp His Glu Ala Ser Phe Phe Gly Ala Phe Leu Val Gly Gly
                            325                 330                 335

Arg Glu Arg Gly Pro Gln Arg Val Ala Ala His Ile Thr Gly Thr Arg
                            340                 345                 350

Gly Arg Ser Asn Thr Leu Ser Ser Pro Asn Ser Lys Asn Glu Lys Ala
                            355                 360                 365

Leu Gly Arg Lys Ile Asn Ser Trp Glu Ser Ser Arg Ser Gly His Ser
        370                 375                 380

Phe Leu Ser Asn Leu His Leu Arg Asn Gly Glu Leu Val Ile His Glu
        385                 390                 395                 400

Lys Gly Phe Tyr Tyr Ile Tyr Ser Gln Thr Tyr Phe Arg Phe Gln Glu
                            405                 410                 415

Glu Ile Lys Glu Asn Thr Lys Asn Asp Lys Gln Met Val Gln Tyr Ile
                            420                 425                 430

Tyr Lys Tyr Thr Ser Tyr Pro Asp Pro Ile Leu Leu Met Lys Ser Ala
                            435                 440                 445

Arg Asn Ser Cys Trp Ser Lys Asp Ala Glu Tyr Gly Leu Tyr Ser Ile
                            450                 455                 460

Tyr Gln Gly Gly Ile Phe Glu Leu Lys Glu Asn Asp Arg Ile Phe Val
        465                 470                 475                 480

Ser Val Thr Asn Glu His Leu Ile Asp Met Asp His Glu Ala Ser Phe
                            485                 490                 495

Phe Gly Ala Phe Leu Val Gly Gly Gly Ser Gly Gly Gly Gly Ser
                            500                 505                 510

Gly Gly Gly Gly Ser Gly Gly Gly Ser Gly Gly Gly Ser His
                            515                 520                 525

Met Asp Lys Leu Pro Asn Ile Val Ile Leu Ala Thr Gly Gly Thr Ile
        530                 535                 540

Ala Gly Ser Ala Ala Thr Gly Thr Gln Thr Thr Gly Tyr Lys Ile Gly
        545                 550                 555                 560

Ala Leu Gly Val Asp Thr Leu Ile Asn Ala Val Pro Glu Val Lys Lys
                            565                 570                 575

Leu Ala Asn Val Lys Gly Glu Gln Phe Ser Asn Met Ala Ser Gln Asn
                            580                 585                 590

Met Thr Gly Asp Val Val Leu Lys Leu Ser Gln Arg Val Asn Glu Leu
                            595                 600                 605

Leu Ala Arg Asp Asp Val Asp Gly Val Val Ile Thr His Gly Thr Asp
                            610                 615                 620

Thr Val Glu Glu Ser Ala Tyr Phe Leu His Leu Thr Val Lys Ser Asp
        625                 630                 635                 640

Lys Pro Val Val Phe Val Ala Ala Met Arg Pro Ala Thr Ala Ile Ser
                            645                 650                 655
```

```
Ala Asp Gly Pro Met Asn Leu Leu Glu Ala Val Arg Val Ala Gly Asp
            660                 665                 670

Lys Gln Ser Arg Gly Arg Gly Val Met Val Val Leu Asn Asp Arg Ile
        675                 680                 685

Gly Ser Ala Arg Tyr Ile Thr Lys Thr Asn Ala Ser Thr Leu Asp Thr
    690                 695                 700

Phe Lys Ala Asn Glu Glu Gly Tyr Leu Gly Val Ile Ile Gly Asn Arg
705                 710                 715                 720

Ile Tyr Tyr Gln Asn Arg Ile Asp Lys Leu His Thr Thr Arg Ser Val
                725                 730                 735

Phe Asp Val Arg Gly Leu Thr Ser Leu Pro Lys Val Asp Ile Leu Tyr
            740                 745                 750

Gly Tyr Gln Asp Asp Pro Glu Tyr Leu Tyr Asp Ala Ala Ile Gln His
        755                 760                 765

Gly Val Lys Gly Ile Val Tyr Ala Gly Met Gly Ala Gly Gln Val Ser
    770                 775                 780

Val Arg Gly Ile Ala Gly Met Arg Lys Ala Met Glu Lys Gly Val Val
785                 790                 795                 800

Val Ile Arg Ser Thr Arg Thr Gly Asn Gly Ile Val Pro Pro Asp Glu
                805                 810                 815

Glu Leu Pro Gly Leu Val Ser Asp Ser Leu Asn Pro Ala His Ala Arg
            820                 825                 830

Ile Leu Leu Met Leu Ala Leu Thr Arg Thr Ser Asp Pro Lys Val Ile
        835                 840                 845

Gln Glu Tyr Phe His Thr Tyr
    850                 855

<210> SEQ ID NO 23
<211> LENGTH: 967
<212> TYPE: PRT
<213> ORGANISM: Artificial sequence
<220> FEATURE:
<223> OTHER INFORMATION: Synthetic polypeptide

<400> SEQUENCE: 23

Met Gly Ser Ser His His His His His His Gly Thr Met Ser Asp Ser
1               5                   10                  15

Glu Val Asn Gln Glu Ala Lys Pro Glu Val Lys Pro Glu Val Lys Pro
            20                  25                  30

Glu Thr His Ile Asn Leu Lys Val Ser Asp Gly Ser Ser Glu Ile Phe
        35                  40                  45

Phe Lys Ile Lys Lys Thr Thr Pro Leu Arg Arg Leu Met Glu Ala Phe
    50                  55                  60

Ala Lys Arg Gln Gly Lys Glu Met Asp Ser Leu Arg Phe Leu Tyr Asp
65                  70                  75                  80

Gly Ile Arg Ile Gln Ala Asp Gln Thr Pro Glu Asp Leu Asp Met Glu
                85                  90                  95

Asp Asn Asp Ile Ile Glu Ala His Arg Glu Gln Ile Gly Gly Leu Glu
            100                 105                 110

Arg Glu Arg Gly Pro Gln Arg Val Ala Ala His Ile Thr Gly Thr Arg
        115                 120                 125

Gly Arg Ser Asn Thr Leu Ser Ser Pro Asn Ser Lys Asn Glu Lys Ala
    130                 135                 140

Leu Gly Arg Lys Ile Asn Ser Trp Glu Ser Ser Arg Ser Gly His Ser
145                 150                 155                 160
```

-continued

```
Phe Leu Ser Asn Leu His Leu Arg Asn Gly Glu Leu Val Ile His Glu
                165                 170                 175

Lys Gly Phe Tyr Tyr Ile Tyr Ser Gln Thr Tyr Phe Arg Phe Gln Glu
            180                 185                 190

Glu Ile Lys Glu Asn Thr Lys Asn Asp Lys Gln Met Val Gln Tyr Ile
        195                 200                 205

Tyr Lys Tyr Thr Ser Tyr Pro Asp Pro Ile Leu Leu Met Lys Ser Ala
    210                 215                 220

Arg Asn Ser Cys Trp Ser Lys Asp Ala Glu Tyr Gly Leu Tyr Ser Ile
225                 230                 235                 240

Tyr Gln Gly Gly Ile Phe Glu Leu Lys Glu Asn Asp Arg Ile Phe Val
                245                 250                 255

Ser Val Thr Asn Glu His Leu Ile Asp Met Asp His Glu Ala Ser Phe
            260                 265                 270

Phe Gly Ala Phe Leu Val Gly Gly Arg Glu Arg Gly Pro Gln Arg Val
        275                 280                 285

Ala Ala His Ile Thr Gly Thr Arg Gly Arg Ser Asn Thr Leu Ser Ser
    290                 295                 300

Pro Asn Ser Lys Asn Glu Lys Ala Leu Gly Arg Lys Ile Asn Ser Trp
305                 310                 315                 320

Glu Ser Ser Arg Ser Gly His Ser Phe Leu Ser Asn Leu His Leu Arg
                325                 330                 335

Asn Gly Glu Leu Val Ile His Glu Lys Gly Phe Tyr Tyr Ile Tyr Ser
            340                 345                 350

Gln Thr Tyr Phe Arg Phe Gln Glu Glu Ile Lys Glu Asn Thr Lys Asn
        355                 360                 365

Asp Lys Gln Met Val Gln Tyr Ile Tyr Lys Tyr Thr Ser Tyr Pro Asp
    370                 375                 380

Pro Ile Leu Leu Met Lys Ser Ala Arg Asn Ser Cys Trp Ser Lys Asp
385                 390                 395                 400

Ala Glu Tyr Gly Leu Tyr Ser Ile Tyr Gln Gly Gly Ile Phe Glu Leu
                405                 410                 415

Lys Glu Asn Asp Arg Ile Phe Val Ser Val Thr Asn Glu His Leu Ile
            420                 425                 430

Asp Met Asp His Glu Ala Ser Phe Phe Gly Ala Phe Leu Val Gly Gly
        435                 440                 445

Arg Glu Arg Gly Pro Gln Arg Val Ala Ala His Ile Thr Gly Thr Arg
    450                 455                 460

Gly Arg Ser Asn Thr Leu Ser Ser Pro Asn Ser Lys Asn Glu Lys Ala
465                 470                 475                 480

Leu Gly Arg Lys Ile Asn Ser Trp Glu Ser Ser Arg Ser Gly His Ser
                485                 490                 495

Phe Leu Ser Asn Leu His Leu Arg Asn Gly Glu Leu Val Ile His Glu
            500                 505                 510

Lys Gly Phe Tyr Tyr Ile Tyr Ser Gln Thr Tyr Phe Arg Phe Gln Glu
        515                 520                 525

Glu Ile Lys Glu Asn Thr Lys Asn Asp Lys Gln Met Val Gln Tyr Ile
    530                 535                 540

Tyr Lys Tyr Thr Ser Tyr Pro Asp Pro Ile Leu Leu Met Lys Ser Ala
545                 550                 555                 560

Arg Asn Ser Cys Trp Ser Lys Asp Ala Glu Tyr Gly Leu Tyr Ser Ile
                565                 570                 575
```

```
Tyr Gln Gly Gly Ile Phe Glu Leu Lys Glu Asn Asp Arg Ile Phe Val
                580                 585                 590

Ser Val Thr Asn Glu His Leu Ile Asp Met Asp His Glu Ala Ser Phe
        595                 600                 605

Phe Gly Ala Phe Leu Val Gly Gly Gly Ser Gly Gly Gly Gly Ser
610                 615                 620

Gly Gly Gly Gly Ser Gly Gly Gly Ser Gly Gly Gly Ser His
625                 630                 635                 640

Met Asp Lys Leu Pro Asn Ile Val Ile Leu Ala Thr Gly Gly Thr Ile
                645                 650                 655

Ala Gly Ser Ala Ala Thr Gly Thr Gln Thr Thr Gly Tyr Lys Ile Gly
        660                 665                 670

Ala Leu Gly Val Asp Thr Leu Ile Asn Ala Val Pro Glu Val Lys Lys
        675                 680                 685

Leu Ala Asn Val Lys Gly Glu Gln Phe Ser Asn Met Ala Ser Gln Asn
        690                 695                 700

Met Thr Gly Asp Val Val Leu Lys Leu Ser Gln Arg Val Asn Glu Leu
705                 710                 715                 720

Leu Ala Arg Asp Asp Val Asp Gly Val Val Ile Thr His Gly Thr Asp
                725                 730                 735

Thr Val Glu Glu Ser Ala Tyr Phe Leu His Leu Thr Val Lys Ser Asp
                740                 745                 750

Lys Pro Val Val Phe Val Ala Ala Met Arg Pro Ala Thr Ala Ile Ser
        755                 760                 765

Ala Asp Gly Pro Met Asn Leu Leu Glu Ala Val Arg Val Ala Gly Asp
770                 775                 780

Lys Gln Ser Arg Gly Arg Gly Val Met Val Val Leu Asn Asp Arg Ile
785                 790                 795                 800

Gly Ser Ala Arg Tyr Ile Thr Lys Thr Asn Ala Ser Thr Leu Asp Thr
                805                 810                 815

Phe Lys Ala Asn Glu Glu Gly Tyr Leu Gly Val Ile Ile Gly Asn Arg
        820                 825                 830

Ile Tyr Tyr Gln Asn Arg Ile Asp Lys Leu His Thr Thr Arg Ser Val
        835                 840                 845

Phe Asp Val Arg Gly Leu Thr Ser Leu Pro Lys Val Asp Ile Leu Tyr
850                 855                 860

Gly Tyr Gln Asp Asp Pro Glu Tyr Leu Tyr Asp Ala Ala Ile Gln His
865                 870                 875                 880

Gly Val Lys Gly Ile Val Tyr Ala Gly Met Gly Ala Gly Gln Val Ser
                885                 890                 895

Val Arg Gly Ile Ala Gly Met Arg Lys Ala Met Glu Lys Gly Val Val
        900                 905                 910

Val Ile Arg Ser Thr Arg Thr Gly Asn Gly Ile Val Pro Pro Asp Glu
        915                 920                 925

Glu Leu Pro Gly Leu Val Ser Asp Ser Leu Asn Pro Ala His Ala Arg
        930                 935                 940

Ile Leu Leu Met Leu Ala Leu Thr Arg Thr Ser Asp Pro Lys Val Ile
945                 950                 955                 960

Gln Glu Tyr Phe His Thr Tyr
                965

<210> SEQ ID NO 24
<211> LENGTH: 57
<212> TYPE: DNA
```

<213> ORGANISM: Artificial sequence
<220> FEATURE:
<223> OTHER INFORMATION: Synthetic oligonucleotide

<400> SEQUENCE: 24
ggcggtggca gcggtggagg aggctctggt ggaggcggta gcggaggcgg agggtcg    57

<210> SEQ ID NO 25
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 25
cgaatgcatc tagatctcga gcgtgagcgt g    31

<210> SEQ ID NO 26
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 26
cacgctcacg ctcgagatct agatgcattc g    31

<210> SEQ ID NO 27
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 27
gaacagattg gtggtctcga gggaggaatt ccatatggat aaactg    46

<210> SEQ ID NO 28
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 28
cagtttatcc atatggaatt cctccctcga gaccaccaat ctgttc    46

<210> SEQ ID NO 29
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 29
gcacgctata tcaccatgac gaacgcttcg acc    33

<210> SEQ ID NO 30
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 30
ggtcgaagcg ttcgtcatgg tgatatagcg tgc    33

```
<210> SEQ ID NO 31
<211> LENGTH: 27
<212> TYPE: PRT
<213> ORGANISM: Artificial sequence
<220> FEATURE:
<223> OTHER INFORMATION: Synthetic peptide

<400> SEQUENCE: 31

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25
```